United States Patent
Collard et al.

(10) Patent No.: US 10,934,546 B2
(45) Date of Patent: Mar. 2, 2021

(54) TREATMENT OF SIRTUIN (SIRT) RELATED DISEASES BY INHIBITION OF NATURAL ANTISENSE TRANSCRIPT TO A SIRTUIN (SIRT)

(71) Applicant: CuRNA, Inc., Miami, FL (US)

(72) Inventors: Joseph Collard, Delray Beach, FL (US); Olga Khorkova Sherman, Tequesta, FL (US)

(73) Assignee: CuRNA, Inc., Miami, FL (US)

(*) Notice: Subject to any disclaimer, the term of this patent is extended or adjusted under 35 U.S.C. 154(b) by 0 days.

(21) Appl. No.: 16/739,266

(22) Filed: Jan. 10, 2020

(65) Prior Publication Data

US 2020/0131517 A1    Apr. 30, 2020

Related U.S. Application Data

(60) Division of application No. 14/701,998, filed on May 1, 2015, now Pat. No. 10,563,202, which is a continuation of application No. 13/386,057, filed as application No. PCT/US2010/043075 on Jul. 23, 2010, now abandoned, which is a continuation-in-part of application No. PCT/US2010/026119, filed on Mar. 3, 2010, and a continuation-in-part of application No. PCT/US2009/066445, filed on Dec. 2, 2009.

(60) Provisional application No. 61/228,392, filed on Jul. 24, 2009, provisional application No. 61/259,072, filed on Nov. 6, 2009.

(51) Int. Cl.
*C12N 15/11* (2006.01)
*C12N 15/113* (2010.01)

(52) U.S. Cl.
CPC .. *C12N 15/1137* (2013.01); *C12Y 305/01098* (2013.01); *C12N 2310/11* (2013.01); *C12N 2310/14* (2013.01); *C12N 2310/315* (2013.01); *C12N 2320/30* (2013.01)

(58) Field of Classification Search
CPC .................................................... C12N 15/113
See application file for complete search history.

(56) References Cited

U.S. PATENT DOCUMENTS

2005/0100885 A1 * 5/2005 Crooke .............. C12N 15/1131
                                                                435/5
2007/0031843 A1 * 2/2007 Bentwich ............... C12Q 1/689
                                                                435/6.11

FOREIGN PATENT DOCUMENTS

WO    WO-0078341 A1 * 12/2000    ......... C12N 15/1136
WO    WO-2004056993 A1 * 7/2004    ........... C07K 14/415

OTHER PUBLICATIONS

Machine translation of WO 2004/056993, pp. 1-148 (Year: 2004).*

* cited by examiner

*Primary Examiner* — Ekaterina Poliakova-Georgantas
(74) *Attorney, Agent, or Firm* — CuRNA, Inc.; Monte R. Browder

(57) ABSTRACT

The present invention relates to antisense oligonucleotides that modulate the expression of and/or function of a Sirtuin (SIRT), in particular, by targeting natural antisense polynucleotides of a Sirtuin (SIRT). The invention also relates to the identification of these antisense oligonucleotides and their use in treating diseases and disorders associated with the expression of Sirtuins (SIRT)s.

18 Claims, 10 Drawing Sheets

Specification includes a Sequence Listing.

US 10,934,546 B2

TREATMENT OF SIRTUIN (SIRT) RELATED DISEASES BY INHIBITION OF NATURAL ANTISENSE TRANSCRIPT TO A SIRTUIN (SIRT)

The present application is a Divisional of U.S. application Ser. No. 14/701,998 filed May 1, 2015, which is a Continuation of U.S. application Ser. No. 13/386,057 filed Jan. 20, 2012, which is National Phase Application of PCT/US2010/043075 filed Jul. 23, 2010, which is a Continuation-in-part of PCT/US2010/026119 filed Mar. 3, 2010, which is a Continuation-in-part of PCT/US2009/066445 filed Dec. 2, 2009, which claims priority of U.S. Provisional Patent Application Nos. 61/228,392 filed Jul. 24, 2009 and U.S. provisional patent application No. 61/259,072, filed Nov. 6, 2009, which are all incorporated herein by reference in their entirety.

FIELD OF THE INVENTION

Embodiments of the invention comprise oligonucleotides modulating expression and/or function of a Sirtuin (SIRT) and associated molecules.

BACKGROUND

DNA-RNA and RNA-RNA hybridization are important to many aspects of nucleic acid function including DNA replication, transcription, and translation. Hybridization is also central to a variety of technologies that either detect a particular nucleic acid or alter its expression. Antisense nucleotides, for example, disrupt gene expression by hybridizing to target RNA, thereby interfering with RNA splicing, transcription, translation, and replication. Antisense DNA has the added feature that DNA-RNA hybrids serve as a substrate for digestion by ribonuclease H, an activity that is present in most cell types. Antisense molecules can be delivered into cells, as is the case for oligodeoxynucleotides (ODNs), or they can be expressed from endogenous genes as RNA molecules. The FDA recently approved an antisense drug, VITRAVENE™ (for treatment of cytomegalovirus retinitis), reflecting that antisense has therapeutic utility.

SUMMARY

In one embodiment, the invention provides methods for inhibiting the action of a natural antisense transcript by using antisense oligonucleotide(s) targeted to any region of the natural antisense transcript resulting in up-regulation of the corresponding sense gene. It is also contemplated herein that inhibition of the natural antisense transcript can be achieved by siRNA, ribozymes and small molecules, which are considered to be within the scope of the present invention.

One embodiment provides a method of modulating function and/or expression of a Sirtuin (SIRT) polynucleotide in patient cells or tissues in vivo or in vitro comprising contacting said cells or tissues with an antisense oligonucleotide 5 to 30 nucleotides in length wherein said oligonucleotide has at least 50% sequence identity to a reverse complement of a polynucleotide comprising 5 to 30 consecutive nucleotides within nucleotides 1 to 1028 of SEQ ID NO: 5 or nucleotides 1 to 429 of SEQ ID NO: 6, or nucleotides 1 to 156 of SEQ ID NO: 7 or nucleotides 1 to 593 of SEQ ID NO:8, 1 to 373 of SEQ ID NO: 9, 1 to 1713 of SEQ ID NO: 10, 1 to 660 of SEQ ID NO: 11, 1 to 589 of SEQ ID NO: 12, 1 to 428 of SEQ ID NO: 13 and 1 to 4041 of SEQ ID NO: 14 thereby modulating function an or expression of the Sirtuin (SIRT) polynucleotide in patient cells or tissues in vivo or in vitro.

In another embodiment, an oligonucleotide targets a natural antisense sequence of a Sirtuin (SIRT) polynucleotide, for example, nucleotides set forth in SEQ ID NO: 5 to 14, and any variants, alleles, homologs, mutants, derivatives, fragments and complementary sequences thereto. Examples of antisense oligonucleotides are set forth as SEQ ID NOS: 15 to 94.

Another embodiment provides a method of modulating function and/or expression of a Sirtuin (SIRT) polynucleotide in patient cells or tissues in vivo or in vitro comprising contacting said cells or tissues with an antisense oligonucleotide 5 to 30 nucleotides in length wherein said oligonucleotide has at least 50% sequence identity to a reverse complement of the an antisense of the Sirtuin (SIRT) polynucleotide; thereby modulating function and/or expression of the Sirtuin (SIRT) polynucleotide in patient cells or tissues in vivo or in vitro.

Another embodiment provides a method of modulating function and/or expression of a Sirtuin (SIRT) polynucleotide in patient cells or tissues in vivo or in vitro comprising contacting said cells or tissues with an antisense oligonucleotide 5 to 30 nucleotides in length wherein said oligonucleotide has at least 50% sequence identity to an antisense oligonucleotide to a Sirtuin (SIRT) antisense polynucleotide; thereby modulating function and/or expression of the Sirtuin (SIRT) polynucleotide in patient cells or tissues in vivo or in vitro.

In one embodiment, a composition comprises one or more antisense oligonucleotides which bind to sense and/or antisense Sirtuin (SIRT) polynucleotides.

In another embodiment, the oligonucleotides comprise one or more modified or substituted nucleotides.

In another embodiment, the oligonucleotides comprise one or more modified bonds.

In yet another embodiment, the modified nucleotides comprise modified bases comprising phosphorothioate, methylphosphonate, peptide nucleic acids, 2'-O-methyl, fluoro- or carbon, methylene or other locked nucleic acid (LNA) molecules. Preferably, the modified nucleotides are locked nucleic acid molecules, including α-L-LNA.

In another embodiment, the oligonucleotides are administered to a patient subcutaneously, intramuscularly, intravenously or intraperitoneally.

In another embodiment, the oligonucleotides are administered in a pharmaceutical composition. A treatment regimen comprises administering the antisense compounds at least once to patient; however, this treatment can be modified to include multiple doses over a period of time. The treatment can be combined with one or more other types of therapies.

In another embodiment, the oligonucleotides are encapsulated in a liposome or attached to a carrier molecule (e.g. cholesterol, TAT peptide).

Other aspects are described infra.

SEQUENCE LISTING DESCRIPTION

Figure 1:
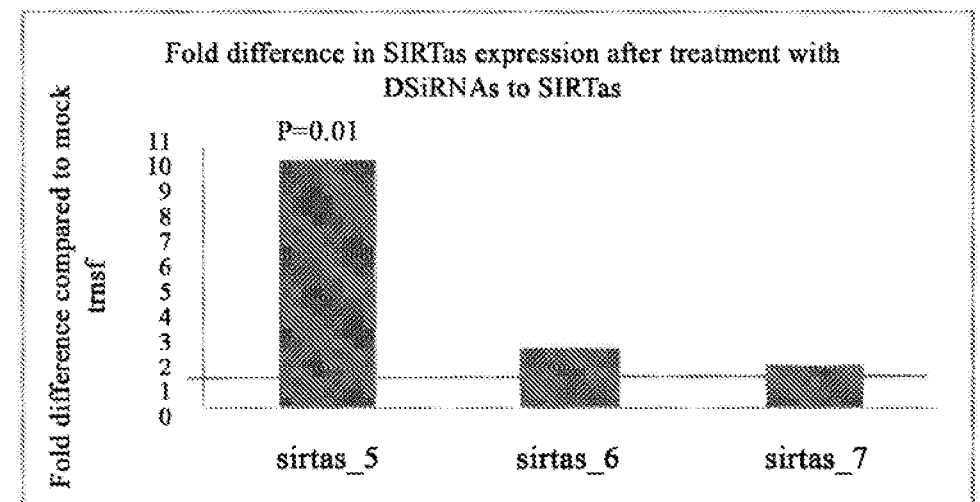
FIGS. 1 and 2 show Real time PCR results of oligonucleotides designed to SIRT antisense CV396200. The results show that the levels of the SIRT1 mRNA in HepG2 cells are significantly increased 48 h after treatment with one of the siRNAs designed to sirtas (sirtas_5, P=0.01). In the same samples the levels of sirtas RNA were significantly decreased after treatment with sirtas_5, but unchanged after treatment with sirtas_6 and sirtas_7, which also had no effect on the SIRT1 mRNA levels (FIG. 2). sirtas_5, sirtas_6 and sirtas_7 correspond to SEQ ID NOs: 38, 39 and 40 respectively.

SEQ ID NO: 1: *Homo sapiens* sirtuin (silent mating type information regulation 2 homolog) 1 (*S. cerevisiae*) (SIRT1), mRNA (NCBI Accession Number: NM 012238.3)

SEQ ID NO: 2: *Mus musculus* sirtuin 1 (silent mating type information regulation 2, homolog) 1 (*S. cerevisiae*) (SIRT1) mRNA (NCBI Accession Number: NM_001159589)

SEQ ID NO: 3: *Homo sapiens* sirtuin (silent mating type information regulation 2 homolog) 3 (*S. cerevisiae*) (SIRT3), transcript variant 1, mRNA (NCBI Accession No.: NM_012239.5).

SEQ ID NO: 4: *Homo sapiens* sirtuin 6 (SIRT6), transcript variant 1, mRNA (NCBI Accession No.: NM_016539).

SEQ ID NO: 5: Expanded natural antisense sequence (CV396200—expanded)

SEQ ID NO: 6: Natural Antisense sequence (CV428275)

SEQ ID NO: 7: Natural Antisense Sequence (BE717453)

SEQ ID NO: 8: Natural Antisense Sequence (AV718812)

SEQ ID NO: 9: Natural SIRT1 antisense sequence (AW169958)

SEQ ID NO: 10 Natural SIRT1 mouse antisense sequence (AK044604)

SEQ ID NO: 11: Natural SIRT3 antisense sequence (Hs.683117)

SEQ ID NO: 12: Natural SIRT3 antisense sequence (DA645474)

SEQ ID NO: 13: Natural SIRT6 antisense sequence (BF772662)

SEQ ID NO: 14: Natural SIRT6 antisense sequence (ANKRD24)

SEQ ID NOs: 15 to 94: Antisense oligonucleotides. * indicates phosphothioate bond, + indicates LNA and m indicates 2'O Me SEQ ID NO: 95 to 98-SEQ ID NO: 95 correspond to the exon 4 of the SIRT1 natural antisense CV396200, SEQ ID NO: 96, 97 and 98 correspond to the forward primer sequence, reverse primer sequence and the reporter sequence respectively.

SEQ ID NO: 99 corresponds to CUR 962, * indicates phosphothioate bond and + indicates LNA.

DETAILED DESCRIPTION

Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the ordering of acts or events, as some acts may occur in different orders and/or concurrently with other acts or events. Furthermore, not all illustrated acts or events are required to implement a methodology in accordance with the present invention.

All genes, gene names, and gene products disclosed herein are intended to correspond to homologs from any species for which the compositions and methods disclosed herein are applicable. Thus, the terms include, but are not limited to genes and gene products from humans and mice. It is understood that when a gene or gene product from a particular species is disclosed, this disclosure is intended to be exemplary only, and is not to be interpreted as a limitation unless the context in which it appears clearly indicates. Thus, for example, for the genes disclosed herein, which in some embodiments relate to mammalian nucleic acid and amino acid sequences are intended to encompass homologous and/or orthologous genes and gene products from other animals including, but not limited to other mammals, fish, amphibians, reptiles, and birds. In embodiments, the genes or nucleic acid sequences are human.

Definitions

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

As used herein, the term "mRNA" means the presently known mRNA transcript(s) of a targeted gene, and any further transcripts which may be elucidated.

By "antisense oligonucleotides" or "antisense compound" is meant an RNA or DNA molecule that binds to another RNA or DNA (target RNA, DNA). For example, if it is an RNA oligonucleotide it binds to another RNA target by means of RNA-RNA interactions and alters the activity of the target RNA. An antisense oligonucleotide can upregulate or downregulate expression and/or function of a particular polynucleotide. The definition is meant to include any foreign RNA or DNA molecule which is useful from a therapeutic, diagnostic, or other viewpoint. Such molecules include, for example, antisense RNA or DNA molecules, interference RNA (RNAi), micro RNA, decoy RNA molecules, siRNA, enzymatic RNA, therapeutic editing RNA and agonist and antagonist RNA, antisense oligomeric compounds, antisense oligonucleotides, external guide sequence (EGS) oligonucleotides, alternate splicers, primers, probes, and other oligomeric compounds that hybridize to at least a portion of the target nucleic acid. As such, these compounds may be introduced in the form of single-stranded, double-stranded, partially single-stranded, or circular oligomeric compounds.

In the context of this invention, the term "oligonucleotide" refers to an oligomer or polymer of ribonucleic acid (RNA) or deoxyribonucleic acid (DNA) or mimetics thereof. The term "oligonucleotide", also includes linear or circular oligomers of natural and/or modified monomers or linkages, including deoxyribonucleosides, ribonucleosides, substituted and alpha-anomeric forms thereof, peptide nucleic acids (PNA), locked nucleic acids (LNA), phosphorothioate, methylphosphonate, and the like. Oligonucleotides are capable of specifically binding to a target polynucleotide by way of a regular pattern of monomer-to-monomer interactions, such as Watson-Crick type of base pairing, Hoögsteen or reverse Hoögsteen types of base pairing, or the like.

The oligonucleotide may be "chimeric", that is, composed of different regions. In the context of this invention "chimeric" compounds are oligonucleotides, which contain two or more chemical regions, for example, DNA region(s), RNA region(s), PNA region(s) etc. Each chemical region is made up of at least one monomer unit, i.e., a nucleotide in the case of an oligonucleotides compound. These oligonucleotides typically comprise at least one region wherein the oligonucleotide is modified in order to exhibit one or more desired properties. The desired properties of the oligonucleotide include, but are not limited, for example, to increased resistance to nuclease degradation, increased cellular uptake, and/or increased binding affinity for the target nucleic acid. Different regions of the oligonucleotide may therefore have different properties. The chimeric oligonucleotides of the present invention can be formed as mixed structures of two or more oligonucleotides, modified oligonucleotides, oligonucleosides and/or oligonucleotide analogs as described above.

The oligonucleotide can be composed of regions that can be linked in "register" that is, when the monomers are linked consecutively, as in native DNA, or linked via spacers. The spacers are intended to constitute a covalent "bridge" between the regions and have in cases a length not exceeding about 100 carbon atoms. The spacers may carry different functionalities, for example, having positive or negative charge, carry special nucleic acid binding properties (intercalators, groove binders, toxins, fluorophors etc.), being lipophilic, inducing special secondary structures like, for example, alanine containing peptides that induce alpha-helices.

As used herein "Sirtuins (SIRT)s" are inclusive of all family members, mutants, alleles, fragments, species, coding and noncoding sequences, sense and antisense polynucleotide strands, etc.

As used herein, the words Sirtuin1, SIRT1, sirtuin, silent mating type information regulation 2 homolog 1, hSIR2, hSIRT1. NAD-dependent deacetylase sirtuin-1, SIR2L1, SIR2-like protein 1, are considered the same in the literature and are used interchangeably in the present application.

As used herein, the words 'Sirtuin 3', Sirtuin3, Sirtuin-3, SIRT3, SIRT-3, hSIRT3, NAD-dependent deacetylase sirtuin-3, mitochondrial, SIR2L3, SIR2-like protein 3 are used interchangeably in the present application.

As used herein, the words 'Sirtuin 6', Sirtuin6, Sirtuin-6, SIRT6, SIRT-6, NAD-dependent deacetylase sirtuin-6, SIR2L6, SIR2-like protein 6 are considered the same in the literature and are used interchangeably in the present application.

As used herein, the term "oligonucleotide specific for" or "oligonucleotide which targets" refers to an oligonucleotide having a sequence (i) capable of forming a stable complex with a portion of the targeted gene, or (ii) capable of forming a stable duplex with a portion of a mRNA transcript of the targeted gene. Stability of the complexes and duplexes can be determined by theoretical calculations and/or in vitro assays. Exemplary assays for determining stability of hybridization complexes and duplexes are described in the Examples below.

As used herein, the term "target nucleic acid" encompasses DNA, RNA (comprising premRNA and mRNA) transcribed from such DNA, and also cDNA derived from such RNA, coding, noncoding sequences, sense or antisense polynucleotides. The specific hybridization of an oligomeric compound with its target nucleic acid interferes with the normal function of the nucleic acid. This modulation of function of a target nucleic acid by compounds, which specifically hybridize to it, is generally referred to as "antisense". The functions of DNA to be interfered include, for example, replication and transcription. The functions of RNA to be interfered, include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of an encoded product or oligonucleotides.

RNA interference "RNAi" is mediated by double stranded RNA (dsRNA) molecules that have sequence-specific homology to their "target" nucleic acid sequences. In certain embodiments of the present invention, the mediators are 5-25 nucleotide "small interfering" RNA duplexes (siRNAs). The siRNAs are derived from the processing of dsRNA by an RNase enzyme known as Dicer. siRNA duplex products are recruited into a multi-protein siRNA complex termed RISC (RNA Induced Silencing Complex). Without wishing to be bound by any particular theory, a RISC is then believed to be guided to a target nucleic acid (suitably mRNA), where the siRNA duplex interacts in a sequence-specific way to mediate cleavage in a catalytic fashion. Small interfering RNAs that can be used in accordance with the present invention can be synthesized and used according to procedures that are well known in the art and that will be familiar to the ordinarily skilled artisan. Small interfering RNAs for use in the methods of the present invention suitably comprise between about 1 to about 50 nucleotides (nt). In examples of non limiting embodiments, siRNAs can comprise about 5 to about 40 nt, about 5 to about 30 nt, about 10 to 20 about 30 nt, about 15 to about 25 nt, or about 20-25 nucleotides.

Selection of appropriate oligonucleotides is facilitated by using computer programs that automatically align nucleic acid sequences and indicate regions of identity or homology. Such programs are used to compare nucleic acid sequences obtained, for example, by searching databases such as GenBank or by sequencing PCR products. Comparison of nucleic acid sequences from a range of species allows the selection of nucleic acid sequences that display an appropriate degree of identity between species. In the case of genes that have not been sequenced, Southern blots are performed to allow a determination of the degree of identity between genes in target species and other species. By performing Southern blots at varying degrees of stringency, as is well known in the art, it is possible to obtain an approximate measure of identity. These procedures allow the selection of oligonucleotides that exhibit a high degree of complementarity to target nucleic acid sequences in a subject to be controlled and a lower degree of complementarity to corresponding nucleic acid sequences in other species. One skilled in the art will realize that there is considerable latitude in selecting appropriate regions of genes for use in the present invention.

By "enzymatic RNA" is meant an RNA molecule with enzymatic activity. Enzymatic nucleic acids (ribozymes) act by first binding to a target RNA. Such binding occurs through the target binding portion of an enzymatic nucleic acid which is held in close proximity to an enzymatic portion of the molecule that acts to cleave the target RNA. Thus, the enzymatic nucleic acid first recognizes and then binds a target RNA through base pairing, and once bound to the correct site, acts enzymatically to cut the target RNA.

By "decoy RNA" is meant an RNA molecule that mimics the natural binding domain for a ligand. The decoy RNA therefore competes with natural binding target for the binding of a specific ligand. For example, it has been shown that over-expression of HIV trans-activation response (TAR) RNA can act as a "decoy" and efficiently binds HIV tat protein, thereby preventing it from binding to TAR sequences encoded in the HIV RNA. This is meant to be a specific example. Those in the art will recognize that this is but one example, and other embodiments can be readily generated using techniques generally known in the art.

As used herein, the term "monomers" typically indicates monomers linked by phosphodiester bonds or analogs thereof to form oligonucleotides ranging in size from a few monomeric units, e.g., from about 3-4, to about several hundreds of monomeric units. Analogs of phosphodiester linkages include: phosphorothioate, phosphorodithioate, methylphosphornates, phosphoroselenoate, phosphoramidate, and the like, as more fully described below.

The term "nucleotide" covers naturally occurring nucleotides as well as nonnaturally occurring nucleotides. It should be clear to the person skilled in the art that various nucleotides which previously have been considered "non-naturally occurring" have subsequently been found in nature. Thus, "nucleotides" includes not only the known purine and pyrimidine heterocycles-containing molecules, but also heterocyclic analogues and tautomers thereof. Illustrative examples of other types of nucleotides are molecules containing adenine, guanine, thymine, cytosine, uracil, purine, xanthine, diaminopurine, 8-oxo-N6-methyladenine, 7-deazaxanthine, 7-deazaguanine, N4,N4-ethanocytosin, N6,N6-ethano-2,6-diaminopurine, 5-methylcytosine, 5-(C3-C6)-alkynylcytosine, 5-fluorouracil, 5-bromouracil, pseudoisocytosine, 2-hydroxy-5-methyl-4-triazolopyridin, isocytosine, isoguanin, inosine and the "non-naturally occurring" nucleotides described in U.S. Pat. No. 5,432,272. The term "nucleotide" is intended to cover every and all of these examples as well as analogues and tautomers thereof. Especially interesting nucleotides are those containing adenine, guanine, thymine, cytosine, and uracil, which are considered as the naturally occurring nucleotides in relation to therapeutic and diagnostic application in humans. Nucleotides include the natural 2'-deoxy and 2'-hydroxyl sugars, e.g., as described in Komberg and Baker, DNA Replication, 2nd Ed. (Freeman, San Francisco, 1992) as well as their analogs.

"Analogs" in reference to nucleotides includes synthetic nucleotides having modified base moieties and/or modified sugar moieties. Such analogs include synthetic nucleotides designed to enhance binding properties, e.g., duplex or triplex stability, specificity, or the like.

As used herein, "hybridization" means the pairing of substantially complementary strands of oligomeric compounds. One mechanism of pairing involves hydrogen bonding, which may be Watson-Crick, Hoögsteen or reversed Hoögsteen hydrogen bonding, between complementary nucleoside or nucleotide bases (nucleotides) of the strands of oligomeric compounds. For example, adenine and thymine are complementary nucleotides which pair through the formation of hydrogen bonds. Hybridization can occur under varying circumstances.

An antisense compound is "specifically hybridizable" when binding of the compound to the target nucleic acid interferes with the normal function of the target nucleic acid to cause a modulation of function and/or activity, and there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

As used herein, the phrase "stringent hybridization conditions" or "stringent conditions" refers to conditions under which a compound of the invention will hybridize to its target sequence, but to a minimal number of other sequences. Stringent conditions are sequence-dependent and will be different in different circumstances and in the context of this invention. "stringent conditions" under which oligomeric compounds hybridize to a target sequence are determined by the nature and composition of the oligomeric compounds and the assays in which they are being investigated. In general, stringent hybridization conditions comprise low concentrations (<0.15M) of salts with inorganic cations such as Na++ or K++ (i.e., low ionic strength), temperature higher than 20° C.-25° C. below the Tm of the oligomeric compound:target sequence complex, and the presence of denaturants such as formamide, dimethylformamide, dimethyl sulfoxide, or the detergent sodium dodecyl sulfate (SDS). For example, the hybridization rate decreases 1.1% for each 1% formamide. An example of a high stringency hybridization condition is 0.1× sodium chloride-sodium citrate buffer (SSC)/0.1% (w/v) SDS at 60° C. for 30 minutes.

"Complementary," as used herein, refers to the capacity for precise pairing between two nucleotides on one or two oligomeric strands. For example, if a nucleobase at a certain position of an antisense compound is capable of hydrogen bonding with a nucleobase at a certain position of a target nucleic acid, said target nucleic acid being a DNA, RNA, or oligonucleotide molecule, then the position of hydrogen bonding between the oligonucleotide and the target nucleic acid is considered to be a complementary position. The oligomeric compound and the further DNA, RNA, or oligonucleotide molecule are complementary to each other when a sufficient number of complementary positions in each molecule are occupied by nucleotides which can hydrogen bond with each other. Thus, "specifically hybridizable" and "complementary" are terms which are used to indicate a sufficient degree of precise pairing or complementarity over a sufficient number of nucleotides such that stable and specific binding occurs between the oligomeric compound and a target nucleic acid.

It is understood in the an that the sequence of an oligomeric compound need not be 100% complementary to that of its target nucleic acid to be specifically hybridizable. Moreover, an oligonucleotide may hybridize over one or more segments such that intervening or adjacent segments are not involved in the hybridization event (e.g., a loop structure, mismatch or hairpin structure). The oligomeric compounds of the present invention comprise at least about 70%, or at least about 75%, or at least about 80%, or at least about 85%, or at least about 90%, or at least about 95%, or at least about 99% sequence complementarity to a target region within the target nucleic acid sequence to which they are targeted. For example, an antisense compound in which 18 of 20 nucleotides of the antisense compound are complementary to a target region, and would therefore specifically hybridize, would represent 90 percent complementarity. In this example, the remaining noncomplementary nucleotides may be clustered or interspersed with complementary nucleotides and need not be contiguous to each other or to complementary nucleotides. As such, an antisense compound which is 18 nucleotides in length having 4 (four) noncomplementary nucleotides which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art. Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (*Adv. Appl. Math.*, (1981) 2, 482-489).

As used herein, the term "Thermal Melting Point (Tm)" refers to the temperature, under defined ionic strength, pH, and nucleic acid concentration, at which 50% of the oligonucleotides complementary to the target sequence hybridize to the target sequence at equilibrium. Typically, stringent conditions will be those in which the salt concentration is at least about 0.01 to 1.0 M Na ion concentration (or other salts) at pH 7.0 to 8.3 and the temperature is at least about 30° C. for short oligonucleotides (e.g., 10 to 50 nucleotide). Stringent conditions may also be achieved with the addition of destabilizing agents such as formamide.

As used herein, "modulation" means either an increase (stimulation) or a decrease (inhibition) in the expression of a gene.

The term "variant," when used in the context of a polynucleotide sequence, may encompass a polynucleotide sequence related to a wild type gene. This definition may also include, for example, "allelic," "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. Of particular utility in the invention are variants of wild type gene products. Variants may result from at least one mutation in the nucleic acid sequence and may result in altered mRNAs or in polypeptides whose structure or function may or may not be altered. Any given natural or recombinant gene may have none, one, or many allelic forms. Common mutational changes that give rise to variants are generally ascribed to natural deletions, additions, or substitutions of nucleotides. Each of these types of changes may occur alone, or in combination with the others, one or more times in a given sequence.

The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs.) or single base mutations in which the polynucleotide sequence varies by one base. The presence of SNPs may be indicative of, for example, a certain population with a propensity for a disease state, that is susceptibility versus resistance.

Derivative polynucleotides include nucleic acids subjected to chemical modification, for example, replacement of hydrogen by an alkyl, acyl, or amino group. Derivatives, e.g., derivative oligonucleotides, may comprise non-naturally-occurring portions, such as altered sugar moieties or inter-sugar linkages. Exemplary among these are phosphorothioate and other sulfur containing species which are known in the art. Derivative nucleic acids may also contain labels, including radionucleotides, enzymes, fluorescent agents, chemiluminescent agents, chromogenic agents, substrates, cofactors, inhibitors, magnetic particles, and the like.

A "derivative" polypeptide or peptide is one that is modified, for example, by glycosylation, pegylation, phosphorylation, sulfation, reduction/alkylation, acylation, chemical coupling, or mild formalin treatment. A derivative may also be modified to contain a detectable label, either directly or indirectly, including, but not limited to, a radioisotope, fluorescent, and enzyme label.

As used herein, the term "animal" or "patient" is meant to include, for example, humans, sheep, elks, deer, mule deer, minks, mammals, monkeys, horses, cattle, pigs, goats, dogs, cats, rats, mice, birds, chicken, reptiles, fish, insects and arachnids.

"Mammal" covers warm blooded mammals that are typically under medical care (e.g., humans and domesticated animals). Examples include feline, canine, equine, bovine, and human, as well as just human.

"Treating" or "treatment" covers the treatment of a disease-state in a mammal, and includes: (a) preventing the disease-state from occurring in a mammal, in particular, when such mammal is predisposed to the disease-state but has not yet been diagnosed as having it; (b) inhibiting the disease-state, e.g., arresting it development; and/or (c) relieving the disease-state, e.g., causing regression of the disease state until a desired endpoint is reached. Treating also includes the amelioration of a symptom of a disease (e.g., lessen the pain or discomfort), wherein such amelioration may or may not be directly affecting the disease (e.g., cause, transmission, expression, etc.).

As used herein, "cancer" refers to all types of cancer or neoplasm or malignant tumors found in mammals, including, but not limited to: leukemias, lymphomas, melanomas, carcinomas and sarcomas. The cancer manifests itself as a "tumor" or tissue comprising malignant cells of the cancer. Examples of tumors include sarcomas and carcinomas such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma. Additional cancers which can be treated by the disclosed composition according to the invention include but not limited to, for example, Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, cervical cancer, endometrial cancer, adrenal cortical cancer, and prostate cancer.

"Neurological disease or disorder" refers to any disease or disorder of the nervous system and/or visual system. "Neurological disease or disorder" include disease or disorders that involve the central nervous system (brain, brainstem and cerebellum), the peripheral nervous system (including cranial nerves), and the autonomic nervous system (parts of which are located in both central and peripheral nervous system). Examples of neurological disorders include but are not limited to, headache, stupor and coma, dementia, seizure, sleep disorders, trauma, infections, neoplasms, neuroopthalmology, movement disorders, demyelinating diseases, spinal cord disorders, and disorders of peripheral nerves, muscle and neuromuscular junctions. Addiction and mental illness, include, but are not limited to, bipolar disorder and schizophrenia, are also included in the definition of neurological disorder. The following is a list of several neurological disorders, symptoms, signs and syndromes that can be treated using compositions and methods according to the present invention: acquired epileptiform aphasia; acute disseminated encephalomyelitis; adrenoleukodystrophy; age-related macular degeneration; agenesis of the corpus callosum; agnosia; Aicardi syndrome; Alexander disease; Alpers' disease; alternating hemiplegia; Vascular dementia; amyotrophic lateral sclerosis; anencephaly; Angelman syndrome; angiomatosis; anoxia; aphasia; apraxia; arachnoid cysts; arachnoiditis; Anronl-Chiari malformation; arteriovenous malformation; Asperger syndrome; ataxia telegiectasia; attention deficit hyperactivity disorder autism; autonomic dysfunction; back pain; Batten disease; Behcet's disease; Bell's palsy; benign essential blepharospasm benign focal; amyotrophy; benign intracranial hypertension; Binswanger's disease; blepharospasm; Bloch Sulzberger syndrome; brachial plexus injury; brain abscess; brain injury; brain tumors (including glioblastoma multiforme); spinal tumor; Brown-Sequard syndrome; Canavan disease; carpal tunnel syndrome; causalgia; central pain syndrome; central pontine myelinolysis; cephalic disorder; cerebral aneurysm; cerebral arteriosclerosis; cerebral atrophy; cerebral gigantism; cerebral palsy; Charcot-Marie-Tooth disease; chemotherapy-induced neuropathy and neuropathic pain; Chiari malformation; chorea; chronic inflammatory demyelinating polyneuropathy; chronic pain; chronic regional pain syndrome; Coffin Lowry syndrome; coma, including persistent vegetative state; congenital facial diplegia; corticobasal degeneration; cranial arteritis; craniosynostosis; Creutzfeldt-Jakob disease; cumulative trauma disorders; Cushing's syndrome; cytomegalic inclusion body disease; cytomegalovirus infection; dancing eyes-dancing feet syndrome; Dandy Walker syndrome; Dawson disease, De Morsier's syndrome; Dejerine-Klumke palsy; dementia; dermatomyositis; diabetic neuropathy; diffuse sclerosis; dysautonomia; dysgraphia; dyslexia; dystonias; early infantile epileptic encephalopathy; empty sella syndrome; encephalitis; encephaloceles; encephalotrigeminal angiomatosis; epilepsy; Erb's palsy; essential tremor, Fabry's disease; Fahr's syndrome; fainting; familial spastic paralysis; febrile seizures; Fisher syndrome; Friedreich's ataxia; fronto-temporal dementia and other "tauopathies"; Gaucher's disease; Gerstmann's syndrome; giant cell arteritis; giant cell inclusion disease, globoid cell leukodystrophy; Guillain-Barre syndrome; HTLV-1-associated myelopathy; Hallervorden-Spatz disease; head injury; headache; hemifacial spasm; hereditary spastic paraplegia; heredopathia atactic a polyneuritiformis; herpes zoster oticus; herpes zoster; Hirayama syndrome; HIVassociated dementia and neuropathy (also neurological manifestations of AIDS); holoprosencephaly; Huntington's disease and other polyglutamine repeat diseases; hydranencephaly; hydrocephalus; hypercortisolism; hypoxia; immune-mediated encephalomyelitis; inclusion body myositis; incontinentia pigmenti; infantile phytanic acid storage disease; infantile refsum disease; infantile spasms; inflammatory myopathy; intracranial cyst; intracranial hypertension; Joubert syndrome; Kearns-Sayre syndrome; Kennedy disease Kinsbourne syndrome; Klippel Feil syndrome; Krabbe disease; Kugelberg-Welander disease; kuru; Lafora disease; Lambert-Eaton myasthenic syndrome; Landau-Kleffner syndrome; lateral medullary (Wallenberg) syndrome; learning disabilities; Leigh's disease; Lennox-Gustaut syndrome; Lesch-Nyhan syndrome; leukodystrophy; Lewy body dementia; Lissencephaly; locked-in syndrome; Lou Gehrig's disease (i.e., motor neuron disease or amyotrophic lateral sclerosis); lumbar disc disease; Lyme disease-neurological sequelae; Machado-Joseph disease; macrencephaly; megalencephaly; Melkersson-Rosenthal syndrome; Menicres disease; meningitis; Menkes disease; metachromatic leukodystrophy; microcephaly; migraine; Miller Fisher syndrome; mini-strokes; mitochondrial myopathies; Mobius syndrome; monomelic amyotrophy; motor neuron disease; Moyamoya disease; mucopolysaccharidoses milti-infarct dementia; multifocal motor neuropathy; multiple sclerosis and other demyelinating disorders; multiple system atrophy with postural hypotension; p muscular dystrophy; myasthenia gravis; myelinoclastic diffuse sclerosis; myoclonic encephalopathy of infants; myoclonus; myopathy; myotonia congenital; narcolepsy; neuofibromatosis; neuroleptic malignant syndrome; neurological manifestations of AIDS; neurological sequelae oflupus; neuromyotonia; neuronal ceroid lipofuscinosis; neuronal migration disorders; Niemann-Pick disease; O'Sullivan-McLeod syndrome; occipital neuralgia; occult spinal dysraphism sequence; Ohtahara syndrome; olivopontocerebellar atrophy; opsoclonus myoclonus; optic neuritis; orthostatic hypotension; overuse syndrome; paresthesia; Neurodegenerative disease or disorder (Parkinson's disease, Huntington's disease, Alzheimer's disease, amyotrophic lateral sclerosis (ALS), dementia, multiple sclerosis and other diseases and disorders associated with neuronal cell death); paramyotonia congenital; paraneoplastic diseases; paroxysmal attacks; Parry Romberg syndrome; Pelizaeus-Merzbacher disease; periodic paralyses; peripheral neuropathy; painful neuropathy and neuropathic pain; persistent vegetative state; pervasive developmental disorders; photic sneeze reflex; phytanic acid storage disease; Pick's disease; pinched nerve; pituitary tumors; polymyositis; porencephaly; post-polio syndrome; postherpetic neuralgia; postinfectious encephalomyelitis; postural hypotension; Prader-Willi syndrome; primary lateral sclerosis; prion diseases; progressive hemifacial atrophy; progressive multifocalleukoencephalopathy; progressive sclerosing poliodystrophy; progressive supranuclear palsy; pseudotumor cerebri; Ramsay-Hunt syndrome (types I and II); Rasmussen's encephalitis; reflex sympathetic dystrophy syndrome; Refsum disease; repetitive motion disorders; repetitive stress injuries; restless legs syndrome; retrovirus-associated myelopathy; Rett syndrome; Reye's syndrome; Saint Vitus dance; Sandhoff disease; Schilder's disease; schizencephaly; septo-optic dysplasia; shaken baby syndrome; shingles; Shy-Drager syndrome; Sjogren's syndrome; sleep apnea; Soto's syndrome; spasticity; spina bifida; spinal cord injury; spinal cord tumors; spinal muscular atrophy; Stiff-Person syndrome; stroke; Sturge-Weber syndrome; subacute sclerosing panercephalitis; subcortical arteriosclerotic encephalopathy; Sydenham chorea; syncope; syringomyelia; tardive dyskinesia; Tay-Sachs disease; temporal arteritis; tethered spinal cord syndrome; Thomsen disease; thoracic outlet syndrome; Tic Douloureux; Todd's paralysis; Tourette syndrome; transient ischemic attack; transmissible spongiform encephalopathies; transverse myelitis; traumatic brain injury; tremor; trigeminal neuralgia; tropical spastic paraparesis; tuberous sclerosis; vascular dementia (multi-infarct dementia); vasculitis including temporal arteritis; Von Hippel-Lindau disease; Wallenberg's syndrome; Werdnig-Hoffman disease; West syndrome; whiplash; Williams syndrome, Wildon's disease; and Zelweger syndrome.

"Metabolic disease" refers to a wide range of diseases and disorders of the endocrine system including, for example, insulin resistance, diabetes, obesity, impaired glucose tolerance, high blood cholesterol, hyperglycemia, dyslipidemia and hyperlipidemia.

An "Inflammation" refers to systemic inflammatory conditions and conditions associated locally with migration and attraction of monocytes, leukocytes and/or neutrophils. Examples of inflammation include, but are not limited to, Inflammation resulting from infection with pathogenic organisms (including gram-positive bacteria, gram-negative bacteria, viruses, fungi, and parasites such as protozoa and helminths), transplant rejection (including rejection of solid organs such as kidney, liver, heart, lung or cornea, as well as rejection of bone marrow transplants including graft-versus-host disease (GVHD)), or from localized chronic or acute autoimmune or allergic reactions. Autoimmune diseases include acute glomerulonephritis; rheumatoid or reactive arthritis; chronic glomerulonephritis; inflammatory bowel diseases such as Crohn's disease, ulcerative colitis and necrotizing enterocolitis; granulocyte transfusion associated syndromes; inflammatory dermatoses such as contact dermatitis, atopic dermatitis, psoriasis; systemic lupus erythematosus (SLE), autoimmune thyroiditis, multiple sclerosis, and some forms of diabetes, or any other autoimmune state where attack by the subject's own immune system results in pathologic tissue destruction. Allergic reactions include allergic asthma, chronic bronchitis, acute and delayed hypersensitivity. Systemic inflammatory disease states include inflammation associated with trauma, burns, reperfusion following ischemic events (e.g. thrombotic events in heart, brain, intestines or peripheral vasculature, including myocardial infarction and stroke), sepsis. ARDS or multiple organ dysfunction syndrome. Inflammatory cell recruitment also occurs in atherosclerotic plaques. Inflammation includes, but is not limited to, Non-Hodgkin's lymphoma, Wegener's granulomatosis, Hashimoto's thyroiditis, hepatocellular carcinoma, thymus atrophy, chronic pancreatitis, rheumatoid arthritis, reactive lymphoid hyperplasia, osteoarthritis, ulcerative colitis, papillary carcinoma, Crohn's disease, ulcerative colitis, acute cholecystitis, chronic cholecystitis, cirrhosis, chronic sialadenitis, peritonitis, acute pancreatitis, chronic pancreatitis, chronic Gastritis, adenomyosis, endometriosis, acute cervicitis, chronic cervicitis, lymphoid hyperplasia, multiple sclerosis, hypertrophy secondary to idiopathic thrombocytopenic purpura, primary IgA nephropathy, systemic lupus erythematosus, psoriasis, pulmonary emphysema, chronic pyelonephritis, and chronic cystitis.

A cardiovascular disease or disorder includes those disorders that can either cause ischemia or are caused by reperfusion of the heart. Examples include, but are not limited to, atherosclerosis, coronary artery disease, granulomatous myocarditis, chronic myocarditis (non-granulomatous), primary hypertrophic cardiomyopathy, peripheral artery disease (PAD), stroke, angina pectoris, myocardial infarction, cardiovascular tissue damage caused by cardiac arrest, cardiovascular tissue damage caused by cardiac bypass, cardiogenic shock, and related conditions that would be known by those of ordinary skill in the art or which involve dysfunction of or tissue damage to the heart or vasculature, especially, but not limited to, tissue damage related to Sirtuin3 activation. CVS diseases include, but are not limited to, atherosclerosis, granulomatous myocarditis, myocardial infarction, myocardial fibrosis secondary to valvular heart disease, myocardial fibrosis without infarction, primary hypertrophic cardiomyopathy, and chronic myocarditis (non-granulomatous).

Polynucleotide and Oligonucleotide Compositions and Molecules

Targets

In one embodiment, the targets comprise nucleic acid sequences of a Sirtuin (SIRT), including without limitation sense and/or antisense noncoding and/or coding sequences associated with a Sirtuin (SIRT).

In one embodiment, the targets comprise nucleic acid sequences of SIRT1, including without limitation sense and/or antisense noncoding and/or coding sequences associated with SIRT1 gene.

In one embodiment, the targets comprise nucleic acid sequences of SIRT3, including without limitation sense and/or antisense noncoding and/or coding sequences associated with SIRT3 gene.

In one embodiment, the targets comprise nucleic acid sequences of SIRT6, including without limitation sense and/or antisense noncoding and/or coding sequences associated with SIRT6 gene.

"SIRT1 protein" refers to a member of the sir2 family of sirtuin deacetylases. In one embodiment, a SIRT1 protein includes yeast Sir2 (GenBank Accession No. P53685), *C. elegans* Sir-2.1 (GenBank Accession No. NP.sub.-501912), human SIRT1 (GenBank Accession No. NM.sub.-012238 and NP.sub.-036370 (or AF083106))

SIRT1 "Sirtuins" are proteins that include a SIR2 domain, a domain defined as amino acids sequences that are scored as hits in the Pfam family "SIR2"-PF02146 (attached to the Appendix). This family is referenced in the INTERPRO database as INTERPRO description (entry IPR003000). To identify the presence of a "SIR2" domain in a protein sequence, and make the determination that a polypeptide or protein of interest has a particular profile, the amino acid sequence of the protein can be searched against the Pfam database of HMMs (e.g., the Pfam database, release 9) using the default parameters (http://www.sanger.ac.uk/Software/Pfam/HMM_search). The SIR2 domain is indexed in Pfam as PF02146 and in INTERPRO as INTERPRO description (entry IPR003000). A description of the Pfam database can be found in "The Pfam Protein Families Database" Bateman A et al. (2002) Nucleic Acids Research 30(1):276-280 and Sonhammer et al. (1997) Proteins 28(3):405-420 and a detailed description of HMMs can be found, for example, in Gribskov et al. (1990) Meth. Enzymol. 183:146-159; Gribskov et al. (1987) Proc. Natl. Acad. Sci. USA 84:4355-4358; Krogh et al. (1994) J. Mol. Biol. 235:1501-1531; and Stultz et al. (1993) Protein Sci. 2:305-314.

Among the mitochondrial sirtuins, SIRT3 possesses the most robust deacetylase activity. Indeed, significantly higher levels of mitochondrial protein acetylation were detected in the livers of SIRT3-null mice, compared to those of SIRT4 or SIRT5 knockout animals. However, little is known about the physiological role of SIRT3 despite the fact that a number of SIRT3 substrates and co-precipitating proteins have been identified: acetyl-CoA synthetase 2, Ku70, FOXO3a, subunit 9 of mitochondrial Complex I (NDUFA9), glutamate dehydrogenase and isocitrate dehydrogenase 2.

SIRT3 is a major mitochondrial deacetylase. Mitochondrial proteins show hyperacetylation in SIRT3 knockout mice, but not in SIRT4 or SIRT5 knockout mice. Acetyl-CoA synthetase 2 (AceCS2), a mitochondrial enzyme that converts acetate into acetyl-CoA, was the first mitochondrial substrate of SIRT3 identified. Deacetylation of AceCS2 at lysine 642 by SIRT3 activates acetyl-CoA synthetase activity, providing increased acetyl-CoA to feed into the tricarboxylic acid cycle. Glutamate dehydrogenase (GDH), another mitochondrial protein involved in energy production, is deacetylated by SIRT3. GDH can also be ADP-ribosylated by SIRT4 in turn to decrease its enzyme activity. This indicates that SIRT3 could play an important role in cell metabolism. SIRT3 has also been shown to be involved in selective apoptosis pathways and cell growth control. SIRT3 and SIRT4, but not SIRT5, have been implicated in the NAD+ salvage pathway that regulates the NAD+ level relating to cell survival. In addition, variability in the hSIRT3 gene has been linked to human longevity.

The Silent Information Regulator-2 gene (Sir2) encodes an NAD-dependent histone deacetylase that links regulation of chromatin, genomic stability, and life span in *S. cerevisiae*. By promoting chromatin silencing, Sir2 inhibits transcription at several genetic loci and represses recombination at ribosomal DNA (rDNA) repeats. Yeast with mutations in Sir2 have increased genomic instability in the context of rDNA recombination, which in turn shortens replicative life span—a marker of reproductive aging in this organism. Conversely, extracopies of Sir2 that suppress rDNA recombination increase replicative life span. These effects of Sir2 suggest paradigms in which genes that promote genome stabilization through chromatin modulation may be important contributors to regulation of organismal life span, aging, and age-related pathology.

Consistent with a conserved role for Sir2 factors in life span regulation, increased activity of Sir2 proteins in the multicellular organisms *C. elegans* and *D. melanogaster* also increases life span. However, these Sir2 factors may operate through mechanisms that are independent of genome stabilization, and their physiologic molecular substrates are still unclear. In mammals, there are seven Sir2 family members, SIRT1-SIRT7. The SIRTs have been of great interest as candidate regulators of mammalian life span and aging-related processes. In this context, several mammalian SIRTs have functions that impact on aging-associated molecular pathways and disease. However, initial studies of mammalian SIRTs linked these enzymes to biochemical targets and cellular functions that are distinct from those of *S. cerevisiae* Sir2.

The generation of mice deficient for the mammalian SIRT6 gene revealed a potential role for SIRT6 in linking regulation of life span, chromatin, and genomic stability. In this context, SIRT6 deficiency in mice leads to dramatically shortened life span and acute degenerative phenotypes that overlap with pathologies of premature aging. Moreover, SIRT6 knockout mouse cells have genomic instability and DNA damage hypersensitivity. In biochemical fractionation assays, SIRT6 protein associates preferentially with a chromatin-enriched cellular fraction. Together, these observations suggested that SIRT6 might couple chromatin regulation with DNA repair. However, a physiologic role for SIRT6 in such a process has not yet been demonstrated.

In some embodiments, antisense oligonucleotides are used to prevent or treat diseases or disorders associated with Sirtuin (SIRT) family members. Exemplary Sirtuin (SIRT) mediated diseases and disorders which can be treated with cell/tissues regenerated from stem cells obtained using the antisense compounds comprise: cancer (e.g., breast cancer, colorectal cancer, CCL, CML, prostate cancer), a neurodegenerative disease or disorder (e.g., Alzheimer's Disease (AD), Huntington's disease, Parkinson's disease, Amyotrophic Lateral Sclerosis (ALS), Multiple Sclerosis, and disorders caused by polyglutamine aggregation); skeletal muscle disease (e.g., Duchene muscular dystrophy, skeletal muscle atrophy, Becker's dystrophy, or myotonic dystrophy); a metabolic disease or disorder (e.g., insulin resistance, diabetes, type 2 diabetes, obesity, impaired glucose tolerance, metabolic syndrome, adult-onset diabetes, diabetic nephropathy, hyperglycemia, diabetic nephropathy, Hypercholesterolemia, dyslipidemia hyperlipidemia and an age-related metabolic disease etc.), a disease or disorder associated with impaired regulation of insulin level, neuropathy (e.g. sensory neuropathy, autonomic neuropathy, motor neuropathy, retinopathy), a disease or disorder associated with a ketogenic condition, a disease or disorder associated with impaired energy homeostasis, a disease or disorder associated with impaired Acetyl-CoA synthetase 2 activity, a disease or disorder associated with metabolic homeostasis, a lipid metabolism disease or disorder, a disease or disorder associated with impaired thermogenesis, a disease or disorder associated with mitochondrial dysfunction, neuropathy (e.g., sensory neuropathy, autonomic neuropathy, motor neuropathy, retinopathy), a liver disease (e.g., due to alcohol abuse or hepatitis, fatty liver disease etc.); age-related macular degeneration, bone disease (e.g., osteoporosis), a blood disease (e.g., a leukemia); liver disease (e.g., due to alcohol abuse or hepatitis); obesity; bone resorption, age-related macular degeneration, AIDS related dementia, ALS, Bell's Palsy, atherosclerosis, a cardiac disease (e.g., cardiac dysrhymias, chronic congestive heart failure, ischemic stroke, coronary artery disease and cardiomyopathy), chronically degenerative disease (e.g., cardiac muscle disease), chronic renal failure, type 2 diabetes, ulceration, cataract, presbiopia, glomerulonephritis, Guillan-Barre syndrome, hemorrhagic stroke, rheumatoid arthritis, inflammatory bowel disease, SLE, Crohn's disease, osteoarthritis, osteoporosis, Chronic Obstructive Pulmonary Disease (COPD), pneumonia, skin aging, urinary incontinence, a disease or disorder associated with mitochondrial dysfunction (e.g., mitochondrial myopathy, encephalopathy, Leber's disease, Leigh encephalopathia, Pearson's disease, lactic acidosis, mitochondrial encephalopathy, lactic acidosis and stroke like symptoms' (MELAS) etc.) and a disease or disorder associated with neuronal cell death, degenerative syndrome, aging, a disease or disorder associated with telomere dysfunction, a disease or disorder associated with impaired chromatin regulation, a disease or disorder associated with premature cellular senescence, a disease or disorder associated with impaired SIRT6 mediated DNA repair and a condition characterized by unwanted cell loss.

In another embodiment, the antisense oligonucleotides modulate the normal expression and/or normal function of a Sirtuin (SIRT) in patients suffering from or at risk of developing diseases or disorders associated with Sirtuin (SIRT).

In embodiments of the present invention, therapeutic and/or cosmetic regimes and related tailored treatments are provided to subjects requiring skin treatments or at risk of developing conditions for which they would require skin treatments. Diagnosis can be made, e.g., based on the subject's SIRT status. A patient's SIRT expression levels in a given tissue such as skin can be determined by methods known to those of skill in the art and described elsewhere herein, e.g., by analyzing tissue using PCR or antibody-based detection methods.

A preferred embodiment of the present invention provides a composition for skin treatment and/or a cosmetic application comprising SIRT antisense oligonucleotides, e.g., to upregulate expression of SIRT in the skin. Examples of antisense oligonucleotides are set forth as SEQ ID NOS: 4 to 16. U.S. Pat. No. 7,544,497, "Compositions for manipulating the lifespan and stress response of cells and organisms," incorporated herein by reference, describes potential cosmetic use for agents that modulate Sirtuin activity by reducing the K, of the Sirtuin protein for its substrate. In embodiments, cells are treated in vivo with the oligonucleotides of the present invention, to increase cell lifespan or prevent apoptosis. For example, skin can be protected from aging, e.g., developing wrinkles, by treating skin, e.g., epithelial cells, as described herein. In an exemplary embodiment, skin is contacted with a pharmaceutical or cosmetic composition comprising a SIRT antisense compound as described herein. Exemplary skin afflictions or skin conditions include disorders or diseases associated with or caused by inflammation, sun damage or natural aging. For example, the compositions find utility in the prevention or treatment of contact dermatitis (including irritant contact dermatitis and allergic contact dermatitis), atopic dermatitis (also known as allergic eczema), actinic keratosis, keratinization disorders (including eczema), epidermolysis bullosa diseases (including penfigus), exfoliative dermatitis, seborrheic dermatitis, erythemas (including erythema multiforme and erythema nodosum), damage caused by the sun or other light sources, discoid lupus erythematosus, dermatomyositis, skin cancer and the effects of natural aging.

Sirtuin has been reported to interfere with dihydrotestosterone-induced androgen receptor signaling. (See, e.g., Fu, et al., 2006, "Hormonal Control of Androgen Receptor Function through SIRT1," Molecular and Cellular Biology 26(21): 8122-8135, incorporated herein by reference.) In embodiments of the present invention, a composition comprising SIRT antisense oligonucleotides, e.g., to upregulate expression of SIRT in the scalp and inhibit androgen receptor signaling, thereby preventing androgenetic alopecia (hair loss). In embodiments, a patient suffering from alopecia is administered either a topical or systemic formulation.

In an embodiment, an antisense oligonucleotide described herein is incorporated into a topical formulation containing a topical carrier that is generally suited to topical drug administration and comprising any such material known in the art. The topical carrier may be selected so as to provide the composition in the desired form, e.g., as an ointment, lotion, cream, microemulsion, gel, oil, solution, or the like, and may be comprised of a material of either naturally occurring or synthetic origin. It is preferable that the selected carrier not adversely affect the active agent or other components of the topical formulation. Examples of suitable topical carriers for use herein include water, alcohols and other nontoxic organic solvents, glycerin, mineral oil, silicone, petroleum jelly, lanolin, fatty acids, vegetable oils, parabens, waxes, and the like. Formulations may be colorless, odorless ointments, lotions, creams, microemulsions and gels.

Antisense oligonucleotides of the invention may be incorporated into ointments, which generally are semisolid preparations which are typically based on petrolatum or other petroleum derivatives. The specific ointment base to be used, as will be appreciated by those skilled in the art, is one that will provide for optimum drug delivery, and, preferably, will provide for other desired characteristics as well, e.g., emolliency or the like. As with other carriers or vehicles, an ointment base should be inert, stable, nonirritating and nonsensitizing. As explained in Remington's Pharmaceutical Sciences (Mack Pub. Co.), ointment bases may be grouped into four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Exemplary water-soluble ointment bases are prepared from polyethylene glycols (PEGs) of varying molecular weight (see, e.g., Remington's, supra).

Antisense oligonucleotides of the invention may be incorporated into lotions, which generally are preparations to be applied to the skin surface without friction, and are typically liquid or semiliquid preparations in which solid particles, including the active agent, are present in a water or alcohol base. Lotions are usually suspensions of solids, and may comprise a liquid oily emulsion of the oil-in-water type. Lotions are preferred formulations for treating large body areas, because of the ease of applying a more fluid composition. It is generally necessary that the insoluble matter in a lotion be finely divided. Lotions will typically contain suspending agents to produce better dispersions as well as compounds useful for localizing and holding the active agent in contact with the skin, e.g., methylcellulose, sodium carboxymethylcellulose, or the like. An exemplary lotion formulation for use in conjunction with the present method contains propylene glycol mixed with a hydrophilic petrolatum such as that which may be obtained under the trademark Aquaphor.sup.® from Beiersdorf, Inc. (Norwalk, Conn.).

Antisense oligonucleotides of the invention may be incorporated into creams, which generally are viscous liquid or semisolid emulsions, either oil-in-water or water-in-oil. Cream bases are water-washable, and contain an oil phase, an emulsifier and an aqueous phase. The oil phase is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation, as explained in Remington's, supra, is generally a nonionic, anionic, cationic or amphoteric surfactant.

Antisense oligonucleotides of the invention may be incorporated into microemulsions, which generally are thermodynamically stable, isotropically clear dispersions of two immiscible liquids, such as oil and water, stabilized by an interfacial film of surfactant molecules (Encyclopedia of Pharmaceutical Technology (New York: Marcel Dekker, 1992), volume 9). For the preparation of microemulsions, surfactant (emulsifier), co-surfactant (co-emulsifier), an oil phase and a water phase are necessary. Suitable surfactants include any surfactants that are useful in the preparation of emulsions, e.g., emulsifiers that are typically used in the preparation of creams. The co-surfactant (or "co-emulsifer") is generally selected from the group of polyglycerol derivatives, glycerol derivatives and fatty alcohols. Preferred emulsifier/co-emulsifier combinations are generally although not necessarily selected from the group consisting of glyceryl monostearate and polyoxyethylene stearate; polyethylene glycol and ethylene glycol palmitostearate; and caprilic and capric triglycerides and oleoyl macrogolglycerides. The water phase includes not only water but also, typically, buffers, glucose, propylene glycol, polyethylene glycols, preferably lower molecular weight polyethylene glycols (e.g., PEG 300 and PEG 400), and/or glycerol, and the like, while the oil phase will generally comprise, for example, fatty acid esters, modified vegetable oils, silicone oils, mixtures of mono- di- and triglycerides, mono- and di-esters of PEG (e.g., oleoyl macrogol glycerides), etc.

Antisense oligonucleotides of the invention may be incorporated into gel formulations, which generally are semisolid systems consisting of either suspensions made up of small inorganic particles (two-phase systems) or large organic molecules distributed substantially uniformly throughout a carrier liquid (single phase gels). Single phase gels can be made, for example, by combining the active agent, a carrier liquid and a suitable gelling agent such as tragacanth (at 2 to 5%), sodium alginate (at 2-10%), gelatin (at 2-15%), methylcellulose (at 3-5%), sodium carboxymethylcellulose (at 2-5%), carbomer (at 0.3-5%) or polyvinyl alcohol (at 10-20%) together and mixing until a characteristic semisolid product is produced. Other suitable gelling agents include methylhydroxycellulose, polyoxyethylene-polyoxypropylene, hydroxyethylcellulose and gelatin. Although gels commonly employ aqueous carrier liquid, alcohols and oils can be used as the carrier liquid as well.

Various additives, known to those skilled in the art, may be included in formulations, e.g., topical formulations. Examples of additives include, but are not limited to, solubilizes, skin permeation enhancers, opacifiers, preservatives (e.g., anti-oxidants), gelling agents, buffering agents, surfactants (particularly nonionic and amphoteric surfactants), emulsifiers, emollients, thickening agents, stabilizers, humectants, colorants, fragrance, and the like. Inclusion of solubilizers and/or skin permeation enhancers is particularly preferred, along with emulsifiers, emollients and preservatives. An optimum topical formulation comprises approximately: 2 wt. % to 60 wt. %, preferably 2 wt. % to 50 wt. %, solubilizer and/or skin permeation enhancer; 2 wt. % to 50 wt. %, preferably 2 wt. % to 20 wt. %, emulsifiers; 2 wt. % to 20 wt. % emollient; and 0.01 to 0.2 wt. % preservative, with the active agent and carrier (e.g., water) making of the remainder of the formulation.

A skin permeation enhancer serves to facilitate passage of therapeutic levels of active agent to pass through a reasonably sized area of unbroken skin. Suitable enhancers are well known in the art and include, for example: lower alkanols such as methanol ethanol and 2-propanol; alkyl methyl sulfoxides such as dimethylsulfoxide (DMSO), decylmethylsulfoxide (C.sub.10 MSO) and tetradecylmethyl sulfoxide; pyrrolidones such as 2-pyrrolidone, N-methyl-2-pyrrolidone and N-(-hydroxyethyl)pyrrolidone; urea; N,N-diethyl-m-toluamide; C.sub.2-C.sub.6 alkanediols; miscellaneous solvents such as dimethyl formamide (DMF), N,N-dimethylacetamide (DMA) and tetrahydrofurfuryl alcohol; and the 1-substituted azacycloheptan-2-ones, particularly 1-n-dodceylcyclazacycloheptan-2-one (laurocapram; available under the trademark Azone.sup.® from Whitby Research Incorporated, Richmond, Va.).

Examples of solubilizers include, but are not limited to, the following: hydrophilic ethers such as diethylene glycol monoethyl ether (ethoxydiglycol, available commercially as Transcutol.sup.®) and diethylene glycol monoethyl ether oleate (available commercially as Soficutol.sup.®); polyethylene castor oil derivatives such as polyoxy 35 castor oil, polyoxy 40 hydrogenated castor oil, etc.; polyethylene glycol, particularly lower molecular weight polyethylene glycols such as PEG 300 and PEG 400, and polyethylene glycol derivatives such as PEG-8 caprylic/capric glycerides (available commercially as Labrasol.sup.®); alkyl methyl sulfoxides such as DMSO; pyrrolidones such as 2-pyrrolidone and N-methyl-2-pyrrolidone; and DMA. Many solubilizers can also act as absorption enhancers. A single solubilizer may be incorporated into the formulation, or a mixture of solubilizers may be incorporated therein.

Suitable emulsifiers and co-emulsifiers include, without limitation, those emulsifiers and co-emulsifiers described with respect to microemulsion formulations. Emollients include, for example, propylene glycol, glycerol, isopropyl myristate, polypropylene glycol-2 (PPG-2) myristyl ether propionate, and the like.

Other active agents may also be included in formulations, e.g., other anti-inflammatory agents, analgesics, antimicrobial agents, antifungal agents, antibiotics, vitamins, antioxidants, and sunblock agents commonly found in sunscreen formulations including, but not limited to, anthranilates, benzophenones (particularly benzophenone-3), camphor derivatives, cinnamates (e.g., octyl methoxycinnamate), dibenzoyl methanes (e.g., butyl methoxydibenzoyl methane), p-aminobenzoic acid (PABA) and derivatives thereof, and salicylates (e.g., octyl salicylate).

In one embodiment, the oligonucleotides are specific for polynucleotides of a Sirtuin (SIRT), which includes, without limitation noncoding regions. The Sirtuin (SIRT) targets comprise variants of a Sirtuin (SIRT); mutants of a Sirtuin (SIRT), including SNPs; noncoding sequences of a Sirtuin (SIRT); alleles, fragments and the like. Preferably the oligonucleotide is an antisense RNA molecule.

In accordance with embodiments of the invention, the target nucleic acid molecule is not limited to a Sirtuin (SIRT) polynucleotides alone but extends to any of the isoforms, receptors, homologs, non-coding regions and the like of a Sirtuin (SIRT).

In another embodiment, an oligonucleotide targets a natural antisense sequence (natural antisense to the coding and non-coding regions) of a Sirtuin (SIRT) targets, including, without limitation, variants, alleles, homologs, mutants, derivatives, fragments and complementary sequences thereto. Preferably the oligonucleotide is an antisense RNA or DNA molecule.

In another embodiment, the oligomeric compounds of the present invention also include variants in which a different base is present at one or more of the nucleotide positions in the compound. For example, if the first nucleotide is an adenine, variants may be produced which contain thymidine, guanosine, cytidine or other natural or unnatural nucleotides at this position. This may be done at any of the positions of the antisense compound.

In some embodiments, homology, sequence identity or complementarity, between the antisense compound and target is from about 50% to about 60%. In some embodiments, homology, sequence identity or complementarity, is from about 60%, to about 70%. In some embodiments, homology, sequence identity or complementarity, is from about 70% to about 80%. In some embodiments, homology, sequence identity or complementarity, is from about 80% to about 90%. In some embodiments, homology, sequence identity or complementarity, is about 90%, about 92%, about 94%, about 95%, about 96%, about 97%, about 98%, about 99% or about 100%.

An antisense compound is specifically hybridizable when binding of the compound to the target nucleic acid interferes with the normal function of the target nucleic acid to cause a loss of activity, and there is a sufficient degree of complementarity to avoid non-specific binding of the antisense compound to non-target nucleic acid sequences under conditions in which specific binding is desired. Such conditions include, i.e., physiological conditions in the case of in vivo assays or therapeutic treatment, and conditions in which assays are performed in the case of in vitro assays.

An antisense compound, whether DNA, RNA, chimeric, substituted etc, is specifically hybridizable when binding of the compound to the target DNA or RNA molecule interferes with the normal function of the target DNA or RNA to cause a loss of utility, and there is a sufficient degree of complementarily to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

In another embodiment, targeting of a Sirtuin (SIRT) including without limitation, antisense sequences which are identified and expanded, using for example, PCR, hybridization etc., one or more of the sequences set forth as SEQ ID NO: 5 to 14, and the like, modulate the expression or function of a Sirtuin (SIRT). In one embodiment, expression or function is up-regulated as compared to a control. In another embodiment, expression or function is down-regulated as compared to a control.

In another embodiment, oligonucleotides comprise nucleic acid sequences set forth as SEQ ID NOS: 15 to 94 including antisense sequences which are identified and expanded, using for example, PCR, hybridization etc. These oligonucleotides can comprise one or more modified nucleotides, shorter or longer fragments, modified bonds and the like. Examples of modified bonds or internucleotide linkages comprise phosphorothioate, phosphorodithioate or the like. In another embodiment, the nucleotides comprise a phosphorus derivative. The phosphorus derivative (or modified phosphate group) which may be attached to the sugar or sugar analog moiety in the modified oligonucleotides of the present invention may be a monophosphate, diphosphate, triphosphate, alkylphosphate, alkanephosphate, phosphorothioate and the like. The preparation of the above-noted phosphate analogs, and their incorporation into nucleotides, modified nucleotides and oligonucleotides, per se, is also known and need not be described here.

The specificity and sensitivity of antisense is also harnessed by those of skill in the an for therapeutic uses. Antisense oligonucleotides have been employed as therapeutic moieties in the treatment of disease states in animals and man. Antisense oligonucleotides have been safely and effectively administered to humans and numerous clinical trials are presently underway. It is thus established that oligonucleotides can be useful therapeutic modalities that can be configured to be useful in treatment regimes for treatment of cells, tissues and animals, especially humans.

In embodiments of the present invention oligomeric antisense compounds, particularly oligonucleotides, bind to target nucleic acid molecules and modulate the expression and/or function of molecules encoded by a target gene. The functions of DNA to be interfered comprise, for example, replication and transcription. The functions of RNA to be interfered comprise all vital functions such as, for example, translocation of the RNA to the site of protein translation, translation of protein from the RNA, splicing of the RNA to yield one or more mRNA species, and catalytic activity which may be engaged in or facilitated by the RNA. The functions may be up-regulated or inhibited depending on the functions desired.

The antisense compounds, include, antisense oligomeric compounds, antisense oligonucleotides, external guide sequence (EGS) oligonucleotides, alternate splicers, primers, probes, and other oligomeric compounds that hybridize to at least a portion of the target nucleic acid. As such, these compounds may be introduced in the form of single-stranded, double-stranded, partially single-stranded, or circular oligomeric compounds.

Targeting an antisense compound to a particular nucleic acid molecule, in the context of this invention, can be a multistep process. The process usually begins with the identification of a target nucleic acid whose function is to be modulated. This target nucleic acid may be, for example, a cellular gene (or mRNA transcribed from the gene) whose expression is associated with a particular disorder or disease state, or a nucleic acid molecule from an infectious agent. In the present invention, the target nucleic acid encodes a Sirtuin (SIRT).

The targeting process usually also includes determination of at least one target region, segment, or site within the target nucleic acid for the antisense interaction to occur such that the desired effect, e.g., modulation of expression, will result. Within the context of the present invention, the term "region" is defined as a portion of the target nucleic acid having at least one identifiable structure, function, or characteristic. Within regions of target nucleic acids are segments. "Segments" are defined as smaller or sub-portions of regions within a target nucleic acid. "Sites," as used in the present invention, are defined as positions within a target nucleic acid.

In one embodiment, the antisense oligonucleotides bind to the natural antisense sequences of a Sirtuin (SIRT) and modulate the expression and/or function of a Sirtuin (SIRT) (SEQ ID NO: 1 to 3). Examples of antisense sequences include SEQ ID NOS: 4 to 29.

In another embodiment, the antisense oligonucleotides bind to one or more segments of a Sirtuin (SIRT) polynucleotide and modulate the expression and/or function of a Sirtuin (SIRT). The segments comprise at least five consecutive nucleotides of a Sirtuin (SIRT) sense or antisense polynucleotides.

In another embodiment, the antisense oligonucleotides are specific for natural antisense sequences of a Sirtuin (SIRT) wherein binding of the oligonucleotides to the natural antisense sequences of a Sirtuin (SIRT) modulate expression and/or function of a Sirtuin (SIRT).

In another embodiment, oligonucleotide compounds comprise sequences set forth as SEQ ID NOS: 15 to 94, antisense sequences which are identified and expanded, using for example, PCR, hybridization etc These oligonucleotides can comprise one or more modified nucleotides, shorter or longer fragments, modified bonds and the like. Examples of modified bonds or internucleotide linkages comprise phosphorothioate, phosphorodithioate or the like. In another embodiment, the nucleotides comprise a phosphorus derivative. The phosphorus derivative (or modified phosphate group) which may be attached to the sugar or sugar analog moiety in the modified oligonucleotides of the present invention may be a monophosphate, diphosphate, triphosphate, alkylphosphate, alkanephosphate, phosphorothioate and the like. The preparation of the above-noted phosphate analogs, and their incorporation into nucleotides, modified nucleotides and oligonucleotides, per se, is also known and need not be described here.

Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes has a translation initiation codon having the RNA sequence 5'-GUG, 5'-UUG or 5'-CUG; and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). Eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vie to initiate translation of an mRNA transcribed from a gene encoding a Sirtuin (SIRT), regardless of the sequence(s) of such codons. A translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively).

The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. Consequently, the "start codon region" (or "translation initiation codon region") and the "stop codon region" (or "translation termination codon region") are all regions that may be targeted effectively with the antisense compounds of the present invention.

The open reading frame (ORF) or "coding region," which is known in the art to refer to the region between the translation initiation codon and the translation termination codon, is also a region which may be targeted effectively. Within the context of the present invention, a targeted region is the intragenic region encompassing the translation initiation or termination codon of the open reading frame (ORF) of a gene.

Another target region includes the 5' untranslated region (5'UTR), known in the art to refer to the portion of an mRNA in the 5' direction from the translation initiation codon, and thus including nucleotides between the 5' cap site and the translation initiation codon of an mRNA (or corresponding nucleotides on the gene). Still another target region includes the 3' untranslated region (3'UTR), known in the art to refer to the portion of an mRNA in the 3' direction from the translation termination codon, and thus including nucleotides between the translation termination codon and 3' end of an mRNA (or corresponding nucleotides on the gene). The 5' cap site of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap site. Another target region for this invention is the 5' cap region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. In one embodiment, targeting splice sites, i.e., intron-exon junctions or exon-intron junctions, is particularly useful in situations where aberrant splicing is implicated in disease, or where an overproduction of a particular splice product is implicated in disease. An aberrant fusion junction due to rearrangement or deletion is another embodiment of a target site. mRNA transcripts produced via the process of splicing of two (or more) mRNAs from different gene sources are known as "fusion transcripts". Introns can be effectively targeted using antisense compounds targeted to, for example, DNA or pre-mRNA.

In another embodiment, the antisense oligonucleotides bind to coding and/or non-coding regions of a target polynucleotide and modulate the expression and/or function of the target molecule.

In another embodiment, the antisense oligonucleotides bind to natural antisense polynucleotides and modulate the expression and/or function of the target molecule.

In another embodiment, the antisense oligonucleotides bind to sense polynucleotides and modulate the expression and/or function of the target molecule.

Alternative RNA transcripts can be produced from the same genomic region of DNA. These alternative transcripts are generally known as "variants". More specifically, "pre-mRNA variants" are transcripts produced from the same genomic DNA that differ from other transcripts produced from the same genomic DNA in either their start or stop position and contain both intronic and exonic sequence.

Upon excision of one or more exon or intron regions, or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

Variants can be produced through the use of alternative signals to start or stop transcription. Pre-mRNAs and mRNAs can possess more than one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites. Within the context of the invention, the types of variants described herein are also embodiments of target nucleic acids.

The locations on the target nucleic acid to which the antisense compounds hybridize are defined as at least a 5-nucleotide long portion of a target region to which an active antisense compound is targeted.

While the specific sequences of certain exemplary target segments are set forth herein, one of skill in the art will recognize that these serve to illustrate and describe particular embodiments within the scope of the present invention. Additional target segments are readily identifiable by one having ordinary skill in the art in view of this disclosure.

Target segments 5-100 nucleotides in length comprising a stretch of at least five (5) consecutive nucleotides selected from within the illustrative target segments are considered to be suitable for targeting as well.

Target segments can include DNA or RNA sequences that comprise at least the 5 consecutive nucleotides from the 5'-terminus of one of the illustrative target segments (the remaining nucleotides being a consecutive stretch of the same DNA or RNA beginning immediately upstream of the 5'-terminus of the target segment and continuing until the DNA or RNA contains about 5 to about 100 nucleotides). Similarly target segments are represented by DNA or RNA sequences that comprise at least the 5 consecutive nucleotides from the 3'-terminus of one of the illustrative target segments (the remaining nucleotides being a consecutive stretch of the same DNA or RNA beginning immediately downstream of the 3'-terminus of the target segment and continuing until the DNA or RNA contains about 5 to about 100 nucleotides). One having skill in the art armed with the target segments illustrated herein will be able, without undue experimentation, to identify further target segments.

Once one or more target regions, segments or sites have been identified, antisense compounds are chosen which are sufficiently complementary to the target, i.e., hybridize sufficiently well and with sufficient specificity, to give the desired effect.

In embodiments of the invention the oligonucleotides bind to an antisense strand of a particular target. The oligonucleotides are at least 5 nucleotides in length and can be synthesized so each oligonucleotide targets overlapping sequences such that oligonucleotides are synthesized to cover the entire length of the target polynucleotide. The targets also include coding as well as non coding regions.

In one embodiment, specific nucleic acids are targeted by antisense oligonucleotides. Targeting an antisense compound to a particular nucleic acid, is a multistep process. The process usually begins with the identification of a nucleic acid sequence whose function is to be modulated. This may be, for example, a cellular gene (or mRNA transcribed from the gene) whose expression is associated with a particular disorder or disease state, or a non coding polynucleotide such as for example, non coding RNA (ncRNA).

RNAs can be classified into (1) messenger RNAs (mRNAs), which are translated into proteins, and (2) non-protein-coding RNAs (ncRNAs). ncRNAs comprise microRNAs, antisense transcripts and other Transcriptional Units (TU) containing a high density of stop codons and lacking any extensive "Open Reading Frame". Many ncRNAs appear to start from initiation sites in 3' untranslated regions (3'UTRs) of protein-coding loci. ncRNAs are often rare and at least half of the ncRNAs that have been sequenced by the FANTOM consortium seem not to be polyadenylated. Most researchers have for obvious reasons focused on polyadenylated mRNAs that are processed and exported to the cytoplasm. Recently, it was shown that the set of non-polyadenylated nuclear RNAs may be very large, and that many such transcripts arise from intergenic regions. The mechanism by which ncRNAs may regulate gene expression is by base pairing with target transcripts. The RNAs that function by base pairing can be grouped into (1) cis encoded RNAs that are encoded at the same genetic location, but on the opposite strand to the RNAs they act upon and therefore display perfect complementarity to their target, and (2) trans-encoded RNAs that are encoded at a chromosomal location distinct from the RNAs they act upon and generally do not exhibit perfect base-pairing potential with their targets.

Without wishing to be bound by theory, perturbation of an antisense polynucleotide by the antisense oligonucleotides described herein can alter the expression of the corresponding sense messenger RNAs. However, this regulation can either be discordant (antisense knockdown results in messenger RNA elevation) or concordant (antisense knockdown results in concomitant messenger RNA reduction). In these cases, antisense oligonucleotides can be targeted to overlapping or non-overlapping parts of the antisense transcript resulting in its knockdown or sequestration. Coding as well as non-coding antisense can be targeted in an identical manner and that either category is capable of regulating the corresponding sense transcripts—either in a concordant or disconcordant manner. The strategies that are employed in identifying new oligonucleotides for use against a target can be based on the knockdown of antisense RNA transcripts by antisense oligonucleotides or any other means of modulating the desired target.

Strategy 1:

In the case of discordant regulation, knocking down the antisense transcript elevates the expression of the conventional (sense) gene. Should that latter gene encode for a known or putative drug target, then knockdown of its antisense counterpart could conceivably mimic the action of a receptor agonist or an enzyme stimulant.

Strategy 2:

In the case of concordant regulation, one could concomitantly knock down both antisense and sense transcripts and thereby achieve synergistic reduction of the conventional (sense) gene expression. If, for example, an antisense oligonucleotide is used to achieve knockdown, then this strategy can be used to apply one antisense oligonucleotide targeted to the sense transcript and another antisense oligonucleotide to the corresponding antisense transcript, or a single energetically symmetric antisense oligonucleotide that simultaneously targets overlapping sense and antisense transcripts.

According to the present invention, antisense compounds include antisense oligonucleotides, ribozymes, external guide sequence (EGS) oligonucleotides, siRNA compounds, single- or double-stranded RNA interference (RNAi) compounds such as siRNA compounds, and other oligomeric compounds which hybridize to at least a portion of the target nucleic acid and modulate its function. As such, they may be DNA, RNA, DNA-like, RNA-like, or mixtures thereof, or may be mimetics of one or more of these. These compounds may be single-stranded, doublestranded, circular or hairpin oligomeric compounds and may contain structural elements such as internal or terminal bulges, mismatches or loops. Antisense compounds are routinely prepared linearly but can be joined or otherwise prepared to be circular and/or branched. Antisense compounds can include constructs such as, for example, two strands hybridized to form a wholly or partially double-stranded compound or a single strand with sufficient self-complementarity to allow for hybridization and formation of a fully or partially double-stranded compound. The two strands can be linked internally leaving free 3' or 5' termini or can be linked to form a continuous hairpin structure or loop. The hairpin structure may contain an overhang on either the 5' or 3' terminus producing an extension of single stranded character. The double stranded compounds optionally can include overhangs on the ends. Further modifications can include conjugate groups attached to one of the termini, selected nucleotide positions, sugar positions or to one of the internucleoside linkages. Alternatively, the two strands can be linked via a non-nucleic acid moiety or linker group. When formed from only one strand, dsRNA can take the form of a self-complementary hairpin-type molecule that doubles back on itself to form a duplex. Thus, the dsRNAs can be fully or partially double stranded. Specific modulation of gene expression can be achieved by stable expression of dsRNA hairpins in transgenic cell lines, however, in some embodiments, the gene expression or function is up regulated. When formed from two strands, or a single strand that takes the form of a self-complementary hairpin-type molecule doubled back on itself to form a duplex, the two strands (or duplex-forming regions of a single strand) are complementary RNA strands that base pair in Watson-Crick fashion.

Once introduced to a system, the compounds of the invention may elicit the action of one or more enzymes or structural proteins to effect cleavage or other modification of the target nucleic acid or may work via occupancy-based mechanisms. In general, nucleic acids (including oligonucleotides) may be described as "DNA-like" (i.e., generally having one or more 2'-deoxy sugars and, generally, T rather than U bases) or "RNA-like" (i.e., generally having one or more 2'-hydroxyl or 2'-modified sugars and, generally U rather than T bases). Nucleic acid helices can adopt more than one type of structure, most commonly the A- and B-forms. It is believed that, in general, oligonucleotides which have B-form-like structure are "DNA-like" and those which have A-formlike structure are "RNA-like." In some (chimeric) embodiments, an antisense compound may contain both A- and B-form regions.

In another embodiment, the desired oligonucleotides or antisense compounds, comprise at least one of: antisense RNA, antisense DNA, chimeric antisense oligonucleotides, antisense oligonucleotides comprising modified linkages, interference RNA (RNAi), short interfering RNA (siRNA); a micro, interfering RNA (miRNA); a small, temporal RNA (stRNA); or a short, hairpin RNA (shRNA); small RNA-induced gene activation (RNAa); small activating RNAs (saRNAs), or combinations thereof.

dsRNA can also activate gene expression, a mechanism that has been termed "small RNA-induced gene activation" or RNAa dsRNAs targeting gene promoters induce potent transcriptional activation of associated genes. RNAa was demonstrated in human cells using synthetic dsRNAs, termed "small activating RNAs" (saRNAs).

Small double-stranded RNA (dsRNA), such as small interfering RNA (siRNA) and microRNA (miRNA), have been found to be the trigger of an evolutionary conserved mechanism known as RNA interference (RNAi). RNAi invariably leads to gene silencing. However, in instances described in detail in the examples section which follows, oligonucleotides are shown to increase the expression and/or function of the Sirtuin (SIRT) polynucleotides and encoded products thereof. dsRNAs may also act as small activating RNAs (saRNA). Without wishing to be bound by theory, by targeting sequences in gene promoters, saRNAs would induce target gene expression in a phenomenon referred to as dsRNA-induced transcriptional activation (RNAa).

In a further embodiment, the "target segments" identified herein may be employed in a screen for additional compounds that modulate the expression of a Sirtuin (SIRT) polynucleotide. "Modulators" are those compounds that decrease or increase the expression of a nucleic acid molecule encoding a Sirtuin (SIRT) and which comprise at least a 5-nucleotide portion that is complementary to a target segment. The screening method comprises the steps of contacting a target segment of a nucleic acid molecule encoding sense or natural antisense polynucleotides of a Sirtuin (SIRT) with one or more candidate modulators, and selecting for one or more candidate modulators which decrease or increase the expression of a nucleic acid molecule encoding a Sirtuin (SIRT) polynucleotide, e.g. SEQ ID NOS: 15 to 94. Once it is shown that the candidate modulator or modulators are capable of modulating (e.g. either decreasing or increasing) the expression of a nucleic acid molecule encoding a Sirtuin (SIRT) polynucleotide, the modulator may then be employed in further investigative studies of the function of a Sirtuin (SIRT) polynucleotide, or for use as a research, diagnostic, or therapeutic agent in accordance with the present invention.

Targeting the natural antisense sequence modulates the function of the target gene. For example, the Sirtuin (SIRT) (e.g. accession numbers NM_012238.3, NM_001159589, NM_012239, NM_016539). In a embodiment, the target is an antisense polynucleotide of the Sirtuin (SIRT). In a embodiment, an antisense oligonucleotide targets sense and/or natural antisense sequences of a Sirtuin (SIRT) polynucleotide (e.g. accession numbers NM_012238.3, NM_001159589, NM_012239, NM 016539), variants, alleles, isoforms, homologs, mutants, derivatives, fragments and complementary sequences thereto. Preferably the oligonucleotide is an antisense molecule and the targets include coding and noncoding regions of antisense and/or sense Sirtuin (SIRT) polynucleotides.

The target segments of the present invention may be also be combined with their respective complementary antisense compounds of the present invention to form stabilized double-stranded (duplexed) oligonucleotides.

Such double stranded oligonucleotide moieties have been shown in the art to modulate target expression and regulate translation as well as RNA processing via an antisense mechanism. Moreover, the double-stranded moieties may be subject to chemical modifications. For example, such double-stranded moieties have been shown to inhibit the target by the classical hybridization of antisense strand of the duplex to the target, thereby triggering enzymatic degradation of the target.

In a embodiment, an antisense oligonucleotide targets Sirtuin (SIRT) polynucleotides (e.g. accession numbers NM_012238.3, NM_001159589, NM_012239, NM 016539), variants, alleles, isoforms, homologs, mutants, derivatives, fragments and complementary sequences thereto. Preferably the oligonucleotide is an antisense molecule.

In accordance with embodiments of the invention, the target nucleic acid molecule is not limited to Sirtuin (SIRT) alone but extends to any of the isoforms, receptors, homologs and the like of a Sirtuin (SIRT) molecule.

In another embodiment, an oligonucleotide targets a natural antisense sequence of a Sirtuin (SIRT) polynucleotide, for example, polynucleotides set forth as SEQ ID NO: 5 to 14, and any variants, alleles, homologs, mutants, derivatives, fragments and complementary sequences thereto. Examples of antisense oligonucleotides are set forth as SEQ ID NOS: 15 to 94.

In one embodiment, the oligonucleotides are complementary to or bind to nucleic acid sequences of a Sirtuin (SIRT) antisense, including without limitation noncoding sense and/or antisense sequences associated with a Sirtuin (SIRT) polynucleotide and modulate expression and/or function of a Sirtuin (SIRT) molecule.

In another embodiment, the oligonucleotides are complementary to or bind to nucleic acid sequences of a Sirtuin (SIRT) natural antisense, set forth as SEQ ID NO: 5 to 14 and modulate expression and/or function of a Sirtuin (SIRT) molecule.

In a embodiment, oligonucleotides comprise sequences of at least 5 consecutive nucleotides of SEQ ID NOS: 15 to 94 and modulate expression and/or function of a Sirtuin (SIRT) molecule.

The polynucleotide targets comprise Sirtuin (SIRT), including family members thereof, variants of a Sirtuin (SIRT); mutants of a Sirtuin (SIRT), including SNPs; non-coding sequences of a Sirtuin (SIRT); alleles of a Sirtuin (SIRT); species variants, fragments and the like. Preferably the oligonucleotide is an antisense molecule.

In another embodiment, the oligonucleotide targeting Sirtuin (SIRT) polynucleotides, comprise: antisense RNA, interference RNA (RNAi), short interfering RNA (siRNA); micro interfering RNA (miRNA); a small, temporal RNA (stRNA); or a short, hairpin RNA (shRNA); small RNA-induced gene activation (RNAa); or, small activating RNA (saRNA).

In another embodiment, targeting of a Sirtuin (SIRT) polynucleotide, e.g. SEQ ID NO: 5 to 14 modulate the expression or function of these targets. In one embodiment, expression or function is up-regulated as compared to a control. In another embodiment, expression or function is down-regulated as compared to a control.

In another embodiment, antisense compounds comprise sequences set forth as SEQ ID NOS: 15 to 94. These oligonucleotides can comprise one or more modified nucleotides, shorter or longer fragments, modified bonds and the like.

In another embodiment, SEQ ID NOS: 15 to 94 comprise one or more LNA nucleotides.

The modulation of a desired target nucleic acid can be carried out in several ways known in the an. For example, antisense oligonucleotides, siRNA etc. Enzymatic nucleic acid molecules (e.g., ribozymes) are nucleic acid molecules capable of catalyzing one or more of a variety of reactions, including the ability to repeatedly cleave other separate nucleic acid molecules in a nucleotide base sequence-specific manner. Such enzymatic nucleic acid molecules can be used, for example, to target virtually any RNA transcript.

Because of their sequence-specificity, trans-cleaving enzymatic nucleic acid molecules show promise as therapeutic agents for human disease. Enzymatic nucleic acid molecules can be designed to cleave specific RNA targets within the background of cellular RNA. Such a cleavage event renders the mRNA non-functional and abrogates protein expression from that RNA. In this manner, synthesis of a protein associated with a disease state can be selectively inhibited.

In general, enzymatic nucleic acids with RNA cleaving activity act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

Several approaches such as in vitro selection (evolution) strategies have been used to evolve new nucleic acid catalysts capable of catalyzing a variety of reactions, such as cleavage and ligation of phosphodiester linkages and amide linkages.

The development of ribozymes that are optimal for catalytic activity would contribute significantly to any strategy that employs RNA-cleaving ribozymes for the purpose of regulating gene expression. The hammerhead ribozyme, for example, functions with a catalytic rate (kcat) of about 1 min-1 in the presence of saturating (10 mM) concentrations of Mg2+ cofactor. An artificial "RNA ligase" ribozyme has been shown to catalyze the corresponding self-modification reaction with a rate of about 100 min-1. In addition, it is known that certain modified hammerhead ribozymes that have substrate binding arms made of DNA catalyze RNA cleavage with multiple turn-over rates that approach 100 mind. Finally, replacement of a specific residue within the catalytic core of the hammerhead with certain nucleotide analogues gives modified ribozymes that show as much as a 10-fold improvement in catalytic rate. These findings demonstrate that ribozymes can promote chemical transformations with catalytic rates that are significantly greater than those displayed in vitro by most natural self-cleaving ribozymes. It is then possible that the structures of certain selfcleaving ribozymes may be optimized to give maximal catalytic activity, or that entirely new RNA motifs can be made that display significantly faster rates for RNA phosphodiester cleavage.

Intermolecular cleavage of an RNA substrate by an RNA catalyst that fits the "hammerhead" model was first shown in 1987. The RNA catalyst was recovered and reacted with multiple RNA molecules, demonstrating that it was truly catalytic.

Catalytic RNAs designed based on the "hammerhead" motif have been used to cleave specific target sequences by making appropriate base changes in the catalytic RNA to maintain necessary base pairing with the target sequences. This has allowed use of the catalytic RNA to cleave specific target sequences and indicates that catalytic RNAs designed according to the "hammerhead" model may possibly cleave specific substrate RNAs in vivo.

RNA interference (RNAi) has become a powerful tool for modulating gene expression in mammals and mammalian cells. This approach requires the delivery of small interfering RNA (siRNA) either as RNA itself or as DNA, using an expression plasmid or virus and the coding sequence for small hairpin RNAs that are processed to siRNAs. This system enables efficient transport of the pre-siRNAs to the cytoplasm where they are active and permit the use of regulated and tissue specific promoters for gene expression.

In one embodiment, an oligonucleotide or antisense compound comprises an oligomer or polymer of ribonucleic acid (RNA) and/or deoxyribonucleic acid (DNA), or a mimetic, chimera, analog or homolog thereof. This term includes oligonucleotides composed of naturally occurring nucleotides, sugars and covalent internucleoside (backbone) linkages as well as oligonucleotides having non-naturally occurring portions which function similarly. Such modified or substituted oligonucleotides are often desired over native forms because of desirable properties such as, for example, enhanced cellular uptake, enhanced affinity for a target nucleic acid and increased stability in the presence of nucleases.

According to the present invention, the oligonucleotides or "antisense compounds" include antisense oligonucleotides (e.g. RNA, DNA, mimetic, chimera, analog or homolog thereof), ribozymes, external guide sequence (EGS) oligonucleotides, siRNA compounds, single- or double-stranded RNA interference (RNAi) compounds such as siRNA compounds, saRNA, aRNA, and other oligomeric compounds which hybridize to at least a portion of the target nucleic acid and modulate its function. As such, they may be DNA, RNA, DNA-like, RNA-like, or mixtures thereof, or may be mimetics of one or more of these. These compounds may be single-stranded, double-stranded, circular or hairpin oligomeric compounds and may contain structural elements such as internal or terminal bulges, mismatches or loops. Antisense compounds are routinely prepared linearly but can be joined or otherwise prepared to be circular and/or branched. Antisense compounds can include constructs such as, for example, two strands hybridized to form a wholly or partially double-stranded compound or a single strand with sufficient self-complementarity to allow for hybridization and formation of a fully or partially double-stranded compound. The two strands can be linked internally leaving free 3' or 5' termini or can be linked to form a continuous hairpin structure or loop. The hairpin structure may contain an overhang on either the 5' or 3' terminus producing an extension of single stranded character. The double stranded compounds optionally can include overhangs on the ends. Further modifications can include conjugate groups attached to one of the termini, selected nucleotide positions, sugar positions or to one of the internucleoside linkages. Alternatively, the two strands can be linked via a non-nucleic acid moiety or linker group. When formed from only one strand, dsRNA can take the form of a self-complementary hairpin-type molecule that doubles back on itself to form a duplex. Thus, the dsRNAs can be fully or partially double stranded. Specific modulation of gene expression can be achieved by stable expression of dsRNA hairpins in transgenic cell lines. When formed from two strands, or a single strand that takes the form of a self-complementary hairpin-type molecule doubled back on itself to form a duplex, the two strands (or duplex-forming regions of a single strand) are complementary RNA strands that base pair in Watson-Crick fashion.

Once introduced to a system, the compounds of the invention may elicit the action of one or more enzymes or structural proteins to effect cleavage or other modification of the target nucleic acid or may work via occupancy-based mechanisms. In general, nucleic acids (including oligonucleotides) may be described as "DNA-like" (i.e., generally having one or more 2'-deoxy sugars and, generally, T rather than U bases) or "RNA-like" (i.e., generally having one or more 2'-hydroxyl or 2'-modified sugars and, generally U rather than T bases). Nucleic acid helices can adopt more than one type of structure, most commonly the A- and B-forms. It is believed that, in general, oligonucleotides which have B-form-like structure are "DNA-like" and those which have A-formlike structure are "RNA-like." In some (chimeric) embodiments, an antisense compound may contain both A- and B-form regions.

The antisense compounds in accordance with this invention can comprise an antisense portion from about 5 to about 80 nucleotides (i.e. from about 5 to about 80 linked nucleosides) in length. This refers to the length of the antisense strand or portion of the antisense compound. In other words, a single-stranded antisense compound of the invention comprises from 5 to about 80 nucleotides, and a double-stranded antisense compound of the invention (such as a dsRNA, for example) comprises a sense and an antisense strand or portion of 5 to about 80 nucleotides in length. One of ordinary skill in the art will appreciate that this comprehends antisense portions of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleotides in length, or any range therewithin.

In one embodiment, the antisense compounds of the invention have antisense portions of 10 to 50 nucleotides in length. One having ordinary skill in the art will appreciate that this embodies oligonucleotides having antisense portions of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length, or any range there within. In some embodiments, the oligonucleotides are 15 nucleotides in length.

In one embodiment, the antisense or oligonucleotide compounds of the invention have antisense portions of 12 or 13 to 30 nucleotides in length. One having ordinary skill in the art will appreciate that this embodies antisense compounds having antisense portions of 12, 13, 14, 15, 16, 17, 18, 19, 20, 21, 22, 23, 24, 25, 26, 27, 28, 29 or 30 nucleotides in length, or any range therewithin.

In another embodiment, the oligomeric compounds of the present invention also include variants in which a different base is present at one or more of the nucleotide positions in the compound. For example, if the first nucleotide is an adenosine, variants may be produced which contain thymidine, guanosine or cytidine at this position. This may be done at any of the positions of the antisense or dsRNA compounds. These compounds are then tested using the methods described herein to determine their ability to inhibit expression of a target nucleic acid.

In some embodiments, homology, sequence identity or complementarity, between the antisense compound and target is from about 40% to about 60%. In some embodiments, homology, sequence identity or complementarity, is from about 60% to about 70%. In some embodiments, homology, sequence identity or complementarity, is from about 70% to about 80%. In some embodiments, homology, sequence identity or complementarity, is from about 80% to about 90%. In some embodiments, homology, sequence identity or complementarity, is about 90%, about 92%, about 94%, about 95%, about 96%, about 97%, about 98%, about 99% or about 100%.

In another embodiment, the antisense oligonucleotides, such as for example, nucleic acid molecules set forth in SEQ ID NOS: 4 to 29 comprise one or more substitutions or modifications. In one embodiment, the nucleotides are substituted with locked nucleic acids (LNA).

In another embodiment, the oligonucleotides target one or more regions of the nucleic acid molecules sense and/or antisense of coding and/or non-coding sequences associated with Sirtuin (SIRT) and the sequences set forth as SEQ ID NOS: 1 to 14. The oligonucleotides are also targeted to overlapping regions of SEQ ID NOS: 1 to 14.

Certain oligonucleotides of this invention are chimeric oligonucleotides. "Chimeric oligonucleotides" or "chimeras," in the context of this invention, are oligonucleotides which contain two or more chemically distinct regions, each made up of at least one nucleotide. These oligonucleotides typically contain at least one region of modified nucleotides that confers one or more beneficial properties (such as, for example, increased nuclease resistance, increased uptake into cells, increased binding affinity for the target) and a region that is a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of antisense modulation of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art. In one embodiment, a chimeric oligonucleotide comprises at least one region modified to increase target binding affinity, and, usually, a region that acts as a substrate for RNAse H. Affinity of an oligonucleotide for its target (in this case, a nucleic acid encoding ras) is routinely determined by measuring the Tm of an oligonucleotide/target pair, which is the temperature at which the oligonucleotide and target dissociate; dissociation is detected spectrophotometrically. The higher the Tm, the greater is the affinity of the oligonucleotide for the target.

Chimeric antisense compounds of the invention may be formed as composite structures of two or more oligonucleotides, modified oligonucleotides, oligonucleosides and/or oligonucleotides mimetics as described above. Such; compounds have also been referred to in the art as hybrids or gapmers. Representative United States patents that teach the preparation of such hybrid structures comprise, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference.

In another embodiment, the region of the oligonucleotide which is modified comprises at least one nucleotide modified at the 2' position of the sugar, most preferably a 2'-Oalkyl, 2'-O-alkyl-O-alkyl or 2'-fluoro-modified nucleotide. In other embodiments, RNA modifications include 2'-fluoro, 2'-amino and 2' O-methyl modifications on the ribose of pyrimidines, abasic residues or an inverted base at the 3' end of the RNA. Such modifications are routinely incorporated into oligonucleotides and these oligonucleotides have been shown to have a higher Tm (i.e., higher target binding affinity) than; 2'-deoxyoligonucleotides against a given target. The effect of such increased affinity is to greatly enhance RNAi oligonucleotide inhibition of gene expression. RNAse H is a cellular endonuclease that cleaves the RNA strand of RNA:DNA duplexes; activation of this enzyme therefore results in cleavage of the RNA target, and thus can greatly enhance the efficiency of RNAi inhibition. Cleavage of the RNA target can be routinely demonstrated by gel electrophoresis. In another embodiment, the chimeric oligonucleotide is also modified to enhance nuclease resistance. Cells contain a variety of exo- and endo-nucleases which can degrade nucleic acids. A number of nucleotide and nucleoside modifications have been shown to make the oligonucleotide into which they are incorporated more resistant to nuclease digestion than the native oligodeoxynucleotide. Nuclease resistance is routinely measured by incubating oligonucleotides with cellular extracts or isolated nuclease solutions and measuring the extent of intact oligonucleotide remaining over time, usually by gel electrophoresis. Oligonucleotides which have been modified to enhance their nuclease resistance survive intact for a longer time than unmodified oligonucleotides. A variety of oligonucleotide modifications have been demonstrated to enhance or confer nuclease resistance. Oligonucleotides which contain at least one phosphorothioate modification are presently more preferred. In some cases, oligonucleotide modifications which enhance target binding affinity are also, independently, able to enhance nuclease resistance. Some desirable modifications can be found in De Mesmaeker et al. (1995) Acc. Chem. Res., 28:366-374.

Specific examples of some oligonucleotides envisioned for this invention include those comprising modified backbones, for example, phosphorothioates, phosphotriesters, methyl phosphonates, short chain alkyl or cycloalkyl intersugar linkages or short chain heteroatomic or heterocyclic intersugar linkages. Most are oligonucleotides with phosphorothioate backbones and those with heteroatom backbones, particularly CH2-NH—O—CH2. CH, —N(CH3)-O—CH2 [known as a methylene(methylimino) or MMI backbone], CH2-O—N(CH3)-CH2, CH2-N(CH3)-N(CH3)-CH2 and O—N(CH3)-CH2-CH2 backbones, wherein the native phosphodiester backbone is represented as O—P—O—CH). The amide backbones disclosed by De Mesmaeker et al. (1995) Acc. Chem. Res. 28:366-374 are also preferred. Also are oligonucleotides having morpholino backbone structures (Summerton and Weller, U.S. Pat. No. 5,034,506). In other embodiments, such as the peptide nucleic acid (PNA) backbone, the phosphodiester backbone of the oligonucleotide is replaced with a polyamide backbone, the nucleotides being bound directly or indirectly to the aza nitrogen atoms of the polyamide backbone. Oligonucleotides may also comprise one or more substituted sugar moieties, oligonucleotides comprise one of the following at the 2' position: OH, SH, SCH3, F, OCN, OCH3 OCH3, OCH3 O(CH2)n CH3, O(CH2)n NH2 or O(CH2)n CH3 where n is from 1 to about 10; C1 to C10 lower alkyl, alkoxyalkoxy, substituted lower alkyl, alkaryl or aralkyl; Cl; Br; CN; CF3; OCF3; O-, S-, or N-alkyl; O-, S-, or N-alkenyl; SOCH3; SO2 CH3; ONO2; NO2; N3; NH2; heterocycloalkyl; heterocycloalkaryl; aminoalkylamino; polyalkylamino; substituted silyl; an RNA cleaving group; a reporter group; an intercalator, a group for improving the pharmacokinetic properties of an oligonucleotide; or a group for improving the pharmacodynamic properties of an oligonucleotide and other substituents having similar properties. A modification includes 2'-methoxyethoxy [2'-O—CH2 CH2 OCH3, also known as 2'-O-(2-methoxyethyl)]. Other modifications include 2'-methoxy (2'-O—CH3), 2'-propoxy (2'-OCH2 CH2CH3) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

Oligonucleotides may also include, additionally or alternatively, nucleobase (often referred to in the art simply as "base") modifications or substitutions. As used herein, "unmodified" or "natural" nucleotides include adenine (A), guanine (G), thymine (T), cytosine (C) and uracil (U). Modified nucleotides include nucleotides found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic nucleotides, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl)adenine and 2,6-diaminopurine. A "universal" base known in the art, e.g., inosine, may be included. 5-Me-C substitutions have been shown to increase nucleic acid duplex stability by 0.6-1.2° C. (Sanghvi, Y. S., in Crooke, S. T. and Lebleu, B., eds., Antisense Research and Applications, CRC Press, Boca Raton, 1993, pp. 276-278) and are presently base substitutions.

Another modification of the oligonucleotides of the invention involves chemically linking to the oligonucleotide one or more moieties or conjugates which enhance the activity or cellular uptake of the oligonucleotide. Such moieties include but are not limited to lipid moieties such as a cholesterol moiety, a cholesteryl moiety, a thioether, e.g., hexyl-S-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid. Oligonucleotides comprising lipophilic moieties, and methods for preparing such oligonucleotides are known in the art, for example, U.S. Pat. Nos. 5,138,045, 5,218,105 and 5,459,255.

It is not necessary for all positions in a given oligonucleotide to be uniformly modified, and in fact more than one of the aforementioned modifications may be incorporated in a single oligonucleotide or even at within a single nucleoside within an oligonucleotide. The present invention also includes oligonucleotides which are chimeric oligonucleotides as hereinbefore defined.

In another embodiment, the nucleic acid molecule of the present invention is conjugated with another moiety including but not limited to abasic nucleotides, polyether, polyamine, polyamides, peptides, carbohydrates, lipid, or polyhydrocarbon compounds. Those skilled in the art will recognize that these molecules can be linked to one or more of any nucleotides comprising the nucleic acid molecule at several positions on the sugar, base or phosphate group.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed, the actual synthesis of the oligonucleotides is well within the talents of one of ordinary skill in the art. It is also well known to use similar techniques to prepare other oligonucleotides such as the phosphorothioates and alkylated derivatives. It is also well known to use similar techniques and commercially available modified amidites and controlled-pore glass (CPG) products such as biotin, fluorescein, acridine or psoralen-modified amidites and/or CPG (available from Glen Research, Sterling Va.) to synthesize fluorescently labeled, biotinylated or other modified oligonucleosides such as cholesterol-modified oligonucleotides.

In accordance with the invention, use of modifications such as the use of LNA monomers to enhance the potency, specificity and duration of action and broaden the routes of administration of oligonucleotides comprised of current chemistries such as MOE, ANA, FANA, PS etc. This can be achieved by substituting some of the monomers in the current oligonucleotides by LNA monomers. The LNA modified oligonucleotide may have a size similar to the parent compound or may be larger or preferably smaller. It is that such LNA-modified oligonucleotides contain less than about 70%, more preferably less than about 60%, most preferably less than about 50% LNA monomers and that their sizes are between about 5 and 25 nucleotides, mare preferably between about 12 and 20 nucleotides.

Modified oligonucleotide backbones comprise, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative United States patents that teach the preparation of the above phosphorus containing linkages comprise, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts.

Representative United States patents that teach the preparation of the above oligonucleosides comprise, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070;

5,663,312; 5,633,360; 5,677,437; and 5,677,439, each of which is herein incorporated by reference.

In other oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds comprise, but are not limited to, U.S. Pat. Nos. 5,539,082; 5,714,331; and 5,719,262, each of which is herein incorporated by reference. Further teaching of PNA compounds can be found in Nielsen, et al. (1991) *Science* 254, 1497-1500.

In another embodiment of the invention the oligonucleotides with phosphorothioate backbones and oligonucleosides with heteroatom backbones, and in particular —CH2-NH—O—CH2-, —CH2-N(CH3)-O—CH2-known as a methylene (methylimino) or MMI backbone, —CH2-O—N (CH3)-CH2-, —CH2N(CH3)-N(CH3) CH2- and —O—N (CH3)-CH2-CH2- wherein the native phosphodiester backbone is represented as —O—P—O—CH2- of the above referenced U.S. Pat. No. 5,489,677, and the amide backbones of the above referenced U.S. Pat. No. 5,602,240. Also are oligonucleotides having morpholino backbone structures of the above-referenced U.S. Pat. No. 5,034,506.

Modified oligonucleotides may also contain one or more substituted sugar moieties, oligonucleotides comprise one of the following at the 2' position: OH; F; O-, S-, or N-alkyl; O-, S-, or N-alkenyl; O-, S- or N-alkynyl; or O alkyl-O-alkyl, wherein the alkyl, alkenyl and alkynyl may be substituted or unsubstituted C to CO alkyl or C2 to CO alkenyl and alkynyl. Particularly are O (CH2)n OmCH3, O(CH2)n, OCH3, O(CH2)nNH2, O(CH2)nCH3, O(CH2)nONH2, and O(CH2nON(CH2)nCH3)2 where n and m can be from 1 to about 10. Other oligonucleotides comprise one of the following at the 2' position: C to CO, (lower alkyl, substituted lower alkyl, alkaryl, aralkyl, O-alkaryl or O-aralkyl, SH, SCH3, OCN, Cl, Br, CN, CF3, OCF3, SOCH3, SO2CH3, ONO2, NO2, N3, NH2, heterocycloalkyl heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A modification comprises 2'-methoxyethoxy (2'-O—CH2CH2OCH3, also known as 2'-O-(2-methoxyethyl) or 2'-MOE) i.e., an alkoxyalkoxy group. A further modification comprises 2'-dimethylaminooxyethoxy, i.e., a O(CH2)2ON(CH3)2 group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—CH2-O—CH2-N(CH2)2.

Other modifications comprise 2'-methoxy (2'-O CH3), 2'-aminopropoxy (2'-O CH2CH2CH2NH2) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures comprise, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference.

Oligonucleotides may also comprise nucleobase (often referred to in the art simply as "base") modifications or substitutions. As used herein, "unmodified" or "natural" nucleotides comprise the purine bases adenine (A) and guanine (G), and the pyrimidine bases thymine (T), cytosine (C) and uracil (U). Modified nucleotides comprise other synthetic and natural nucleotides such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine and 3-deazaguanine and 3-deazaadenine.

Further, nucleotides comprise those disclosed in U.S. Pat. No. 3,687,808, those disclosed in 'The Concise Encyclopedia of Polymer Science And Engineering', pages 858-859, Kroschwitz, J. I., ed. John Wiley & Sons, 1990, those disclosed by Englisch et al., 'Angewandle Chemie, International Edition', 1991, 30, page 613, and those disclosed by Sanghvi, Y. S., Chapter 15, 'Antisense Research and Applications', pages 289-302, Crooke, S. T. and Lebleu, B. ea., CRC Press, 1993. Certain of these nucleotides are particularly useful for increasing the binding affinity of the oligomeric compounds of the invention. These comprise 5-substituted pyrimidines, 6-azapyrimidines and N-2, N-6 and 0-6 substituted purines, comprising 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds, 'Antisense Research and Applications', CRC Press, Boca Raton, 1993, pp. 276-278) and are presently base substitutions, even more particularly when combined with 2'-Omethoxyethyl sugar modifications.

Representative United States patents that teach the preparation of the above noted modified nucleotides as well as other modified nucleotides comprise, but are not limited to, U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,596,091; 5,614,617; 5,750,692, and 5,681,941, each of which is herein incorporated by reference.

Another modification of the oligonucleotides of the invention involves chemically linking to the oligonucleotide one or more moieties or conjugates, which enhance the activity, cellular distribution, or cellular uptake of the oligonucleotide.

Such moieties comprise but are not limited to, lipid moieties such as a cholesterol moiety, cholic acid, a thioether, e.g., hexyl-S-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-t oxycholesterol moiety.

Representative United States patents that teach the preparation of such oligonucleotides conjugates comprise, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5262,536; 5,272,250; 5,292,873; 5,317,098; 5,371,241, 5,391, 723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

Drug Discovery:

The compounds of the present invention can also be applied in the areas of drug discovery and target validation. The present invention comprehends the use of the compounds and target segments identified herein in drug discovery efforts to elucidate relationships that exist between a Sirtuin (SIRT) polynucleotide and a disease state, phenotype, or condition. These methods include detecting or modulating a Sirtuin (SIRT) polynucleotide comprising contacting a sample, tissue, cell, or organism with the compounds of the present invention, measuring the nucleic acid or protein level of a Sirtuin (SIRT) polynucleotide and/or a related phenotypic or chemical endpoint at some time after treatment, and optionally comparing the measured value to a non-treated sample or sample treated with a further compound of the invention. These methods can also be performed in parallel or in combination with other experiments to determine the function of unknown genes for the process of target validation or to determine the validity of a particular gene product as a target for treatment or prevention of a particular disease, condition, or phenotype.

Assessing Up-Regulation or Inhibition of Gene Expression:

Transfer of an exogenous nucleic acid into a host cell or organism can be assessed by directly detecting the presence of the nucleic acid in the cell or organism. Such detection can be achieved by several methods well known in the art. For example, the presence of the exogenous nucleic acid can be detected by Southern blot or by a polymerase chain reaction (PCR) technique using primers that specifically amplify nucleotide sequences associated with the nucleic acid. Expression of the exogenous nucleic acids can also be measured using conventional methods including gene expression analysis. For instance, mRNA produced from an exogenous nucleic acid can be detected and quantified using a Northern blot and reverse transcription PCR (RT-PCR).

Expression of RNA from the exogenous nucleic acid can also be detected by measuring an enzymatic activity or a reporter protein activity. For example, antisense modulatory activity can be measured indirectly as a decrease or increase in target nucleic acid expression as an indication that the exogenous nucleic acid is producing the effector RNA. Based on sequence conservation, primers can be designed and used to amplify coding regions of the target genes. Initially, the most highly expressed coding region from each gene can be used to build a model control gene, although any coding or non coding region can be used. Each control gene is assembled by inserting each coding region between a reporter coding region and its poly(A) signal. These plasmids would produce an mRNA with a reporter gene in the upstream portion of the gene and a potential RNAi target in the 3' non-coding region. The effectiveness of individual antisense oligonucleotides would be assayed by modulation of the reporter gene. Reporter genes useful in the methods of the present invention include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), red fluorescent protein (RFP), yellow fluorescent protein (YFP), cyan fluorescent protein (CFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracycline. Methods to determine modulation of a reporter gene are well known in the art, and include, but are not limited to, fluorometric methods (e.g. fluorescence spectroscopy, Fluorescence Activated Cell Sorting (FACS), fluorescence microscopy), antibiotic resistance determination.

SIRT1, SIRT3 and SIRT6 proteins and mRNA expression can be assayed using methods known to those of skill in the art and described elsewhere herein. For example, immunoassays such as the ELISA can be used to measure protein levels. Sirtuin (SIRT) antibodies for ELISAs are available commercially, e.g., from R&D Systems (Minneapolis, Minn.), Abcam, Cambridge, Mass.

In embodiments, SIRT1, SIRT3 and SIRT6 expression (e.g., mRNA or protein) in a sample (e.g., cells or tissues in vivo or in vitro) treated using an antisense oligonucleotide of the invention is evaluated by comparison with Sirtuin (SIRT) expression in a control sample. For example, expression of the protein or nucleic acid can be compared using methods known to those of skill in the art with that in a mock-treated or untreated sample. Alternatively, comparison with a sample treated with a control antisense oligonucleotide (e.g., one having an altered or different sequence) can be made depending on the information desired. In another embodiment, a difference in the expression of the Sirtuin (SIRT) protein or nucleic acid in a treated vs. an untreated sample can be compared with the difference in expression of a different nucleic acid (including any standard deemed appropriate by the researcher, e.g., a housekeeping gene) in a treated sample vs. an untreated sample.

Observed differences can be expressed as desired, e.g., in the form of a ratio or fraction, for use in a comparison with control. In embodiments, the level of a Sirtuin (SIRT) mRNA or protein, in a sample treated with an antisense oligonucleotide of the present invention, is increased or decreased by about 1.25-fold to about 10-fold or more relative to an untreated sample or a sample treated with a control nucleic acid. In embodiments, the level of a Sirtuin (SIRT) mRNA or protein is increased or decreased by at least about 1.25-fold, at least about 1.3-fold, at least about 1.4-fold, at least about 1.5-fold, at least about 1.6-fold, at least about 1.7-fold, at least about 1.8-fold, at least about 2-fold, at least about 2.5-fold, at least about 3-fold, at least about 3.5-fold, at least about 4-fold, at least about 4.5-fold, at least about 5-fold, at least about 5.5-fold, at least about 6-fold, at least about 6.5-fold, at least about 7-fold, at least about 7.5-fold, at least about 8-fold, at least about 8.5-fold, at least about 9-fold, at least about 9.5-fold, or at least about 10-fold or more.

Kits, Research Reagents, Diagnostics, and Therapeutics

The compounds of the present invention can be utilized for diagnostics, therapeutics, and prophylaxis, and as research reagents and components of kits. Furthermore, antisense oligonucleotides, which are able to inhibit gene expression with exquisite specificity, are often used by those of ordinary skill to elucidate the function of particular genes or to distinguish between functions of various members of a biological pathway.

For use in kits and diagnostics and in various biological systems, the compounds of the present invention, either alone or in combination with other compounds or therapeutics, are useful as tools in differential and/or combinatorial analyses to elucidate expression patterns of a portion or the entire complement of genes expressed within cells and tissues.

As used herein the term "biological system" or "system" is defined as any organism, cell, cell culture or tissue that expresses, or is made competent to express products of the Sirtuin (SIRT). These include, but are not limited to, humans, transgenic animals, cells, cell cultures, tissues, xenografts, transplants and combinations thereof.

As one non limiting example, expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds that affect expression patterns.

Examples of methods of gene expression analysis known in the art include DNA arrays or microarrays (Brazma and Vilo, (2000) *FEBS Lett.,* 480, 17-24; Celis, et al., (2000) *FEBS Lett.,* 480, 2-16), SAGE (serial analysis of gene expression) (Madden, et al., (2000) Drug Discov. Today, 5, 415-425), READS (restriction enzyme amplification of digested cDNAs) (Prashar and Weissman, (1999) *Methods Enzymol.,* 303, 258-72), TOGA (total gene expression analysis) (Sutcliffe, et al., (2000) *Proc. Natl. Acad. Sci. U.S.A.,* 97, 1976-81), protein arrays and proteomics (Celis, et al., (2000) *FEBS Lett.,* 480, 2-16; Jungblut, et al., Electrophoresis, 1999, 20, 2100-10), expressed sequence tag (EST) sequencing (Celis, et al., FEBS Lett., 2000, 480, 2-16; Larsson, et al., J. Biotechnol., 2000, 80, 143-57), subtractive RNA fingerprinting (SuRF) (Fuchs, et al., (2000) Anal. Biochem. 286, 91-98; Larson, et al., (2000) *Cytometry* 41, 203-208), subtractive cloning, differential display (DD) (Jurecic and Belmont, (2000) *Curr. Opin. Microbiol.* 3, 316-21), comparative genomic hybridization (Carulli, et al., (1998) *J. Cell Biochem. Suppl.,* 31, 286-96), FISH (fluorescent in situ hybridization) techniques (Going and Gusterson, (1999) *Eur. J. Cancer,* 35, 1895-904) and mass spectrometry methods (To, Comb. (2000) *Chem. High Throughput Screen,* 3, 235-41).

The compounds of the invention are useful for research and diagnostics, because these compounds hybridize to nucleic acids encoding a Sirtuin (SIRT). For example, oligonucleotides that hybridize with such efficiency and under such conditions as disclosed herein as to be effective Sirtuin (SIRT) modulators are effective primers or probes under conditions favoring gene amplification or detection, respectively. These primers and probes are useful in methods requiring the specific detection of nucleic acid molecules encoding a Sirtuin (SIRT) and in the amplification of said nucleic acid molecules for detection or for use in further studies of a Sirtuin (SIRT). Hybridization of the antisense oligonucleotides, particularly the primers and probes, of the invention with a nucleic acid encoding a Sirtuin (SIRT) can be detected by means known in the art. Such means may include conjugation of an enzyme to the oligonucleotide, radiolabeling of the oligonucleotide, or any other suitable detection means. Kits using such detection means for detecting the level of a Sirtuin (SIRT) in a sample may also be prepared.

The specificity and sensitivity of antisense are also harnessed by those of skill in the art for therapeutic uses. Antisense compounds have been employed as therapeutic moieties in the treatment of disease states in animals, including humans. Antisense oligonucleotide drugs have been safely and effectively administered to humans and numerous clinical trials are presently underway. It is thus established that antisense compounds can be useful therapeutic modalities that can be configured to be useful in treatment regimes for the treatment of cells, tissues and animals, especially humans.

For therapeutics, an animal, preferably a human, suspected of having a disease or disorder which can be treated by modulating the expression of a Sirtuin (SIRT) polynucleotide is treated by administering antisense compounds in accordance with this invention. For example, in one non-limiting embodiment, the methods comprise the step of administering to the animal in need of treatment, a therapeutically effective amount of a Sirtuin (SIRT) modulator. The Sirtuin (SIRT) modulators of the present invention effectively modulate the activity of a Sirtuin (SIRT) or modulate the expression of a Sirtuin (SIRT) protein. In one embodiment, the activity or expression of a Sirtuin (SIRT) in an animal is inhibited by about 10% as compared to a control. Preferably, the activity or expression of a Sirtuin (SIRT) in an animal is inhibited by about 30%. More preferably, the activity or expression of a Sirtuin (SIRT) in an animal is inhibited by 50% or more. Thus, the oligomeric compounds modulate expression of a Sirtuin (SIRT) mRNA by at least 10%, by at least 50%, by at least 25%, by at least 30%, by at least 40%, by at least 50%, by at least 60%, by at least 70%, by at least 75%, by at least 80%, by at least 85%, by at least 90%, by at least 95%, by at least 98% by east 99%, or by 100% as compared to a control.

In one embodiment, the activity or expression of a Sirtuin (SIRT) and/or in an animal is increased by about 10% as compared to a control. Preferably, the activity or expression of a Sirtuin (SIRT) in an animal is increased by about 30%. More preferably, the activity or expression of a Sirtuin (SIRT) in an animal is increased by 50% or more. Thus, the oligomeric compounds modulate expression of a Sirtuin (SIRT) mRNA by at least 10%, by at least 50%, by at least 25%, by at least 30%, by at least 40%, by at least 50%, by at least 60%, by at least 70%, by at least 75%, by at least 80%, by at least 85%, by at least 90%, by at least 95%, by at least 98%, by at least 99%, or by 100% as compared to a control.

For example, the reduction of the expression of a Sirtuin (SIRT) may be measured in serum, blood, adipose tissue, liver or any other body fluid, tissue or organ of the animal. Preferably, the cells contained within said fluids, tissues or organs being analyzed contain a nucleic acid molecule encoding Sirtuin (SIRT) peptides and/or the Sirtuin (SIRT) protein itself.

The compounds of the invention can be utilized in pharmaceutical compositions by adding an effective amount of a compound to a suitable pharmaceutically acceptable diluent or carrier. Use of the compounds and methods of the invention may also be useful prophylactically.

Conjugates:

Another modification of the oligonucleotides of the invention involves chemically linking to the oligonucleotide one or more moieties or conjugates that enhance the activity cellular distribution or cellular uptake of the oligonucleotide. These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application No. PCT/US92/09196, filed Oct. 23, 1992, and U.S. Pat. No. 6,287,860, which are incorporated herein by reference. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-Hphosphonate, a polyamine or a polyethylene glycol chain, or adamantane acetic acid, a palmityl moiety, or an octadecylamine or hexylamino-carbonyl-oxycholesterol moiety. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic.

Representative United States patents that teach the preparation of such oligonucleotides conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

Formulations:

The compounds of the invention may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,165; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

Although, the antisense oligonucleotides do not need to be administered in the context of a vector in order to modulate a target expression and/or function, embodiments of the invention relates to expression vector constructs for the expression of antisense oligonucleotides, comprising promoters, hybrid promoter gene sequences and possess a strong constitutive promoter activity, or a promoter activity which can be induced in the desired case.

In an embodiment, invention practice involves administering at least one of the foregoing antisense oligonucleotides with a suitable nucleic acid delivery system. In one embodiment, that system includes a non-viral vector operably linked to the polynucleotide. Examples of such nonviral vectors include the oligonucleotide alone (e.g. any one or more of SEQ ID NOS: 15 to 94) or in combination with a suitable protein, polysaccharide or lipid formulation.

Additionally suitable nucleic acid delivery systems include viral vector, typically sequence from at least one of an adenovirus, adenovirus-associated virus (AAV), helper-dependent adenovirus, retrovirus, or hemagglutinatin virus of Japan-liposome (HVJ) complex. Preferably, the viral vector comprises a strong eukaryotic promoter operably linked to the polynucleotide e.g., a cytomegalovirus (CMV) promoter.

Additionally vectors include viral vectors, fusion proteins and chemical conjugates. Retroviral vectors include Moloney murine leukemia viruses and HIV-based viruses. One HIV-based viral vector comprises at least two vectors wherein the gag and pol genes are from an HIV genome and the env gene is from another virus. DNA viral vectors are preferred. These vectors include pox vectors such as orthopox or avipox vectors, herpesvirus vectors such as a herpes simplex I virus (HSV) vector, Adenovirus Vectors and Adeno-associated Virus Vectors).

The antisense compounds of the invention encompass any pharmaceutically acceptable salts, esters, or salts of such esters, or any other compound which, upon administration to an animal, including a human, is capable of providing (directly or indirectly) the biologically active metabolite or residue thereof.

The term "pharmaceutically acceptable salts" refers to physiologically and pharmaceutically acceptable salts of the compounds of the invention: i.e., salts that retain the desired biological activity of the parent compound and do not impart undesired toxicological effects thereto. For oligonucleotides, examples of pharmaceutically acceptable salts and their uses are further described in U.S. Pat. No. 6,287,860, which is incorporated herein by reference.

The present invention also includes pharmaceutical compositions and formulations that include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

For treating tissues in the central nervous system, administration can be made by, e.g., injection or infusion into the cerebrospinal fluid. Administration of antisense RNA into cerebrospinal fluid is described, e.g., in U.S. Pat. App. Pub. No. 2007/0117772, "Methods for slowing familial ALS disease progression," incorporated herein by reference in its entirety.

When it is intended that the antisense oligonucleotide of the present invention be administered to cells in the central nervous system, administration can be with one or more agents capable of promoting penetration of the subject antisense oligonucleotide across the blood-brain barrier. Injection can be made, e.g., in the entorhinal cortex or hippocampus. Delivery of neurotrophic factors by administration of an adenovirus vector to motor neurons in muscle tissue is described in, e.g., U.S. Pat. No. 6,632,427, "Adeno-viral-vector-mediated gene transfer into medullary motor neurons," incorporated herein by reference. Delivery of vectors directly to the brain, e.g., the striatum, the thalamus, the hippocampus, or the substantia nigra, is known in the art and described, e.g., in U.S. Pat. No. 6,756,523, "Adenovirus vectors for the transfer of foreign genes into cells of the central nervous system particularly in brain," incorporated herein by reference. Administration can be rapid as by injection or made over a period of time as by slow infusion or administration of slow release formulations.

The subject antisense oligonucleotides can also be linked or conjugated with agents that provide desirable pharmaceutical or pharmacodynamic properties. For example, the antisense oligonucleotide can be coupled to any substance, known in the art to promote penetration or transport across the blood-brain barrier, such as an antibody to the transferrin receptor, and administered by intravenous injection. The antisense compound can be linked with a viral vector, for example, that makes the antisense compound more effective and/or increases the transport of the antisense compound across the blood-brain barrier. Osmotic blood brain barrier disruption can also be accomplished by, e.g., infusion of sugars including, but not limited to, meso erythritol, xylitol, D(+) galactose, D(+) lactose, D(+) xylose, dulcitol, myo-inositol, L(−) fructose, D(−) mannitol, D(+) glucose, D(+) arabinose, D(−) arabinose, cellobiose D(+) maltose, D(+) raffinose, L(+) rhamnose, D(+) melibiose, D(−) ribose, adonitol, D(+) arabitol, L(−) arabitol, D(+) fucose, L(−) fucose, D(−) lyxose, L(+) lyxose, and L(−) lyxose, or amino acids including, but not limited to, glutamine, lysine, arginine, asparagine, aspartic acid, cysteine, glutamic acid, glycine, histidine, leucine, methionine, phenylalanine, proline, serine, threonine, tyrosine, valine, and taurine. Methods and materials for enhancing blood brain barrier penetration are described, e.g., in U.S. Pat. No. 4,866,042, "Method for the delivery of genetic material across the blood brain barrier," U.S. Pat. No. 6,294,520, "Material for passage through the blood-brain barrier," and U.S. Pat. No. 6,936,589, "Parenteral delivery systems," all incorporated herein by reference in their entirety.

The subject antisense compounds may be admixed, encapsulated, conjugated or otherwise associated with other molecules, molecule structures or mixtures of compounds, for example, liposomes, receptor-targeted molecules, oral, rectal, topical or other formulations, for assisting in uptake, distribution and/or absorption. For example, cationic lipids may be included in the formulation to facilitate oligonucleotide uptake. One such composition shown to facilitate uptake is LIPOFECTIN (available from GIBCO-BRL, Bethesda, Md.).

Oligonucleotides with at least one 2'-O-methoxyethyl modification are believed to be particularly useful for oral administration. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

Pharmaceutical compositions of the present invention include, but are not limited to, solutions, emulsions, foams and liposome-containing formulations. The pharmaceutical compositions and formulations of the present invention may comprise one or more penetration enhancers, carriers, excipients or other active or inactive ingredients.

Emulsions are typically heterogeneous systems of one liquid dispersed in another in the form of droplets usually exceeding 0.1 µm in diameter. Emulsions may contain additional components in addition to the dispersed phases, and the active drug that may be present as a solution in either the aqueous phase, oily phase or itself as a separate phase. Microemulsions are included as an embodiment of the present invention. Emulsions and their uses are well known in the art and are further described in U.S. Pat. No. 6,287,860.

Formulations of the present invention include liposomal formulations. As used in the present invention, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes that are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes also include "sterically stabilized" liposomes, a term which, as used herein, refers to liposomes comprising one or more specialized lipids. When incorporated into liposomes, these specialized lipids result in liposomes with enhanced circulation lifetimes relative to liposome slacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860.

The pharmaceutical formulations and compositions of the present invention may also include surfactants. The use of surfactants in drug products, formulations and in emulsions is well known in the art. Surfactants and their uses are further described in U.S. Pat. No. 6,287,860, which is incorporated herein by reference.

In one embodiment, the present invention employs various penetration enhancers to effect the efficient delivery of nucleic acids, particularly oligonucleotides. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating nonsurfactants. Penetration enhancers and their uses are further described in U.S. Pat. No. 6,287,860, which is incorporated herein by reference.

One of skill in the art will recognize that formulations are routinely designed according to their intended use, i.e. route of administration.

formulations for topical administration include those in which the oligonucleotides of the invention are in admixture with a topical delivery agent such as lipids, liposomes, fatty acids, fatty acid esters, steroids, chelating agents and surfactants, lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA).

For topical or other administration, oligonucleotides of the invention may be encapsulated within liposomes or may form complexes thereto, in particular to cationic liposomes. Alternatively, oligonuclotides may be complexed to lipids, in particular to cationic lipids, fatty acids and esters, pharmaceutically acceptable salts thereof, and their uses are further described in U.S. Pat. No. 6,287,860.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable, oral formulations are those in which oligonucleotides of the invention are administered in conjunction with one or more penetration enhancers surfactants and chelators, surfactants include fatty acids and/or esters or salts thereof, bile acids and/or salts thereof: bile acids/salts and fatty acids and their uses are further described in U.S. Pat. No. 6,287,860, which is incorporated herein by reference. Also are combinations of penetration enhancers, for example, fatty acids/salts in combination with bile acids/salts. A particularly combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally, in granular form including sprayed dried particles, or complexed to form micro or nanoparticles. Oligonucleotide complexing agents and their uses are further described in U.S. Pat. No. 6,287,860, which is incorporated herein by reference.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Certain embodiments of the invention provide pharmaceutical compositions containing one or more oligomeric compounds and one or more other chemotherapeutic agents that function by a non-antisense mechanism. Examples of such chemotherapeutic agents include but are not limited to cancer chemotherapeutic drugs such as daunorubicin, daunomycin, dactinomycin, doxorubicin epirubicin, idarubicin, esorubicin, bleomycin, mafosfamide, ifosfamide, cytosine arabinoside, bischloroethyl-nitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclo-phosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. Combinations of antisense compounds and other non-antisense drugs are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. For example, the first target may be a particular antisense sequence of a Sirtuin (SIRT), and the second target may be a region from another nucleotide sequence. Alternatively, compositions of the invention may contain two or more antisense compounds targeted to different regions of the same Sirtuin (SIRT) nucleic acid target Numerous examples of antisense compounds are illustrated herein and others may be selected from among suitable compounds known in the art. Two or more combined compounds may be used together or sequentially.

Dosing:

The formulation of therapeutic compositions and their subsequent administration (dosing) is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on EC50s found to be effective in in vivo and in vitro animal models. In general, dosage is from 0.01 µg to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 µg to 100 g per kg of body weight, once or more daily, to once every 20 years.

In embodiments, a patient is treated with a dosage of drug that is at least about 1, at least about 2, at least about 3, at least about 4, at least about 5, at least about 6, at least about 7, at least about 8, at least about 9, at least about 10, at least about 15, at least about 20, at least about 25, at least about 30, at least about 35, at least about 40, at least about 45, at least about 50, at least about 60, at least about 70, at least about 80, at least about 90, or at least about 100 mg/kg body weight. Certain injected dosages of antisense oligonucleotides are described, e.g., in U.S. Pat. No. 7,563,884, "Antisense modulation of PTP1B expression," incorporated herein by reference in its entirety.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments.

All documents mentioned herein are incorporated herein by reference. All publications and patent documents cited in this application are incorporated by reference for all purposes to the same extent as if each individual publication or patent document were so individually denoted. By their citation of various references in this document, Applicants do not admit any particular reference is "prior art" to their invention. Embodiments of inventive compositions and methods are illustrated in the following examples.

EXAMPLES

The following non-limiting Examples serve to illustrate selected embodiments of the invention. It will be appreciated that variations in proportions and alternatives in elements of the components shown will be apparent to those skilled in the art and are within the scope of embodiments of the present invention.

Example 1: Design of Antisense Oligonucleotides Specific for a Nucleic Acid Molecule Antisense to a Sirtuin (SIRT) and/or a Sense Stand of a Sirtuin (SIRT) Polynucleotide As indicated above the term "oligonucleotide specific for" or "oligonucleotide targets" refers to an oligonucleotide having a sequence (i) capable of forming a stable complex with a portion of the targeted gene, or (ii) capable of forming a stable duplex with a portion of an mRNA transcript of the targeted gene.

Selection of appropriate oligonucleotides is facilitated by using computer programs that automatically align nucleic acid sequences and indicate regions of identity or homology. Such programs are used to compare nucleic acid sequences obtained, for example, by searching databases such as GenBank or by sequencing PCR products. Comparison of nucleic acid sequences from a range of species allows the selection of nucleic acid sequences that display an appropriate degree of identity between species. In the case of genes that have not been sequenced, Southern blots are performed to allow a determination of the degree of identity between genes in target species and other species. By performing Southern blots at varying degrees of stringency, as is well known in the art, it is possible to obtain an approximate measure of identity. These procedures allow the selection of oligonucleotides that exhibit a high degree of complementarity to target nucleic acid sequences in a subject to be controlled and a lower degree of complementarity to corresponding nucleic acid sequences in other species. One skilled in the art will realize that there is considerable latitude in selecting appropriate regions of genes for use in the present invention.

An antisense compound is "specifically hybridizable" when binding of the compound to the target nucleic acid interferes with the normal function of the target nucleic acid to cause a modulation of function and/or activity, and there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

The hybridization properties of the oligonucleotides described herein can be determined by one or more in vitro assays as known in the art. For example, the properties of the oligonucleotides described herein can be obtained by determination of binding strength between the target natural antisense and a potential drug molecules using melting curve assay.

The binding strength between the target natural antisense and a potential drug molecule (Molecule) can be estimated using any of the established methods of measuring the strength of intermolecular interactions, for example, a melting curve assay.

Melting curve assay determines the temperature at which a rapid transition from double-stranded to single-stranded conformation occurs for the natural antisense/Molecule complex. This temperature is widely accepted as a reliable measure of the interaction strength between the two molecules.

A melting curve assay can be performed using a cDNA copy of the actual natural antisense RNA molecule or a synthetic DNA or RNA nucleotide corresponding to the binding site of the Molecule. Multiple kits containing all necessary reagents to perform this assay are available (e.g. Applied Biosystems Inc. MeltDoctor kit). These kits include a suitable buffer solution containing one of the double strand DNA (dsDNA) binding dyes (such as ABI HRM dyes, SYBR Green, SYTO, etc.). The properties of the dsDNA dyes are such that they emit almost no fluorescence in free form, but are highly fluorescent when bound to dsDNA.

To perform the assay the cDNA or a corresponding oligonucleotide are mixed with Molecule in concentrations defined by the particular manufacturer's protocols. The mixture is heated to 95° C. to dissociate all pre-formed dsDNA complexes, then slowly cooled to room temperature or other lower temperature defined by the kit manufacturer to allow the DNA molecules to anneal. The newly formed complexes are then slowly heated to 95° C. with simultaneous continuous collection of data on the amount of fluorescence that is produced by the reaction. The fluorescence intensity is inversely proportional to the amounts of dsDNA present in the reaction. The data can be collected using a real time PCR instrument compatible with the kit (e.g. ABI's StepOne Plus Real Time PCR System or Light-Typer instrument, Roche Diagnostics, Lewes, UK).

Melting peaks are constructed by plotting the negative derivative of fluorescence with respect to temperature (−d (Fluorescence)/dT) on the y-axis) against temperature (x-axis) using appropriate software (for example LightTyper (Roche) or SDS Dissociation Curve, ABI). The data is analyzed to identify the temperature of the rapid transition from dsDNA complex to single strand molecules. This temperature is called Tm and is directly proportional to the strength of interaction between the two molecules. Typically, Tm will exceed 40° C.

Example 2: Modulation of SIRT Polynucleotide

Treatment of HepG2 Cells with Antisense Oligonucleotides

HepG2 cells from ATCC (cat #HB-8065) were grown in growth media (MEM/EBSS (Hyclone cat #SH30024, or Mediatech cat #MT-10-010-CV)+10% FBS (Mediatech cat #MT35-011-CV)+penicillin/streptomycin (Mediatech cat #MT30-002-CI)) at 37° C. and 5% $CO_2$. One day before the experiment the cells were replated at the density of 1.5× $10^5$/ml into 6 well plates and incubated at 37° C. and 5% $CO_2$. On the day of the experiment the media in the 6 well plates was changed to fresh growth media. All antisense oligonucleotides were diluted to the concentration of 20 μM. Two μl of this solution was incubated with 400 μl of Opti-MEM media (Gibco cat #31985-070) and 4 μl of Lipofectamine 2000 (Invitrogen cat #11668019) at room temperature for 20 min and applied to each well of the 6 well plates with HepG2 cells. A Similar mixture including 2 μl of water instead of the oligonucleotide solution was used for the mock-transfected controls. After 3-18 h of incubation at 37° C. and 5% $CO_2$ the media was changed to fresh growth media. 48 h after addition of antisense oligonucleotides the media was removed and RNA was extracted from the cells using SV Total RNA Isolation System from Promega (cat #Z3105) or RNeasy Total RNA Isolation kit from Qiagen (cat #74181) following the manufacturers' instructions. 600 ng of RNA was added to the reverse transcription reaction performed using Verso cDNA kit from Thermo Scientific (cat #AB1453B) or High Capacity cDNA Reverse Transcription Kit (cat #4368813) as described in the manufacturer's protocol. The cDNA from this reverse transcription reaction was used to monitor gene expression by real time PCR using ABI Taqman Gene Expression Mix (cat #4369510) and primers/probes designed by ABI (Applied Biosystems Taqman Gene Expression Assay: Hs00202021_m1, Hs00202030_m1 and Hs00213036_m1 by Applied Biosystems Inc., Foster City Calif.). The following PCR cycle was used: 50° C. for 2 min, 95° C. for 10 min, 40 cycles of (95° C. for 15 seconds, 60° C. for 1 min) using StepOne Plus Real Time PCR Machine (Applied Biosystems).

Fold change in gene expression after treatment with antisense oligonucleotides was calculated based on the difference in 18S-normalized dCt values between treated and mock-transfected samples.

Figure 3:
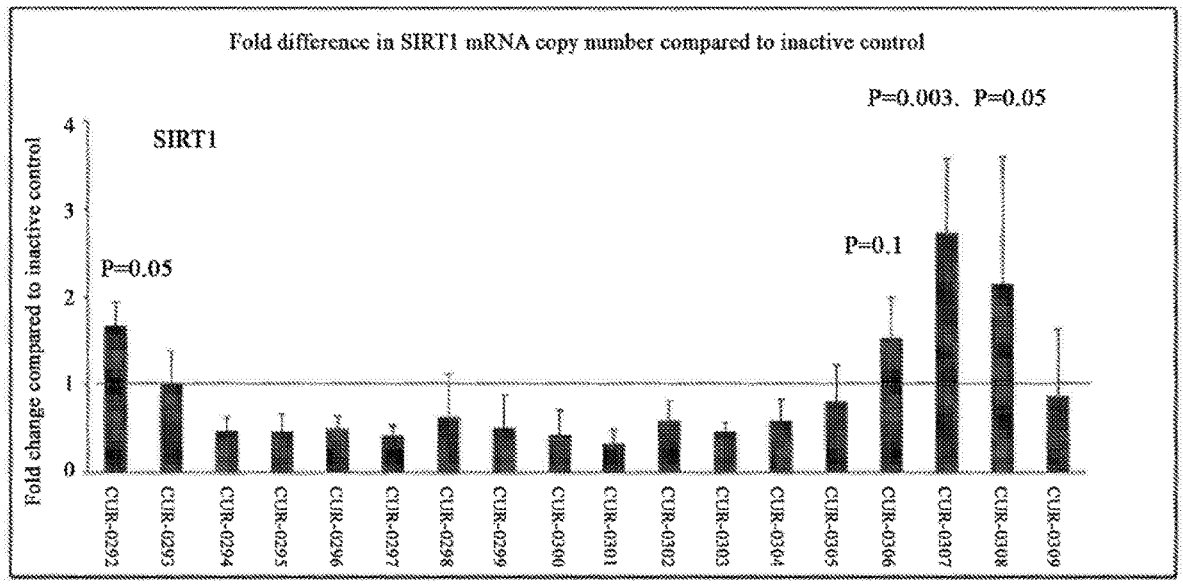
FIG. 3 shows results for the oligonucleotide walk across the SIRT antisense. Real time PCR results show that the levels of the SIRT1 mRNA in HepG2 cells are significantly increased 48 h after treatment with three of the antisense oligonucleotides designed to sirtas. CUR-0292 to CUR-0309 correspond to SEQ ID NOs: 15 to 32 respectively.
Figure 4:
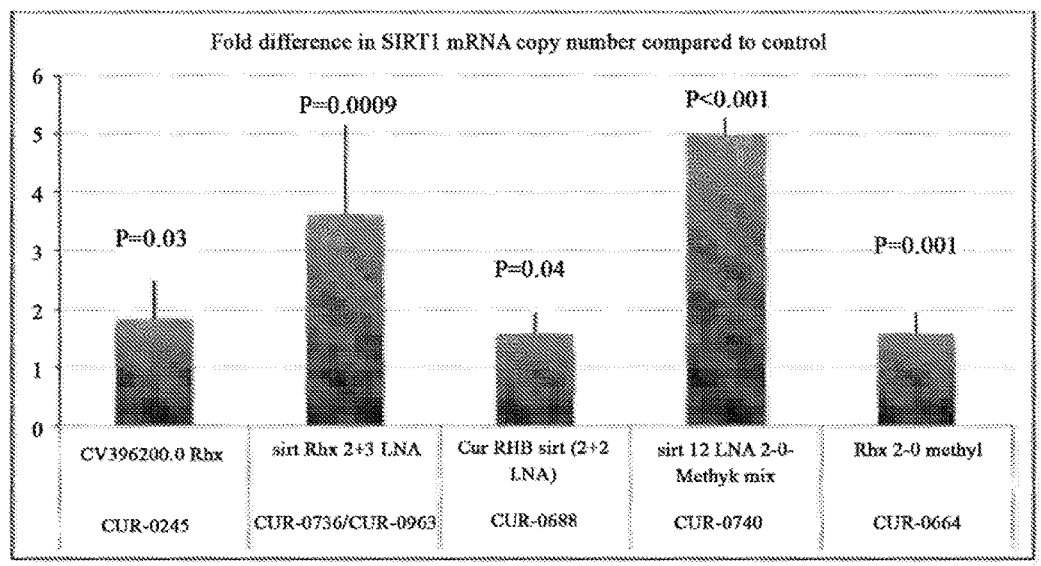
FIGS. 4 and 5 show results for PS, LNA and 2'O Me Modified oligonucleotides in HepG2 (FIG. 4) and Vero76 (FIG. 5) cells. Real time PCR results show that the levels of the SIRT1 mRNA in HepG2 cells are significantly increased 48 b after treatment with PS, LNA, 2'O Me and 2'O Me mixmer designed antisense oligonucleotides to SIRT1 antisense. Levels of SIRT1 mRNA in Vero cells also increased 48 hours after treatment with PS and LNA modified antisense oligonucleotides to SIRT1 antisense. Bars denoted as CUR-0245, CUR-0736, CUR 0688, CUR-0740 and CUR-0664 correspond to SEQ ID NOs: 33 to 37 respectively.

Results:

Real time PCR results show that the levels of the SIRT1 mRNA in HepG2 cells significantly increased 48 h after treatment with some antisense oligonucleotides to SIRT1 antisense CV396200 (FIGS. 3, 4).

Figure 8:
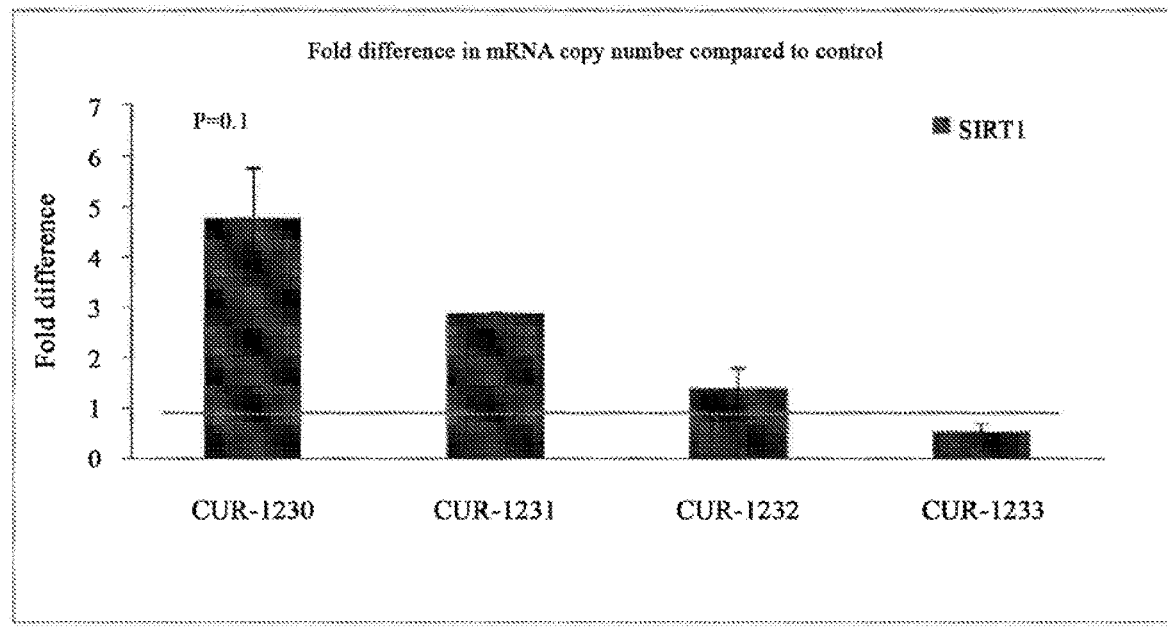
FIG. 8 shows results for oligonucleotides designed to SIRT antisense CV396200. Real Time PCR results show that levels of SIRT1 mRNA in HepG2 cells are significantly increased in one of the oligonucleotides designed to SIRT1 antisense CV396200. The bars denoted as CUR-1230, CUR-1231, CUR-1232 and CUR-1233 correspond to SEQ ID NOs: 41 to 44.

Real Time PCR results show that levels of SIRT1 mRNA in HepG2 cells are significantly increased in one of the oligonucleotides designed to SIRT1 antisense CV396200 (FIG. 8).

Figure 9:
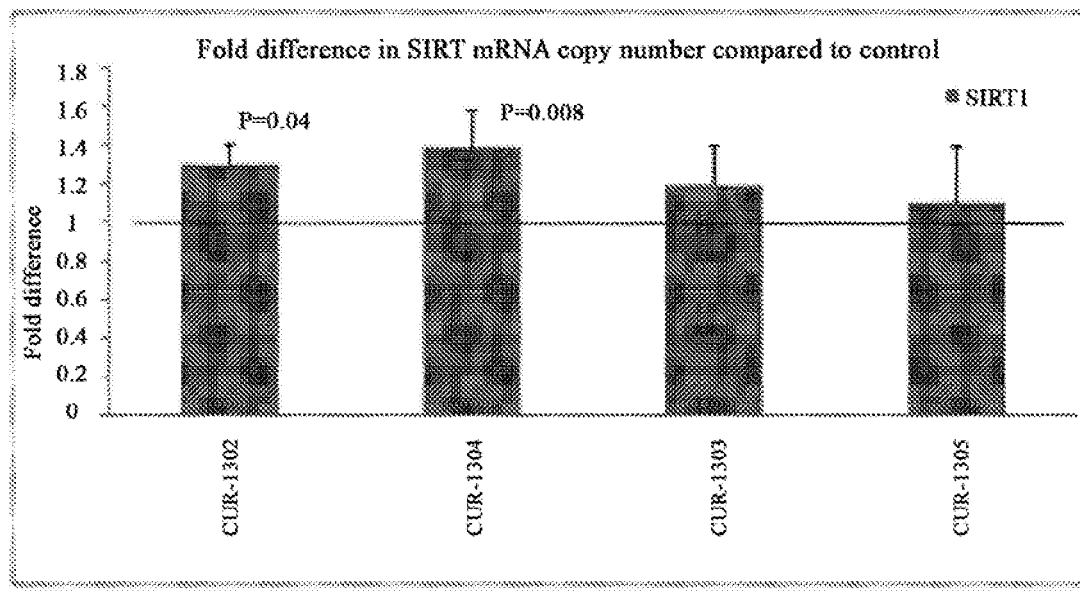
FIG. 9 shows results for oligonucleotides designed to SIRT antisense CV428275. Real Time PCR results show that levels of SIRT1 mRNA in HepG2 cells are significantly increased in two of the oligonucleotides designed to SIRT1 antisense CV428275. The bars denoted as CUR-1302, CUR-1304, CUR-1303 and CUR-1305 correspond to SEQ ID NOs: 45 to 48.

Real Time PCR results show that levels of SIRT1 mRNA in HepG2 cells are significantly increased in two of the oligonucleotides designed to SIRT1 antisense CV428275 (FIG. 9).

Figure 10:
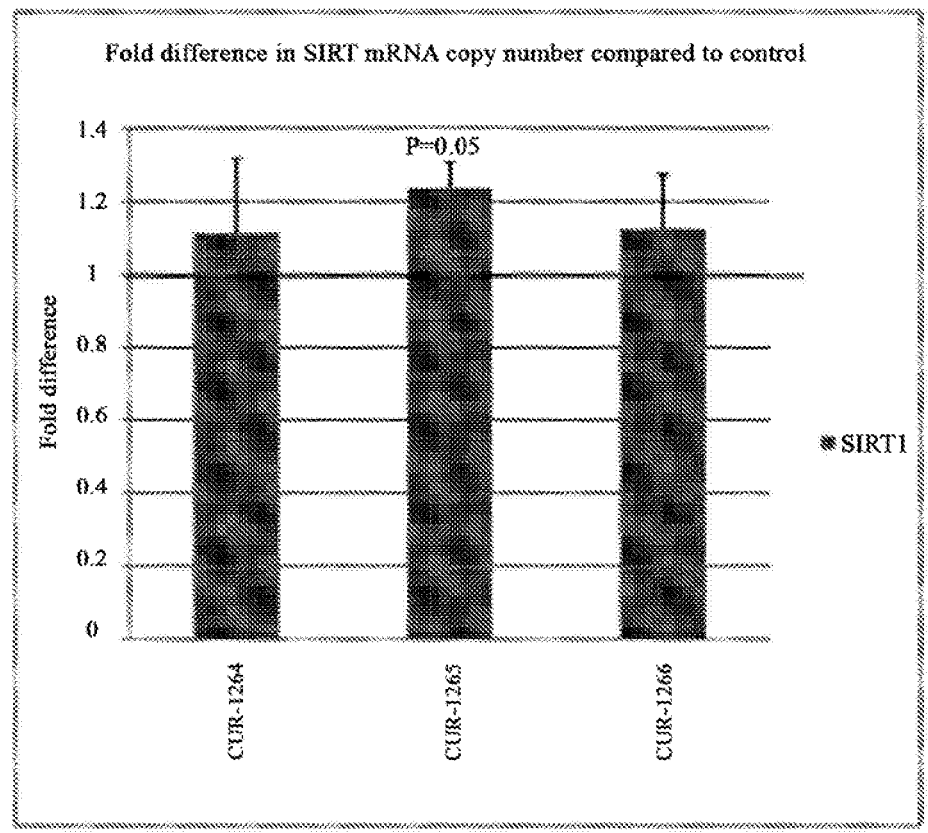
FIG. 10 shows Real time PCR results. The results show that a significant increase in SIRT1 mRNA levels in HepG2 cells 48 hours after treatment with one of the oligonucleotides designed to SIRT antisense BE717453. The bars denoted as CUR-1264, CUR1265 and CUR-1266 correspond to SEQ ID NOs: 49 to 51 respectively.

The results show that a significant increase in SIRT1 mRNA levels in HepG2 cells 48 hours after treatment with one of the oligonucleotides designed to SIRT antisense BE717453. (FIG. 10).

Figure 11:
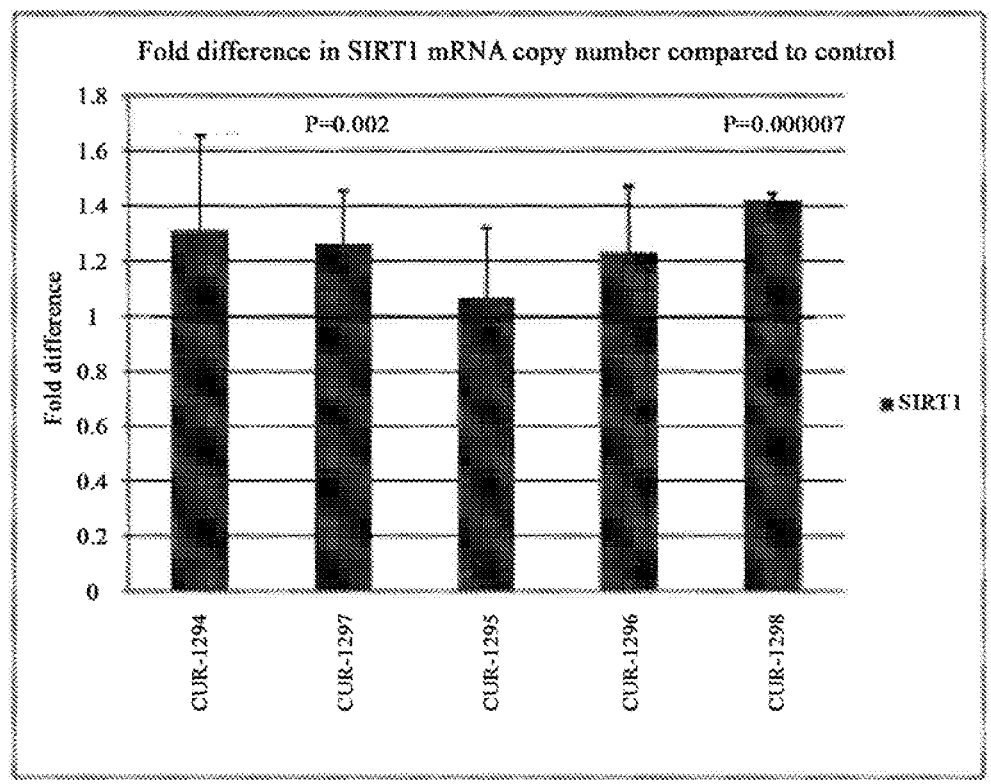
FIG. 11 shows Real time PCR results. The results show that show that the levels of the SIRT1 mRNA in HepG2 cells are significantly increased 48 h after treatment with three of the oligonucleotides designed to SIRT1 antisense AV718812. The bars denoted as CUR-1294, CUR-1297, CUR-1295, CUR-1296 and CUR-1298 correspond to SEQ ID NOs: 52 to 56 respectively.

The results show that show that the levels of the SIRT1 mRNA in HepG2 cells are significantly increased 48 h after treatment with three of the oligonucleotides designed to SIRT1 antisense AV718812 respectively (FIG. 11).

Figure 12:
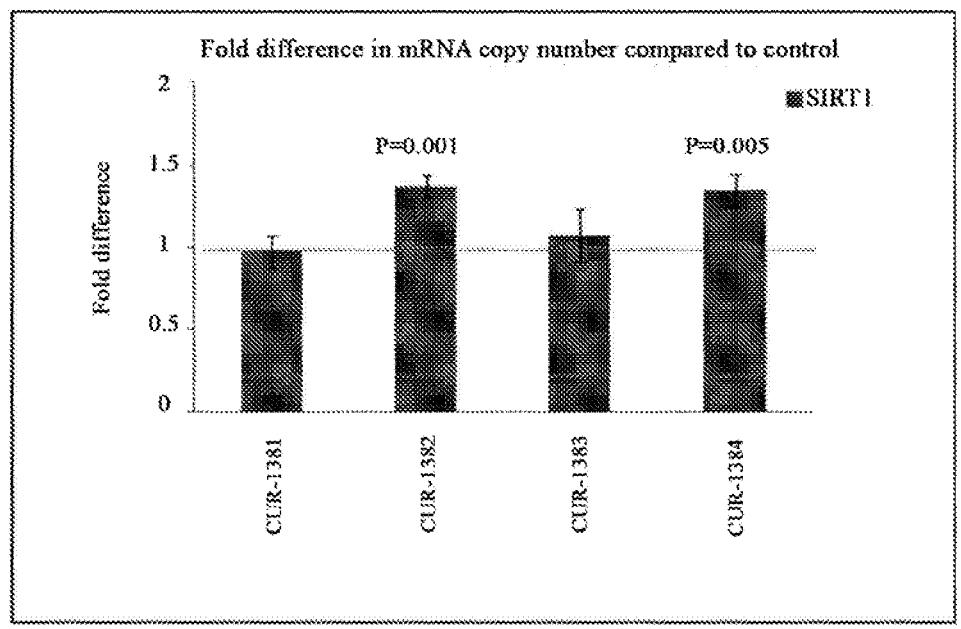
FIG. 12 is a graph of real time PCR results showing the fold change+standard deviation in SIRT1 mRNA after treatment of HepG2 cells with phosphorothioate oligonucleotides introduced using Lipofectamine 2000, as compared to control. Real time PCR results show that the levels of SIRT1 mRNA are significantly increased in HepG2 cells 48 h after treatment with two of the oligos designed to SIRT1 antisense AW169958. Bars denoted as CUR-1381, CUR-1382, CUR-1383 and CUR-1384 correspond to samples treated with SEQ ID NOS: 57 to 60 respectively.

Real time PCR results show that the levels of SIRT1 mRNA in HepG2 cells are significantly increased 48 h after treatment with two of the oligos designed to SIRT1 antisense AW169958 (FIG. 12).

Figure 17:
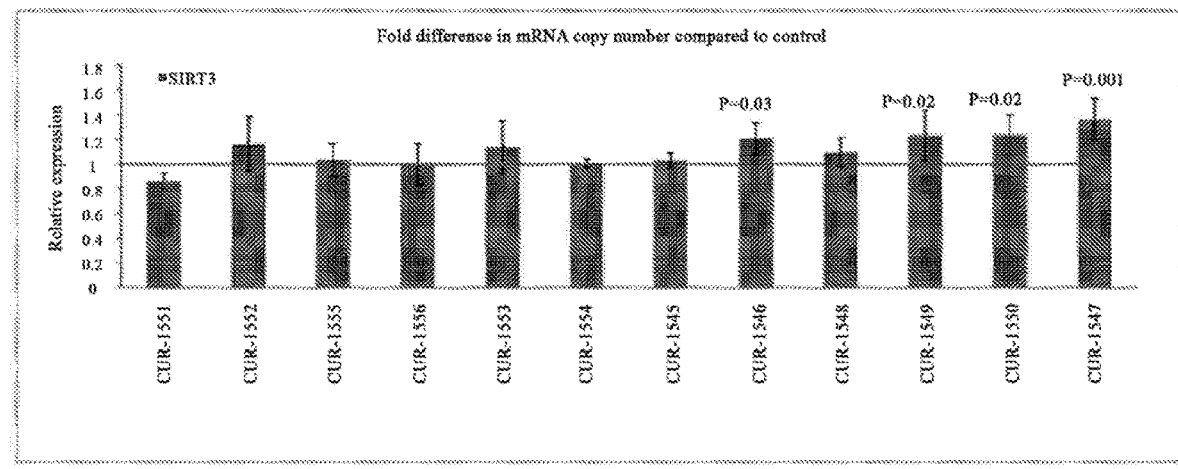
FIG. 17 is a graph of real time PCR results showing the fold change+standard deviation in Sirtuin3 mRNA after treatment of HepG2 cells with phosphorothioate oligonucleotides introduced using Lipofectamine 2000, as compared to control. RT PCR results show that sirt3 levels in HepG2 cells are increased 48 hours after treatment with phosphorothioate antisense oligonucleotides designed to sirt3 antisense Hs.683117 (CUR-1545-1550). Bars denoted as CUR-0551, CUR-1552, CUR-1555, CUR-1556, CUR-1553, CUR-1554, CUR-1545, CUR-1546, CUR-1548, CUR-1549, CUR-1550 and CUR-1547, correspond to samples treated with SEQ ID NOS: 73 to 84 respectively.

RT PCR results show that sirt3 levels in HepG2 cells are increased 48 hours after treatment with phosphorothioate antisense oligonucleotides designed to sirt3 antisense Hs.683117 (CUR-1545-1550) (FIG. 17).

Figure 18:
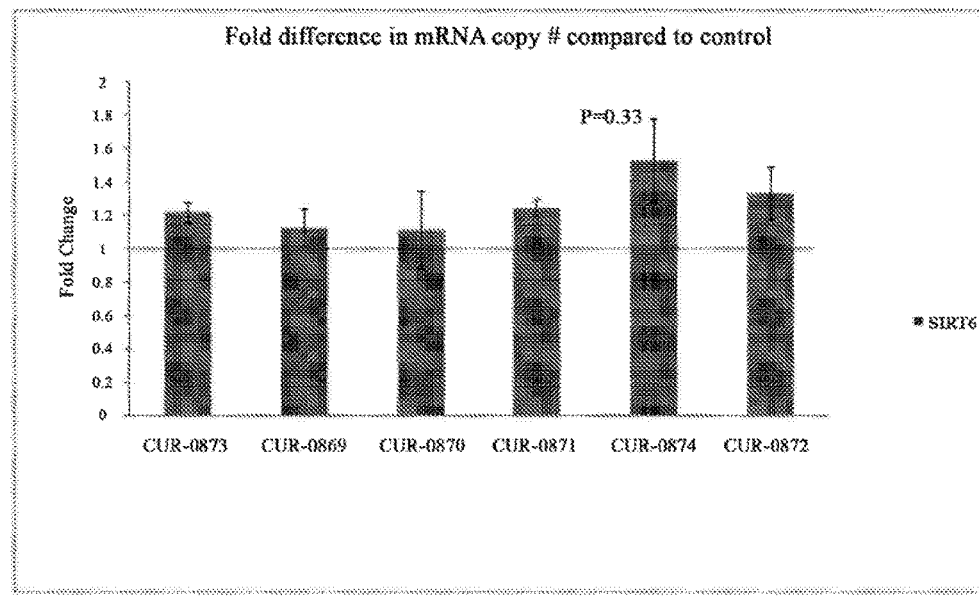
FIG. 18 is a graph of real time PCR results showing the fold change+standard deviation in SIRT6 mRNA after treatment of HepG2 cells with phosphorothioate oligonucleotides introduced using Lipofectamine 2000, as compared to control. Real time PCR results show that the levels of SIRT6 mRNA in HepG2 cells are significantly increased 48 h after treatment with one of the oligos designed to SIRT6 antisense NM_133475. Bars denoted as CUR-0873, CUR-0869 to CUR-0871, CUR-0874 and CUR-0872, correspond to samples treated with SEQ ID NOS: 85 to 90 respectively.

Real time PCR results show that the levels of SIRT6 mRNA in HepG2 cells are significantly increased 48 h after treatment with one of the oligos designed to SIRT6 antisense NM_133475 (FIG. 18).

Figure 19:
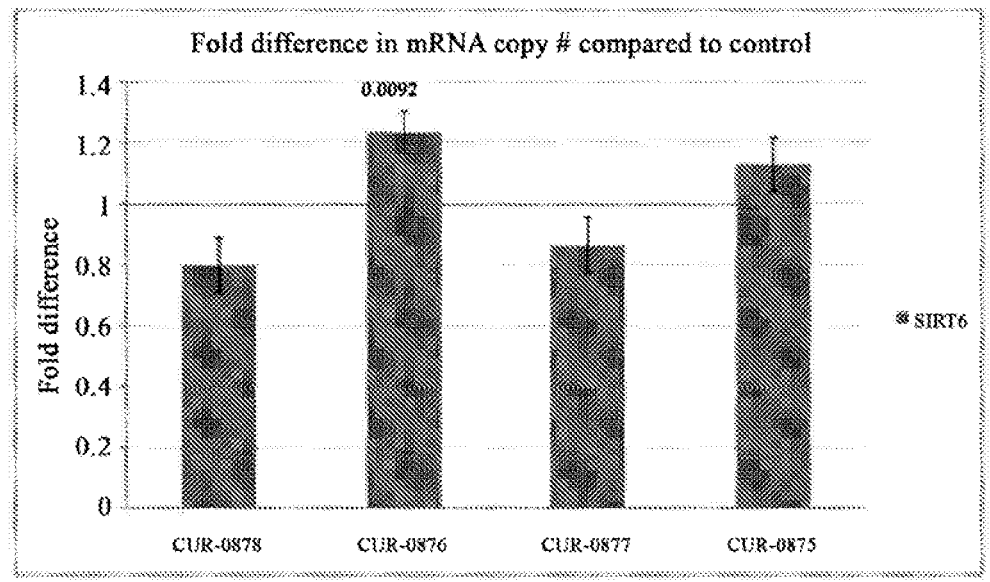
FIG. 19 is a graph of real time PCR results showing the fold change+standard deviation in SIRT6 mRNA after treatment of HepG2 cells with phosphorothioate oligonucleotides introduced using Lipofectamine 2000, as compared to control. Real time PCR results show that the levels of SIRT6 mRNA in HepG2 cells are significantly increased 48 h after treatment with one of the oligos designed to SIRT6 antisense bf772662. Bars denoted as CUR-0878, CUR-0876, CUR-0877 and CUR-0875, correspond to samples treated with SEQ ID NOS: 91 to 94 respectively.

Real time PCR results show that the levels of SIRT6 mRNA in HepG2 cells are significantly increased 48 h after treatment with one of the oligos designed to SIRT6 antisense bf772662 (FIG. 19)

Treatment of 3T3 Cells with Antisense Oligonucleotides

3T3 cells from ATCC (cat #CRL-1658) were grown in growth media (MEM/EBSS (Hyclone cat #SH30024, or Mediatech cat #MT-10-010-CV)+10% FBS (Mediatech cat #MT35-011-CV)+penicillin/streptomycin (Mediatech cat #MT30-002-CI)) at 37° C. and 5% $CO_2$. One day before the experiment the cells were replated at the density of 1.5× $10^5$/ml into 6 well plates and incubated at 37° C. and 5% $CO_2$. On the day of the experiment the media in the 6 well plates was changed to fresh growth media. All antisense oligonucleotides were diluted to the concentration of 20 μM. Two μl of this solution was incubated with 400 μl of Opti-MEM media (Gibco cat #31985-070) and 4 μl of Lipofectamine 2000 (Invitrogen cat #11668019) at room temperature for 20 min and applied to each well of the 6 well plates with 3T3 cells. A Similar mixture including 2 μl of water instead of the oligonucleotide solution was used for the mock-transfected controls. After 3-18 h of incubation at 37° C. and 5% $CO_2$ the media was changed to fresh growth media. 48 h after addition of antisense oligonucleotides the media was removed and RNA was extracted from the cells using SV Total RNA Isolation System from Promega (cat #Z3105) or RNeasy Total RNA Isolation kit from Qiagen (cat #74181) following the manufacturers' instructions. 600 ng of RNA was added to the reverse transcription reaction performed using Verso cDNA kit from Thermo Scientific (cat #AB1453B) or High Capacity cDNA Reverse Transcription Kit (cat #4368813) as described in the manufacturer's protocol. The cDNA from this reverse transcription reaction was used to monitor gene expression by real time PCR using ABI Taqman Gene Expression Mix (cat #4369510) and primers/probes designed by ABI (Applied Biosystems Taqman Gene Expression Assay:

Hs00202021_m1 by Applied Biosystems Inc., Foster City Calif.). The following PCR cycle was used: 50° C. for 2 min, 95° C. for 10 min, 40 cycles of (95° C. for 15 seconds, 60° C. for 1 min) using StepOne Plus Real Time PCR Machine (Applied Biosystems).

Fold change in gene expression after treatment with antisense oligonucleotides was calculated based on the difference in 18S-normalized dCt values between treated and mock-transfected samples.

Figure 13:
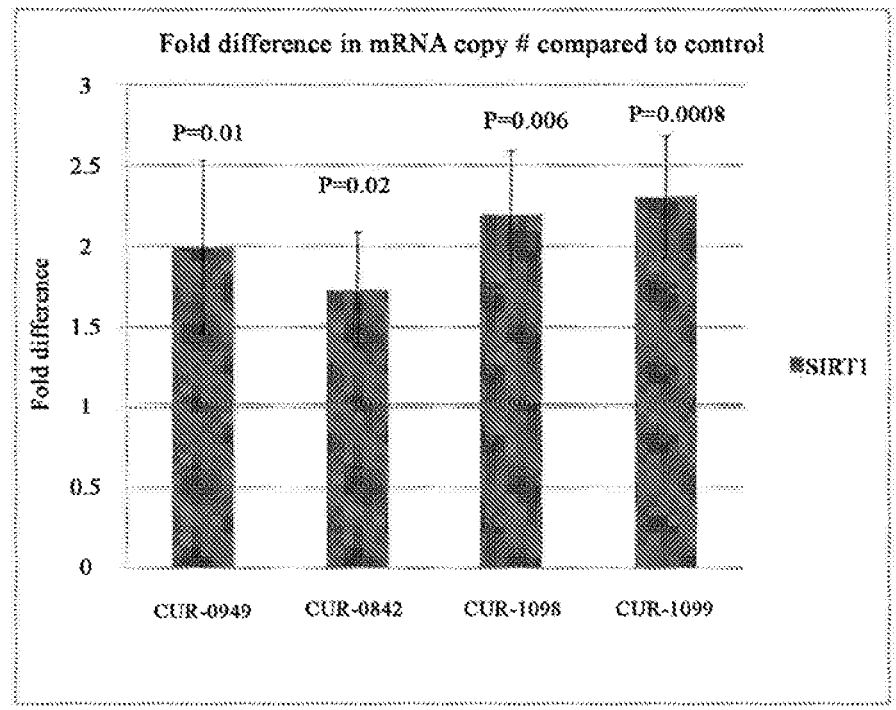
FIG. 13 is a graph of real time PCR results showing the fold change+standard deviation in SIRT1 mRNA after treatment of 3T3 cells with phosphorothioate oligonucleotides introduced using Lipofectamine 2000, as compared to control. Real time PCR results show that the levels of SIRT1 mRNA are significantly increased in 3T3 cells 48 h after treatment with three of the oligonucleotides designed to SIRT1 mouse antisense AK044604. Bars denoted as CUR-0949, CUR-0842, CUR-1098 and CUR-1099 correspond to samples treated with SEQ ID NOS: 67, 61, 71 and 72 respectively.

Results:

Real time PCR results show that the levels of SIRT1 mRNA are significantly increased in 3T3 cells 48 h after treatment with three of the oligonucleotides designed to SIRT1 mouse antisense AK044604 (FIG. 13).

Figure 14:
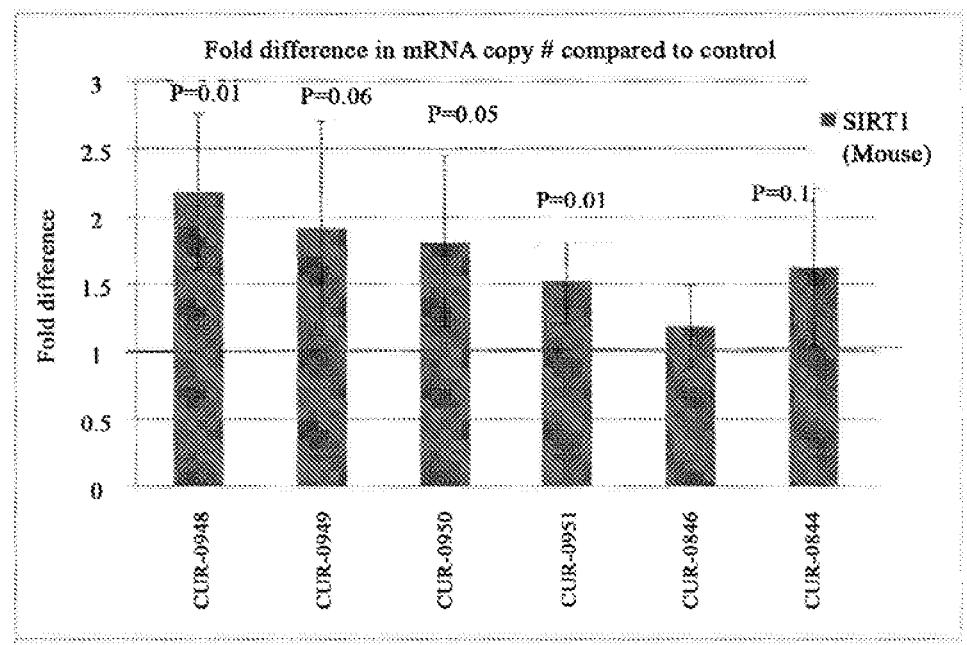
FIG. 14 is a graph of real time PCR results showing the fold change+standard deviation in SIRT1 mRNA after treatment of 3T3 cells with phosphorothioate oligonucleotides introduced using Lipofectamine 2000, as compared to control. Real time PCR results show that the levels of SIRT1 mRNA are significantly increased in 3T3 cells 48 h after treatment with five of the oligonucleotides designed to SIRT1 mouse antisense AK44604. Bars denoted as CUR-0948, CUR-0949, CUR-0950, CUR-0951, CUR-0846, and CUR-0844 correspond to samples treated with SEQ ID NOS: 66 to 69, 65 and 63 respectively.

Real time PCR results show that the levels of SIRT1 mRNA are significantly increased in 3T3 cells 48 h after treatment with five of the oligonucleotides designed to SIRT1 mouse antisense AK044604 (FIG. 14).

Figure 15:
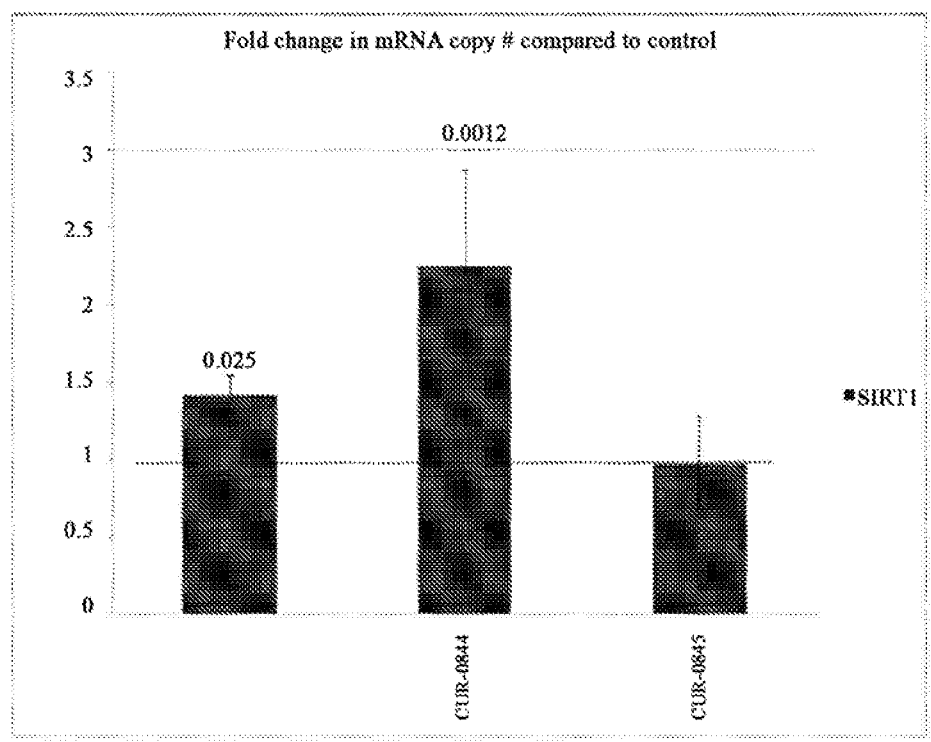
FIG. 15 is a graph of real time PCR results showing the fold change+standard deviation in SIRT1 mRNA after treatment of 3T3 cells with phosphorothioate oligonucleotides introduced using Lipofectamine 2000, as compared to control. Real time PCR results show that the levels of SIRT1 mRNA are significantly increased in HepG2 cells 48 h after treatment with two of the oligonucleotides designed to SIRT1 mouse antisense AK044604. Bars denoted as CUR-0842, CUR-0844, and CUR0845 correspond to samples treated with SEQ ID NOS: 61, 63 and 64 respectively.

Real time PCR results show that the levels of SIRT1 mRNA are significantly increased in 3T3 cells 48 h after treatment with two of the oligonucleotides designed to SIRT1 mouse antisense AK044604 (FIG. 15).

Figure 16:
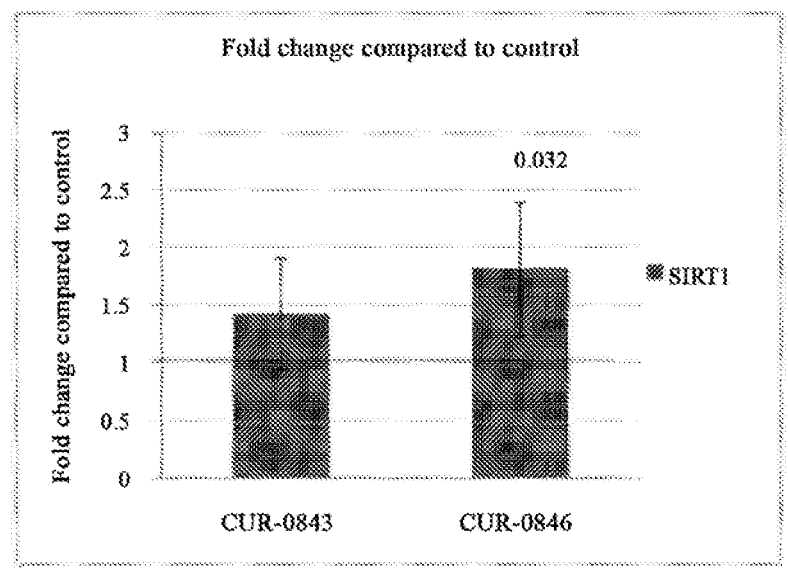
FIG. 16 is a graph of real time PCR results showing the fold change+standard deviation in SIRT1 mRNA after treatment of 3T3 cells with phosphorothioate oligonucleotides introduced using Lipofectamine 2000, as compared to control. Real time PCR results show that the levels of SIRT1 mRNA are significantly increased in HepG2 cells 48 h after treatment with two of the oligonucleotides designed to SIRT1 mouse antisense AK044604. Bars denoted as CUR-0843, CUR-0846 correspond to samples treated with SEQ ID NOS: 62 and 65 respectively.

Real time PCR results show that the levels of SIRT1 mRNA are significantly increased in 3T3 cells 48 h after treatment with two of the oligonucleotides designed to SIRT1 mouse antisense AK044604 (FIG. 16).

Treatment of Vero76 Cells with Antisense Oligonucleotides:

Vero76 cells from ATCC (cat #CRL-1587) were grown in growth media (MEM/EBSS (Hyclone cat #SH30024, or Mediatech cat #MT-10-010-CV)+10% FBS (Mediatech cat #MT35-011-CV)+penicillin/streptomycin (Mediatech cat #MT30-002-CI)) at 37° C. and 5% $CO_2$. One day before the experiment the cells were replated at the density of $1.5 \times 10^5$/ml into 6 well plates and incubated at 37° C. and 5% $CO_2$. On the day of the experiment the media in the 6 well plates was changed to fresh growth media. All antisense oligonucleotides were diluted in water to the concentration of 20 µM. 2 µl of this solution was incubated with 400 µl of Opti-MEM media (Gibco cat #31985-070) and 4 µl of Lipofectamine 2000 (Invitrogen cat #11668019) at room temperature for 20 min and applied to each well of the 6 well plates with Vero76 cells. Similar mixture including 2 µl of water instead of the oligonucleotide solution was used for the mock-transfected controls. After 3-18 h of incubation at 37° C. and 5% CO2 the media was changed to fresh growth media. 48 h after addition of antisense oligonucleotides the media was removed and RNA was extracted from the cells using SV Total RNA Isolation System from Promega (cat #Z3105) or RNeasy Total RNA Isolation kit from Qiagen (cat #74181), following the manufacturers' instructions. 600 ng of RNA was added to the reverse transcription reaction performed using Verso cDNA kit from Thermo Scientific (cat #AB1453B) as described in the manufacturer's protocol. The cDNA from this reverse transcription reaction was used to monitor gene expression by real time PCR using ABI Taqman Gene Expression Mix (cat #4369510) and primers/probes designed by ABI (Applied Biosystems Taqman Gene Expression Assay: Hs00202021_m1 by Applied Biosystems Inc., Foster City Calif.). The following PCR cycle was used: 50° C. for 2 min, 95° C. for 10 min, 40 cycles of (95° C. for 15 seconds, 60° C. for 1 min) using StepOne Plus Real Time PCR Machine (Applied Biosystems). Fold change in gene expression after treatment with antisense oligonucleotides was calculated based on the difference in 18S-normalized dCt values between treated and mock-transfected samples.

Figure 5:
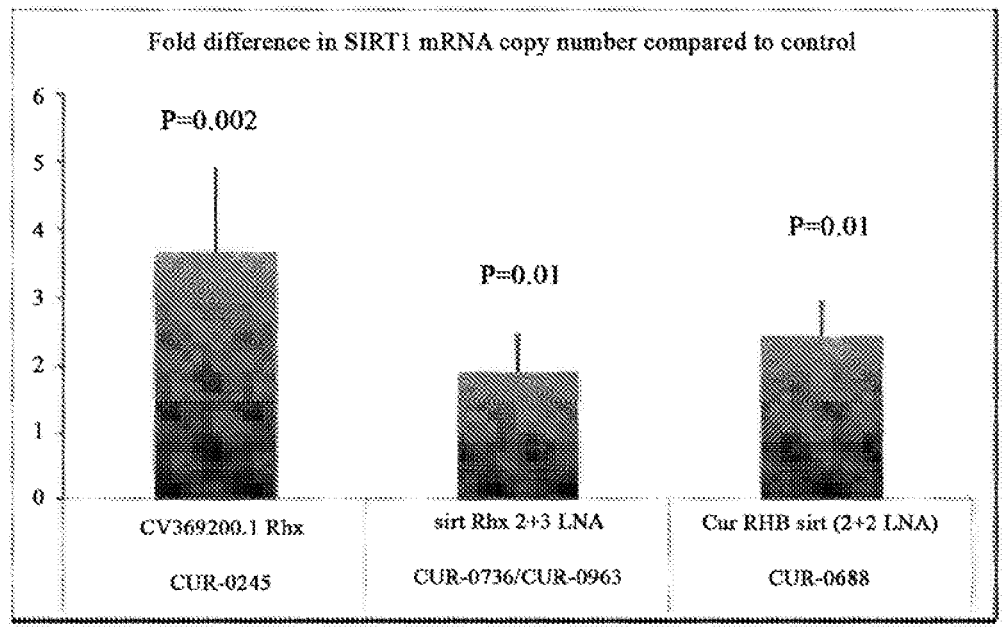

Results:

Real time PCR results show that the levels of the SIRT1 mRNA in Vero cells significantly increased 48 h after treatment with antisense oligonucleotides to SIRT1 antisense CV396200 (FIG. 5).

Treatment of DBS Cells with Antisense Oligonucleotides

DBS cells from ATCC (cat #CCL-161) were grown in growth media (MEM/EBSS (Hyclone cat #SH30024, or Mediatech cat #MT-10-010-CV)+10% FBS (Mediatech cat #MT35-011-CV)+penicillin/streptomycin (Mediatech cat #MT30-002-CI)) at 37° C. and 5% $CO_2$. One day before the experiment the cells were replated at the density of $1.5 \times 10^5$/ml into 6 well plates and incubated at 37° C. and 5% $CO_2$. On the day of the experiment the media in the 6 well plates was changed to fresh growth media. All antisense oligonucleotides were diluted to the concentration of 20 µM. Two µl of this solution was incubated with 400 µl of Opti-MEM media (Gibco cat #31985-070) and 4 µl of Lipofectamine 2000 (Invitrogen cat #11668019) at room temperature for 20 min and applied to each well of the 6 well plates with 3T3 cells. A Similar mixture including 2 µl of water instead of the oligonucleotide solution was used for the mock-transfected controls. After 3-18 h of incubation at 37° C. and 5% $CO_2$ the media was changed to fresh growth media. 48 h after addition of antisense oligonucleotides the media was removed and RNA was extracted from the cells using SV Total RNA Isolation System from Promega (cat #Z3105) or RNeasy Total RNA Isolation kit from Qiagen (cat #74181) following the manufacturers' instructions. 600 ng of RNA was added to the reverse transcription reaction performed using Verso cDNA kit from Thermo Scientific (cat #AB1453B) or High Capacity cDNA Reverse Transcription Kit (cat #4368813) as described in the manufacturer's protocol. The cDNA from this reverse transcription reaction was used to monitor gene expression by real time PCR using ABI Taqman Gene Expression Mix (cat #4369510) and primers/probes designed by ABI (Applied Biosystems Taqman Gene Expression Assay: Hs00213036 ml by Applied Biosystems Inc., Foster City Calif.). The following PCR cycle was used: 50° C. for 2 min, 95° C. for 10 min, 40 cycles of (95° C. for 15 seconds, 60° C. for 1 min) using StepOne Plus Real Time PCR Machine (Applied Biosystems).

Fold change in gene expression after treatment with antisense oligonucleotides was calculated based on the difference in 18S-normalized dCt values between treated and mock-transfected samples.

Figure 20:
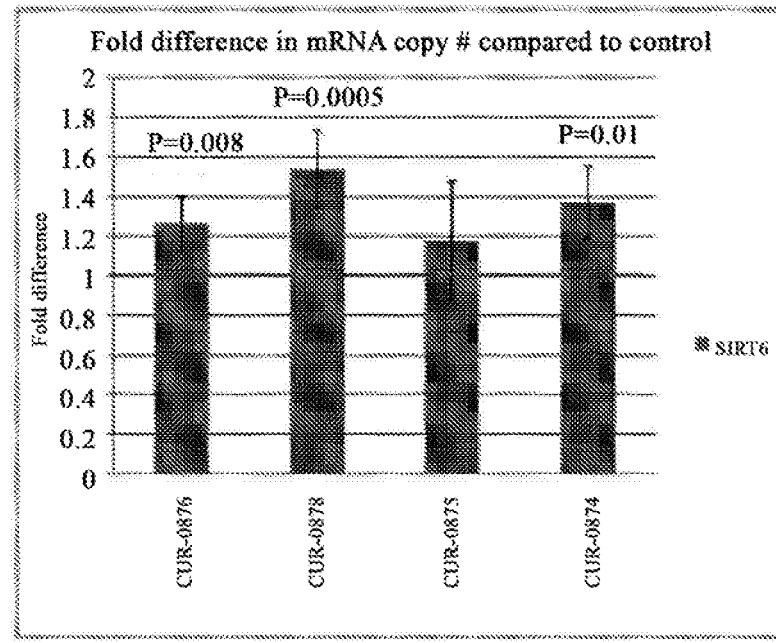
FIG. 20 is a graph of real time PCR results showing the fold change+standard deviation in SIRT6 mRNA after treatment of DBS-FCL-1 cells with phosphorothioate oligonucleotides introduced using Lipofectamine 2000, as compared to control. Real time PCR results show that the levels of SIRT6 mRNA in DBS-FCL-1 cells are significantly increased 48 h after treatment with two of the oligos designed to SIRT6 antisense bf772662 and one oligo designed to NM_133475. Bars denoted as CUR-0876, CUR-0878, CUR-0875 and CUR-0874, correspond to samples treated with SEQ ID NOS: 92, 91, 94 and 89 respectively.

Results:

Real time PCR results show that the levels of SIRT6 mRNA in DBS cells are significantly increased 48 h after treatment with two of the oligos designed to SIRT6 antisense bf772662 and one oligo designed to NM_133475 (FIG. 20).

Example 3: Modulation of SIRT Gene Expression

Materials and Methods

Treatment of HepG2 Cells with Naked Antisense Oligonucleotides:

HepG2 cells from ATCC (cat #HB-8065) were grown in growth media (MEM/EBSS (Hyclone cat #SH30024, or Mediatech cat #MT-10-010-CV)+10% FBS (Mediatech cat #MT35-011-CV)+penicillin/streptomycin (Mediatech cat #MT30-002-C1)) at 37° C. and 5% $CO_2$. One day before the experiment the cells were replated at the density of $0.5 \times 10^5$/ml into 6 well plates and incubated at 37° C. and 5% CO2. On the day of the experiment the media in the 6 well plates was replaced with 1.5 ml/well of fresh growth media. All antisense oligonucleotides were diluted in water to the concentration of 20 μM. 2 μl of this solution was incubated with 400 μl of Opti-MEM media (Gibco cat #31985-070) and 4 ul of Lipofectamine 2000 (Invitrogen cat #11668019) at room temperature for 20 min and applied to each well of the 6 well plates with HepG2 cells. Similar mixture including 2 μl of water instead of the oligonucleotide solution was used for the mock-transfected controls. After 3-18 h of incubation at 37° C. and 5% C02 the media was changed to fresh growth media. 72 h after addition of antisense oligonucleotides the cells were redosed as described in above. 48 h after the second dosing of antisense oligonucleotides the media was removed and RNA was extracted from the cells using SV Total RNA isolation System from Promega (cat #Z3105) or RNeasy Total RNA Isolation kit from Qiagen (cat #74181) following the manufacturers' instructions. 600 ng of RNA was added to the reverse transcription reaction performed using Verso cDNA kit from Thermo Scientific (cat #AB1453B) as described in the manufacturer's protocol. The cDNA from this reverse transcription reaction was used to monitor gene expression by real time PCR using ABI Taqman Gene Expression Mix (cat #4369510) and primers/probes designed by AB (Applied Biosystems Taqman Gene Expression Assay: Hs00202021_m1, Hs00202030_m1 and Hs00213036 ml by Applied Biosystems Inc., Foster City Calif.). The following PCR cycle was used: 50° C. for 2 min, 95° C. for 10 min, 40 cycles of (95° C. for 15 seconds, 60° C. for 1 min) using StepOne Plus Real Time PCR Machine (Applied Biosystems). Fold change in gene expression after treatment with antisense oligonucleotides was calculated based on the difference in 18S-normalized dCt values between treated and mock-transfected samples.

Primers and probe for the custom designed Taqman assay for exon 4:

```
the SIRT1 natural antisense CV396200
                            (SEQ ID NO: 95)
AACTGGAGCTGGGGTGTCTGTTTCA.

Forward Hiner Seq.
                            (SEQ ID NO: 96)
CCATCAGACGACATCCCTTAACAAA Reverse Primer Seq.
                            (SEQ ID NO: 97)
ACATTATATCATAGCTCCTAAAGGAGATGCA Reporter Seq.
                            (SEQ ID NO: 98)
CAGAGTTTCAATTCCC
```

Figure 2:
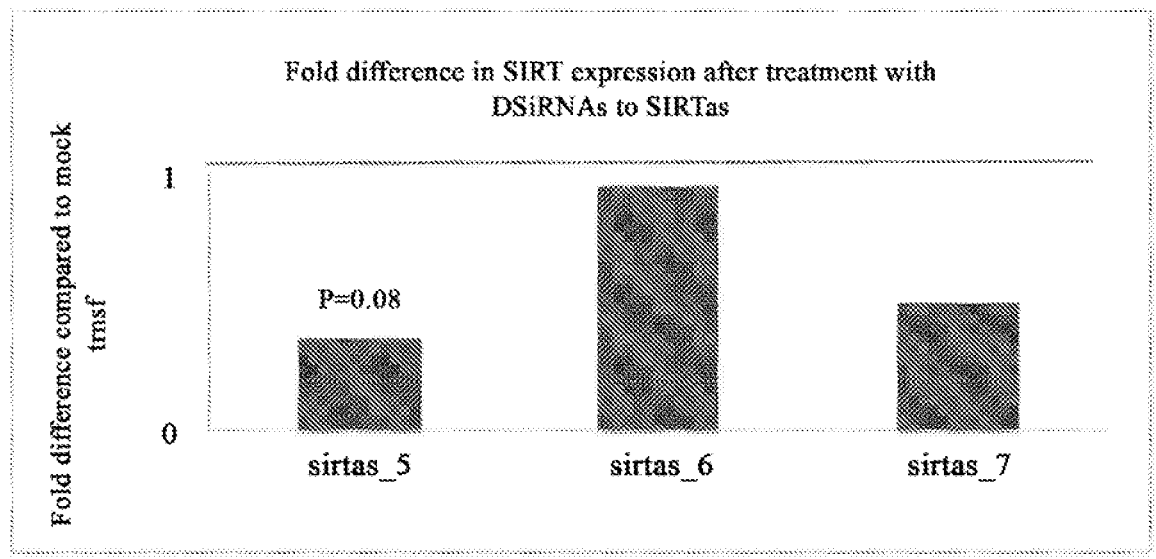

Results:

The results show that the levels of the SIRT1 mRNA in HepG2 cells are significantly increased 48 h after treatment with one of the siRNAs designed to sirtas (sirtas 5, P=0.01). In the same samples the levels of sirtas RNA were significantly decreased after treatment with sirtas 5, but unchanged after treatment with sirtas_6 and sirtas_7, which also had no effect on the SIRT1 mRNA levels (FIG. 2). sirtas_5, sirtas_6 and sirtas_7 correspond to SEQ ID NO: 38, 39 and 40 respectively.

Treatment of Primary Monkey Hepatocytes

Primary monkey hepatocytes were introduced into culture by RxGen Inc. and plated in 6 well plates. They were treated with oligonucleotides as follows. The media in the 6 well plates was changed to fresh growth media consisting of William's Medium E (Sigma cat #W41028) supplemented with 5% FBS, 50 U/ml penicillin and 50 ug/ml streptomycin, 4 ug/ml insulin, 1 uM dexamethasone, 10 ug/ml Fungin (InVivogen, San Diego Calif.). All antisense oligonucleotides were diluted to the concentration of 20 μM. 2 μl of this solution was incubated with 400 μl of Opti-MEM media (Gibco cat #31985-070) and 4 μl of Lipofectamine 2000 (Invitrogen cat #11668019) at room t temperature for 20 min and applied to each well of the 6 well plates with cells. Similar mixture including 2 μl of water instead of the oligonucleotide solution was used for the mock-transfected controls. After 3-18 h of incubation at 37° C. and 5% CO2 the media was changed to fresh growth media. 48 h after addition of antisense oligonucleotides the media was removed and RNA was extracted from the cells using SV Total RNA Isolation System from Promega (cat #Z3105) or RNeasy Total RNA Isolation kit from Qiagen (cat #74181) following the manufacturers' instructions. 600) ng of RNA was added to the reverse transcription reaction performed using Verso cDNA kit from Thermo Scientific (cat #AB1453B) as described in the manufacturer's protocol. The cDNA from this reverse transcription reaction was used to monitor gene expression by real time PCR using ABI Taqman Gene Expression Mix (cat #4369510) and primers/probes designed by ABI (Applied Biosystems Taqman Gene Expression Assay: Hs0020021_m1, Hs00202030_m1 and Hs00213036_m1 by Applied Biosystems Inc., Foster City Calif.). The following PCR cycle was used: 50° C. for 2 min, 95° C. for 10 min, 40 cycles of (95° C. for 15 seconds, 60° C. for 1 min) using Mx4000 thermal cycler (Stratagene). Fold change in gene expression after treatment with antisense oligonucleotides was calculated based on the difference in 18S-normalized dCt values between treated and mock-transfected samples.

Figure 7:
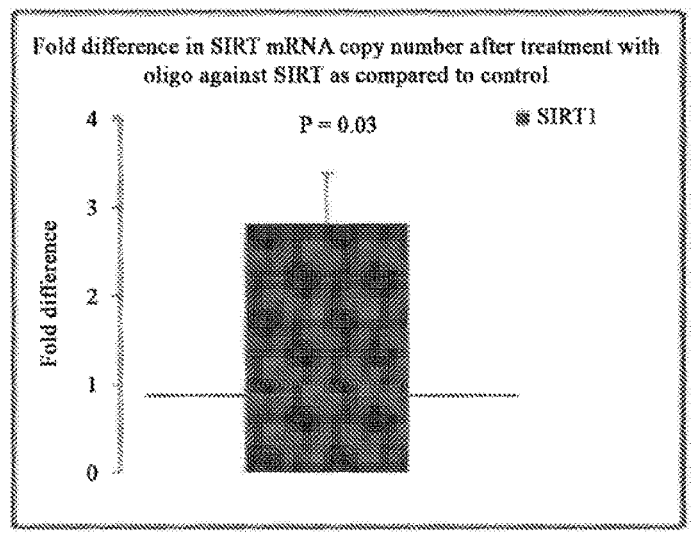
FIG. 7 shows PCR results of primary monkey liver hepatocytes. Real time PCR results show an increase in SIRT1 mRNA levels after treatment with an oligonucleotide against SIRT1 antisense. Bar denoted as CUR-0245 corresponds to SEQ ID NO: 33.

Results:

The results are shown in FIG. 7. Real time PCR results show an increase in SIRT1 mRNA levels after treatment with an oligonucleotide against SIRT1 antisense.

Example 4: Efficacy and Duration of Action Study of CUR 963 in the African Green Monkey The objective of this study was to assess and compare the effect of antisense knockdown of the discordant noncoding antisense sequences that regulate the SIRT1 genes following intravenous administration in a nonhuman primate model. The antisense oligonucleotide test articles designed to inhibit the SIRT1 regulatory sequences were designated as CUR 963.

```
CUR 963:
                            (SEQ ID NO: 34)
+G*+T*C*T*G*A*T*G*G*+A*+G*+A.

CUR 962 (control):
                            (SEQ ID NO: 99)
+G*+C*T*A*G*T*C*T*G*+T*+T*+G.
```

Regulatory Test Guidelines

This study was designed in accordance with accepted toxicological principles and to comply with International Conference of Harmonization (ICH) Harmonized Tripartite Guidelines (Non-Clinical Safety Studies for the Conduct of Human Clinical Trials for Pharmaceuticals ICH M3(m), 2000 Nov. 9), and generally accepted procedures for the testing of therapeutic agents.

Test and Control Articles

Test Article Identity and Preparation

The test article, CUR-963, is a chemically stabilized antisense oligonucleotide. The vehicle for intravenous delivery is phosphate-buffered saline (PBS).

Vehicle Characterization

For the PBS vehicle, the composition, batch number, expiry date and storage conditions (temperature and light/dark) was obtained from the supplier.

Test Article Storage and Handling

The test substance and vehicle were stored according to the received storage conditions supplied by the Sponsor and manufacturer, accordingly.

Analysis of the Test Article Formulations

Samples of the test article formulation will be cryopreserved for analysis of the concentration, stability and homogeneity of the test substance formulations.

Test System Rationale

The primate is a suitable non rodent species, acceptable to regulatory authorities as an indicator of potential hazards, and for which extensive background data are available. The African green monkey specifically is a highly clinically relevant model of multiple human physiologic and disease states.

The intravenous route of administration corresponds to a possible human therapeutic route. The dose of the test articles was based on the results of the dose finding studies of analogous compounds previously performed in the African green monkey.

African green monkeys were chosen as the primate of choice as the test substances' target sequences are conserved across species with 100% homology in primates. Additionally, the test substance is a synthetic oligonucleotide. Consequently, dosing in primates allows for a superior assessment of the efficacy of these compounds that would be more reflective of the uptake likely to be seen in humans than in any other species.

Animals

Species: *Chlorocebus sabaeus*, non-human primate
Breed: African green monkey indigenous to St. Kitts.
Source: RxGen, Lower Bourryeau, St. Kitts, West Indies.
Expected Age: The test animals were adults.
Expected Body Weight: The monkeys weigh approximately 3-4 kg. The actual range may vary but will be documented in the data.
Sex: The test animals were adult females.
Number of Animals: Ten animals were screened to ensure identification of 8 animals appropriate for enrollment in the study.
Number on Study: Females: 8
Justification for Number on Study: This study was designed to use the fewest number of animals possible, consistent with the primary objective of evaluating the therapeutic efficacy of the test article in the African green monkey and prior studies of the systemic administration of this type of oligonucleotide in this species.
Animal Specification: Ten adult African Green monkeys in the weight range of 3 to 4 kg, were employed in the study. The monkeys were drug-naïve adult animals humanely trapped from the feral population that inhabits the island. Trapped monkeys were treated with antihelminthics to eliminate any possible intestinal parasite burden and were observed in quarantine for a minimum of 4 weeks prior to screening for study enrollment. The age of trapped monkeys were estimated by size and dentation, with the exclusion of older animals from the study. Prior to study enrollment, a clinical exam was performed on each monkey, including evaluation of locomotion and dexterity. Blood samples were taken and sent to Antech Diagnostics (Memphis, Tenn.) for comprehensive clinical chemistries and a complete blood count and lipid profiles (see sections 9.2 and 319567928 for specifications). Monkeys with abnormal lab values, as determined by comparison to the established normal range for monkeys in the St. Kitts colony, were excluded from the study. In order to identify 8 monkeys that satisfy this criterion, 10 monkeys were screened, with the screening of additional animals as needed. Before study initiation, the selected monkeys will be transferred to individual cages to acclimate to individual housing for a one-week period. Only animals deemed suitable for experimentation will be enrolled in the study. The actual (or estimated) age and weight ranges at the start of the study will be detailed in the raw data and final report.

Animal Health and Welfare: The highest standards of animal welfare were followed and adhered to guidelines stipulated by the St. Kitts Department of Agriculture and the U.S. Department of Health and Human Services. All studies will be conducted in accordance with these requirements and all applicable codes of practice for the care and housing of laboratory animals. All applicable standards for veterinary care, operation, and review as contained in the NIH Guide for the Care and Use of Animals. The St. Kitts facility maintains an animal research committee that reviews the protocols and inspects the facilities as required by the Guide. The Foundation has an approved assurance filed with the Office of Laboratory Animal Welfare, as required by the Guide, #A438401 (Axion Research Foundation/St. Kitts Biomedical Foundation). There are no special nonhuman primate veterinary care issues and biohazard issues raised by the research specified in this study.

Housing and Environment: To allow detection of any treatment-related clinical signs, the animals were housed individually prior to surgery and postoperatively until sacrifice. The primate building in which the individual cages were situated were illuminated entirely by ambient light, which at 17 degrees north latitude approximates a 12 hr:12 hr light-dark cycle as recommended in the U.S. D.H.H.S guidelines. The RxGen primate building was completely ventilated to the outside. Additional air movement was assured by ceiling fans to maintain a constant target temperature of 23-35° C., as is typical of St. Kitts throughout the year. Twenty-four hour extremes of temperature and relative humidity (which also will not be controlled) were measured daily. During the study, the cages were cleaned at regular intervals.

Diet and Water: Each animal was offered approximately 90 grams per day of a standard monkey chow diet (TekLad, Madison, Wis.). The specific nutritional composition of the diet was recorded. The water was periodically analyzed for microbiological purity. The criteria for acceptable levels of contaminants in stock diet and water supply were within the analytical specifications established by the diet manufacturer and the periodic facility water evaluations, respectively. The water met all criteria necessary for certification as acceptable for human consumption.

Experimental Design

Animal Identification and Randomization:

Allocation was done by means of a stratified randomization procedure based on bodyweight and plasma cholesterol profiles. Prior to and after allocation to a group, each animal was identified by a tattoo on the abdomen. Tattoos are placed on all colony animals as a means of identification in the course of routine health inspections. A cage plan was drawn up to identify the individuals housed within, and individual monkeys were further identified by a labeled tag attached to their respective cage.

Group Sizes, Doses and Identification Members:

The animals were assigned to 2 treatment groups, comprised of 4 monkeys in each group. Specific animal identification numbers were provided to each monkey according to the facility numbering system. This system uniquely identifies each monkey by a letter followed by a three digit number, e.g. Y032.

Route and Frequency of Administration:

Animals were dosed once daily on Days 1, 3, and 5 delivered intravenously by manual infusion over ~10 min. The infusion rate will be 24 mL/kg/h. The animals were sedated with ketamine and xylazine prior to and during the dosing procedure. A venous catheter (Terumo mini vein infusion set, 20 gauge needle, or similar appropriate infusion set) was inserted into the saphenous vein. Dosing took place in each monkey between 8:00 and 10:00 a.m. shortly after the animals wake and prior to feeding. A blood sample to assess plasma cholesterol and other lipid levels as described in Blood Chemistry section below, was collected just prior to each infusion. Blood collection preceded feeding at both sampling intervals to minimize dietary effects on cholesterol measurements.

Clinical Observations:

All visible signs of reaction to treatment were recorded on each day of dosing. In addition, the animals were examined at least once each week for physical attributes such as appearance and general condition.

Body Weights:

Body weights were recorded at weekly intervals during the treatment and post-treatment periods.

Food Consumption:

Individual food consumption was not quantified. Feeding patterns were however monitored and a note made of any major changes.

Mortality and Morbidity:

Mortality and morbidity will be recorded. Any decision regarding premature sacrifice will be made after consultation with the Study Director and with the Sponsor's Monitoring Scientist, if possible. Animals that are found dead or killed prematurely will be subjected to necropsy with collection of liver, kidney, heart and spleen lung tissues for histopathology. In the event of premature sacrifice a blood sample will also be taken (if possible) and the parameters determined. Animals that are found dead after regular working hours will be refrigerated overnight and necropsies performed at the start of the next working day. If the condition of an animal requires premature sacrifice, it will be euthanized by intravenous overdose of sodium pentobarbital. All research is governed by the Principles for Use of Animals. RxGen is required by law to comply with the U.S. Department of Health and Human Services standards for primate facility, which dictates the levels of severity that the procedures within this study, specified as mild, must abide.

Clinical Laboratory Studies

Fat Biopsies:

A subcutaneous fat biopsy was performed on all study monkeys except Y775 on study days 26 by tissue extraction through a 1 cm midline incision inferior to the umbilicus. Biopsies were immediately immersed in a labeled cryotube containing 2 mls of RNAlater (Qiagen) and incubated at 4° C. overnight, after which the RNAlater was aspirated and the sample tube flash frozen in liquid nitrogen. Following transportation in liquid nitrogen total RNA was isolated for real-time qPCR of target genes.

Figure 6:
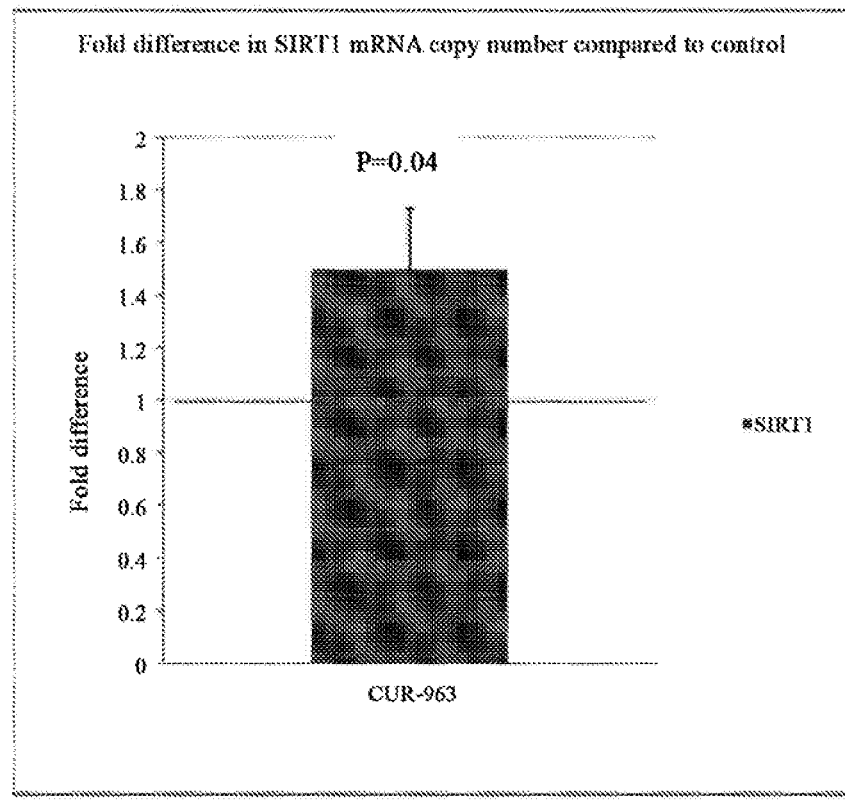
FIG. 6 shows PCR results of Monkey Fat Biopsies. Real time PCR results show an increase in SIRT1 mRNA levels in fat biopsies from monkeys dosed with CUR-963, an oligonucleotide designed to SIRT1 antisense CV396200.1. CUR-963 corresponds to SEQ ID NO: 34.

Results:

Real time PCR results show an increase in SIRT1 mRNA levels in fat biopsies from monkeys dosed with CUR-963, an oligonucleotide designed to SIRT1 antisense CV396200.1, compared to monkeys dosed with CUR-962 (SEQ ID NO.: 99), an oligonucleotide which had no effect on SIRT1 expression in vitro (designed to ApoA1 antisense DA327409, data not shown). mRNA levels were determined by real time PCR (FIG. 6).

Example 5: In Vivo Modulation of Sirtuin (SIRT) by Antisense DNA Oligonucleotides Treatment with Antisense DNA Oligonucleotides (ASO):

Antisense oligonucleotides (ASO) specific for SIRT1 AS are administered to C57B/6J mice which are fed a high fat diet for 12 weeks to induce obesity and diabetes. (Purushotham A. et al., (2009) *Cell Metabolism* 9, p. 327-338). The treatment of the mice with ASO will start at the time of the implementation of the high fat diet. Mice are injected IP once a week with ASO prepared in normal saline, at a concentration of 5 mg/kg.

Measurements of Body Weight and Food Intake:

Body weight and food intake of mice are measured twice per week, prior to IP injection of the ASO.

Blood Glucose Measurements:

Fed and fasted blood glucose concentrations are measured each week by taking a sample of blood from the tail vein.

Glucose Tolerance Tests (GTT):

The GTT will be done totally twice per mouse, halfway through the diet (at week 4) and near the end (at week 10) of the high fat diet. The GTT will inform us about the glucose tolerance of the mice that is the capacity to rapidly clear a glucose bolus from the blood stream. This is a measure for diabetes. Mice are fasted overnight for 16 hours. Mice are injected IP glucose 2 g/kg. This translates into a final volume of 0.2 ml 30% (w/v) glucose solution for a mouse of 30 g weight Glucose measurements are taken prior to glucose injection and at 5, 15, 30, 60, 90 and 120 min post-injection. Glucose is measured by cutting the tail tip 1 mm from the end of the tail under isoflurane anesthesia prior to IP glucose injection. The blood droplet is aspirated into a strip and glucose concentration is measured with a glucometer. The GTT will be done totally twice per mouse, halfway through the diet (at week 4) and near the end (at week 10) of the high fat diet. The GTT will inform us about the glucose tolerance of the mice that is the capacity to rapidly clear a glucose bolus from the blood stream. This is a measure for diabetes.

Insulin Tolerance Test (ITT):

Mice are fasted for 6 hours from 9 am till 3 pm. Mice are then injected IP 0.5-1 U Insulin/kg. The insulin concentration will be adjusted such that the final injected volume is 0.1-0.15 ml. Blood glucose measurements are taken prior to injection and at 5, 15, 30, 45, and 60 minutes post-injection. Blood is collected exactly as described under GTT. In addition to monitoring the glucose levels, the behavior of the mice is constantly observed during the ITT. Hypoglycemia can manifest as a change in behavior with the animals becoming very quiet and showing discomfort. To prevent hypoglycemia, glucose (1 g/kg) is injected IP in a final volume of 0.1-0.15 m as soon as the blood glucose concentration falls below 50 mg/ml or signs of discomfort are observed.

Blood Collection by Facial Vein Puncture:

Mice are restrained by the scruff of the neck and base of the tail, slightly compressing the blood vessels of the neck through the tautness of the grip on the neck skin. The sampling site is on the jaw slightly in front of the angle of the mandible. The skin at the sampling site is punctured with an 18 G needle or a lancet at a 90 angle until the tip of the needle/lancet just passes through the skin. Blood samples are collected using microhematocrit tubes. After blood has been collected, the grip on the neck is loosened and pressure is applied at the insertion site with a gauze sponge to ensure hemostasis. 0.05-0.2 ml of blood will be collected by this method. This procedure will be performed only once in week 5 of the high fat diet and eventually in week 12 if the intracardiac puncture is not working (see below). Blood hormones which regulate the metabolism of glucose and lipids (such as insulin, adiponectin and leptin) are measured using commercially available ELISA kits. (e.g., R&D Systems, Minneapolis, Minn., Assay Pro St. Charles, Mo., Mabtech, Mariemont, Ohio)

Intracardiac Puncture:

At the end of the 12 week high fat diet, mice will be anesthetized by continuous isoflurane inhalation. Anesthesia is induced by placing the mice in an induction box, which is supplied with isoflurane and oxygen. Mice will be restrained on their back. The heart is punctured with a 27 G needle. Following exsanguineation, the head is decapitated to ensure death. Tissues (liver, pancreas, white and brown adipose tissue, and skeletal muscle) are collected for further investigations (RNA and protein measurements and histology).

Around 0.5-1 ml of blood will be obtained and used to determine several critical parameters of glucose and lipid metabolism (glucose, insulin, cholesterol, triglycerides, free fatty acids, leptin, adipokines, corticosteroids, thyroid hormones). If difficulties occur in this method, we will collect blood by facial vein puncture under isoflurane anesthesia instead (see above).

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The Abstract of the disclosure will allow the reader to quickly ascertain the nature of the technical disclosure. It is submitted with the understanding that it will not be used to interpret or limit the scope or meaning of the following claims.

What is claimed is:

1. A synthetic, modified single stranded oligonucleotide of 12 to 24 nucleotides in length comprising at least one modification wherein the at least one modification is selected from: at least one modified sugar moiety; at least one modified internucleotide linkage; at least one modified nucleotide, and combinations thereof; wherein said oligonucleotide is an antisense compound which hybridizes to and is 100% complementary to a complementary polynucleotide comprising 12 to 24 nucleotides within nucleotides 1 to 1028 of SEQ ID NO: 5 or nucleotides 1 to 352 and 373 to 429 of SEQ ID NO: 6, or nucleotides 1 to 156 of SEQ ID NO: 7 or nucleotides 255 to 274 of SEQ ID NO: 8, or 1 to 373 of SEQ ID NO: 9, or 1 to 589 of SEQ ID NO: 12 or 1 to 4026 of SEQ ID NO: 14, thereby upregulating a function and/or expression of a Sirtuin (SIRT) polynucleotide having SEQ ID NOS: 1, 3 or 4 in vivo or in vitro as compared to a normal control and further wherein the oligonucleotides upregulating a polynucleotide having SEQ ID NO: 1 are selected from the group consisting of SEQ ID NOS: 15, 30, 31, 33, 34, 35, 36, 37, 41, 42, 45, 50, 53, 56, 58 and 60.

2. The oligonucleotide of claim 1, wherein the at least one modification comprises an internucleotide linkage selected from the group consisting of phosphorothioate, alkylphosphonate, phosphorodithioate, alkylphosphonothioate, phosphoramidate, carbamate, carbonate, phosphate triester, acetamidate, carboxymethyl ester, and combinations thereof.

3. The oligonucleotide of claim 1, wherein said oligonucleotide comprises at least one phosphorothioate internucleotide linkage.

4. The oligonucleotide of claim 1, wherein said oligonucleotide comprises a backbone of phosphorothioate internucleotide linkages.

5. The oligonucleotide of claim 1, wherein the oligonucleotide comprises at least one modified nucleotide, said modified nucleotide selected from: a peptide nucleic acid, a locked nucleic acid (LNA), and a combination thereof.

6. The oligonucleotide of claim 1, wherein the oligonucleotide comprises a plurality of modifications, wherein said modifications comprise modified nucleotides selected from: phosphorothioate, alkylphosphonate, phosphorodithioate, alkylphosphonothioate, phosphoramidate, carbamate, carbonate, phosphate triester, acetamidate, carboxymethyl ester, and a combination thereof.

7. The oligonucleotide of claim 1, wherein the oligonucleotide comprises a plurality of modifications, wherein said modifications comprise modified nucleotides selected from: peptide nucleic acids, locked nucleic acids (LNA), and a combination thereof.

8. The oligonucleotide of claim 1, wherein the oligonucleotide comprises at least one modified sugar moiety selected from: a 2'-O-methoxyethyl modified sugar moiety, a 2'-methoxy modified sugar moiety, a 2'-O-alkyl modified sugar moiety, a bicyclic sugar moiety, and a combination thereof.

9. The oligonucleotide of claim 1, wherein the oligonucleotide comprises a plurality of modifications, wherein said modifications comprise modified sugar moieties selected from: a 2'-O-methoxyethyl modified sugar moiety, a 2'-methoxy modified sugar moiety, a 2'-O-alkyl modified sugar moiety, a bicyclic sugar moiety, and a combination thereof.

10. A pharmaceutical composition comprising one or more oligonucleotides according to claim 1 and a pharmaceutically acceptable excipient.

11. The pharmaceutical composition of claim 10, wherein the oligonucleotides have at least about 95% sequence identity as compared to any one of the nucleotide sequences set forth as SEQ ID NOS 33, 34, 35, 36 or 37.

12. A single stranded, modified oligonucleotide having about 10 to 24 nucleotides in length having 100% complementarity to a natural antisense strand of a Sirtuin (SIRT) polynucleotide selected from nucleotides 1 to 411 and 423 to 436 and 485 to 1028 of SEQ ID NO: 5 or nucleotides 1 to 429 of SEQ ID NO: 6 or nucleotides 1-156 of SEQ ID NO: 7 or nucleotides 1 to 593 of SEQ ID NO: 8 or 1 to 373 of SEQ ID NO: 9 or 1 to 159 of SEQ ID NO: 12 or 1 to 428 of SEQ ID NO: 13 or 1 to 4041 of SEQ ID NO: 14 and wherein said at least one antisense oligonucleotide has sequence identity to at least one nucleic acid sequence of 10 to 24 nucleotides in length set forth within SEQ ID NOS: 1, 3 or 4 and wherein said antisense oligonucleotides upregulate the expression of SEQ ID NOS: 1, 3 or 4 in mammalian cells or tissues in vivo or in vitro and wherein oligonucleotides upregulating SEQ ID NO: 4 are selected from the group consisting of SEQ ID NOS: 89-90 and 92-94.

13. A single stranded, modified oligonucleotide of 14 to 24 nucleotides in length wherein said oligonucleotide is 100% complementary to and hybridizes to a polynucleotide comprising 12 to 24 nucleotides within nucleotides 296 to 660 of SEQ ID NO: 11, thereby upregulating a function and/or expression of a Sirtuin (SIRT) polynucleotide having SEQ ID NO 3 in patient cells or tissues in vivo or in vitro.

14. A siRNA oligonucleotide of 20 to 27 nucleotides in length having 100% complementarity with a target region of a natural antisense polynucleotide of a Sirtuin (SIRT) polynucleotide selected from nucleotides 1 to 35 and 55 to 660 of SEQ ID NO: 11 and upregulating the expression or function of a Sirtuin (SIRT) polynucleotide having SEQ ID NO:3 in mammalian cells or tissues in vivo or in vitro.

15. A single-stranded, modified oligonucleotide of 14 to 24 nucleotides in length or at least one siRNA oligonucleotide of 20-27 nucleotides in length having 100% complementarity with and which targets and hybridizes to a complementary target region of a natural antisense polynucleotide of the Sirtuin (SIRT) polynucleotide thereby upregulating a function and/or expression of a SIRT polynucleotide having SEQ ID NO: 3 and wherein the target region is selected from nucleotides 296 to 660 of SEQ ID NO: 11.

16. A pharmaceutical composition comprising a single stranded modified oligonucleotide according to claim 12, 13 or 15 and a pharmaceutically acceptable excipient.

17. A pharmaceutical composition comprising a siRNA according to claim 14 or 15 and a pharmaceutically acceptable excipient.

18. A single-stranded, modified oligonucleotide of 14 to 24 nucleotides in length selected from the group consisting of SEQ ID NOS: 79, 80, 82, 83 and 84 and having CUR NOS: CUR-1545, CUR-1546, CUR-1549, CUR-1550 and CUR-1547.

* * * * *

SEQUENCE LISTING

```
<160> NUMBER OF SEQ ID NOS: 103

<210> SEQ ID NO 1
<211> LENGTH: 4107
<212> TYPE: DNA
<213> ORGANISM: Homo sapiens
<300> PUBLICATION INFORMATION:
<308> DATABASE ACCESSION NUMBER: NM_012238.3
<309> DATABASE ENTRY DATE: 2008-11-30
<313> RELEVANT RESIDUES IN SEQ ID NO: (1)..(4107)

<400> SEQUENCE: 1
gtcgagcggg agcagaggag gcgagggagg agggccagag aggcagttgg aagatggcgg      60
acgaggcggc cctcgccctt cagcccggcg gctcccccctc ggcggcgggg gccgacaggg     120
aggccgcgtc gtcccccgcc ggggagccgc tccgcaagag gccgcggaga gatggtcccg     180
gcctcgagcg gagcccgggc gagcccggtg gggcggcccc agagcgtgag gtgccggcgg     240
cggccagggg ctgcccgggt gcggcggcgg cggcgctgtg gcgggaggcg gaggcagagg     300
cggcggcggc aggcggggag caagaggccc aggcgactgc ggcggctggg gaaggagaca     360
atgggccggg cctgcagggc ccatctcggg agccaccgct ggccgacaac ttgtacgacg     420
aagacgacga cgacgagggc gaggaggagg aagaggcggc ggcggcggcg attgggtacc     480
gagataacct tctgttcggt gatgaaatta tcactaatgg ttttcattcc tgtgaaagtg     540
atgaggagga tagagcctca catgcaagct ctagtgactg gactccaagg ccacggatag     600
gtccatatac ttttgttcag caacatctta tgattggcac agatcctcga acaattctta     660
aagatttatt gccggaaaca atacctccac ctgagttgga tgatatgaca ctgtggcaga     720
ttgttattaa tatcctttca gaaccaccaa aaaggaaaaa aagaaaagat attaatacaa     780
ttgaagatgc tgtgaaatta ctgcaagagt gcaaaaaaat tatagttcta actggagctg     840
gggtgtctgt ttcatgtgga atacctgact tcaggtcaag ggatggtatt tatgctcgcc     900
ttgctgtaga cttcccagat cttccagatc ctcaagcgat gtttgatatt gaatatttca     960
gaaaagatcc aagaccattc ttcaagtttg caaaggaaat atatcctgga caattccagc    1020
catctctctg tcaaaattc atagccttgt cagataagga aggaaaacta cttcgcaact    1080
atacccagaa catagacacg ctggaacagg ttgcgggaat ccaaaggata attcagtgtc    1140
```

```
atggttcctt tgcaacagca tcttgcctga tttgtaaata caaagttgac tgtgaagctg    1200
tacgaggaga tatttttaat caggtagttc ctcgatgtcc taggtgccca gctgatgaac    1260
cgcttgctat catgaaacca gagattgtgt tttttggtga aaatttacca gaacagtttc    1320
atagagccat gaagtatgac aaagatgaag ttgacctcct cattgttatt gggtcttccc    1380
tcaaagtaag accagtagca ctaattccaa gttccatacc ccatgaagtg cctcagatat    1440
taattaatag agaacctttg cctcatctgc attttgatgt agagcttctt ggagactgtg    1500
atgtcataat taatgaattg tgtcataggt taggtggtga atatgccaaa ctttgctgta    1560
accctgtaaa gctttcagaa attactgaaa acctccacg aacacaaaaa gaattggctt     1620
atttgtcaga gttgccaccc acacctcttc atgtttcaga agactcaagt tcaccagaaa    1680
gaacttcacc accagattct tcagtgattg tcacactttt agaccaagca gctaagagta    1740
atgatgattt agatgtgtct gaatcaaaag gttgtatgga agaaaaacca caggaagtac    1800
aaacttctag gaatgttgaa agtattgctg aacagatgga aaatccggat ttgaagaatg    1860
ttggttctag tactggggag aaaaatgaaa gaacttcagt ggctggaaca gtgagaaaat    1920
gctggcctaa tagagtggca aaggagcaga ttagtaggcg gcttgatggt aatcagtatc    1980 tgttttttgcc accaaatcgt tacatttttcc atggcgctga ggtatattca gactctgaag   2040
atgacgtctt atcctctagt tcttgtggca gtaacagtga tagtgggaca tgccagagtc    2100
caagtttaga agaacccatg gaggatgaaa gtgaaattga agaattctac aatggcttag    2160
aagatgagcc tgatgttcca gagagagctg gaggagctgg attttgggact gatggagatg    2220 atcaagaggc aattaatgaa gctatatctg tgaaacagga agtaacagac atgaactatc    2280
catcaaacaa atcatagtgt aataattgtg caggtacagg aattgttcca ccagcattag    2340
gaactttagc atgtcaaaat gaatgtttac ttgtgaactc gatagagcaa ggaaaccaga    2400 aagtgtaat atttataggt tggtaaaata gattgttttt catggataat ttttaacttc     2460
attatttctg tacttgtaca aactcaacac taactttttt ttttttaaaa aaaaaaggt     2520 actaagtatc ttcaatcagc tgttggtcaa gactaacttt cttttaaagg ttcatttgta    2580
tgataaattc atatgtgtat ataattttt ttttgttttg tctagtgagt ttcaacattt     2640
ttaaagtttt caaaaagcca tcggaatgtt aaattaatgt aaagggacag ctaatctaga    2700
ccaaagaatg gtattttcac ttttctttgt aacattgaat ggtttgaagt actcaaaatc    2760
tgttacgcta aacttttgat tctttaacac aattattttt aaacactggc attttccaaa    2820
actgtggcag ctaacttttt aaaatctcaa atgacatgca gtgtgagtag aaggaagtca    2880
acaatatgtg gggagagcac tcggttgtct ttacttttaa aagtaatact tggtgctaag    2940
aatttcagga ttattgtatt tacgttcaaa tgaagatggc ttttgtactt cctgtggaca    3000
tgtagtaatg tctatattgg ctcataaaac taacctgaaa acaaataaa tgctttggaa     3060 atgtttcagt tgctttagaa acattagtgc ctgcctggat cccttagtt ttgaaatatt     3120 tgccattgtt gtttaaatac ctatcactgt ggtagagctt gcattgatct tttccacaag    3180
tattaaactg ccaaaatgtg aatatgcaaa gcctttctga atctataata atggtacttc    3240
tactggggag agtgtaatat tttggactgc tgttttccat taatgaggag agcaacaggc    3300
ccctgattat acagttccaa agtaataaga tgttaattgt aattcagcca gaaagtacat    3360
gtctcccatt ggaggatttt ggtgttaaat accaaactgc tagccctagt attatggaga    3420
tgaacatgat gatgtaactt gtaatagcag aatagttaat gaatgaaact agttcttata    3480
```

-continued

| | |
|---|---|
| atttatctttt atttaaaagc ttagcctgcc ttaaaactag agatcaactt tctcagctgc | 3540 |
| aaaagcttct agtcttttcaa gaagttcata ctttatgaaa ttgcacagta agcatttatt | 3600 |
| tttcagacca tttttgaaca tcactcctaa attaataaag tattcctctg ttgctttagt | 3660 |
| atttattaca ataaaaaggg tttgaaatat agctgttctt tatgcataaa acacccagct | 3720 |
| aggaccatta ctgccagaga aaaaaatcgt attgaatggc catttcccta cttataagat | 3780 |
| gtctcaatct gaatttattt ggctacacta agaatgcag tatatttagt tttccatttg | 3840 |
| catgatgttt gtgtgctata gatgatattt taaattgaaa agtttgtttt aaattatttt | 3900 |
| tacagtgaag actgttttca gctcttttta tattgtacat agtctttat gtaatttact | 3960 |
| ggcatatgtt ttgtagactg tttaatgact ggatatcttc cttcaacttt tgaaatacaa | 4020 |
| aaccagtgtt ttttacttgt acactgtttt aaagtctatt aaaattgtca tttgactttt | 4080 |
| ttctgttaaa aaaaaaaaaa aaaaaaa | 4107 |

<210> SEQ ID NO 2
<211> LENGTH: 3806
<212> TYPE: DNA
<213> ORGANISM: Mus musculus
<300> PUBLICATION INFORMATION:
<308> DATABASE ACCESSION NUMBER: NM_001159589.1
<309> DATABASE ENTRY DATE: 2010-07-18
<313> RELEVANT RESIDUES IN SEQ ID NO: (1)..(3806)

<400> SEQUENCE: 2

| | |
|---|---|
| gccagtgccg cgcgtcgagc ggagcagagg aggcgagggc ggagggccag agaggcagtt | 60 |
| ggaagatggc ggacgaggtg gcgctcgccc ttcaggccgc cggctcccct tccgcggcgg | 120 |
| ccgccatgga ggccgcgtcg cagccggcgg acgagccgct ccgcaagagg ccccgccgag | 180 |
| acgggcctgg cctcgggcgc agccggggcg agccgagcgc agcagtggcg ccggcggccg | 240 |
| cggggtgtga ggcggcgagc gccgcggccc cggcggcgct gtggcgggag gcggcagggg | 300 |
| cggcggcgag cgcggagcgg gaggccccgg cgacggccgt ggccggggac ggagacaatg | 360 |
| ggtccggcct gcggcgggag ccgagggcgg ctgacgactt cgacgacgac gagggcgagg | 420 |
| aggaggacga ggcggcggcg gcagcggcgg cggcagcgat cggctaccga ggtccatata | 480 |
| cttttgttca gcaacatctc atgattggca ccgatcctcg aacaattctt aaagatttat | 540 |
| taccagaaac aattcctcca cctgagctgg atgatatgac gctgtggcag attgttatta | 600 |
| atatcctttc agaaccacca aagcggaaaa aaagaaaaga tatcaataca attgaagatg | 660 |
| ctgtgaagtt actgcaggag tgtaaaaaga taatagttct gactggagct gggggtttctg | 720 |
| tctcctgtgg gattcctgac ttcagatcaa gagacggtat ctatgctcgc cttgcggtgg | 780 |
| acttcccaga cctcccagac cctcaagcca tgtttgatat tgagtatttt agaaaagacc | 840 |
| caagaccatt cttcaagttt gcaaaggaaa tatatcccgg acagttccag ccgtctctgt | 900 |
| gtcacaaatt catagctttg tcagataagg aaggaaaaact acttcgaaat tatactcaaa | 960 |
| atatagatac cttggagcag gttgcaggaa tccaaggat ccttcagtgt catggttcct | 1020 |
| ttgcaacagc atcttgcctg atttgtaaat acaaagttga ttgtgaagct gttcgtggag | 1080 |
| acattttaa tcaggtagtt cctcggtgcc ctaggtgccc agctgatgag ccacttgcca | 1140 |
| tcatgaagcc agagattgtc ttctttggtg aaaacttacc agaacagttt catagagcca | 1200 |
| tgaagtatga caaagatgaa gttgacctcc tcattgttat tggatcttct ctgaaagtga | 1260 |
| gaccagtagc actaattcca agttctatac cccatgaagt gcctcaaata ttaataaata | 1320 |
| gggaaccttt gcctcatcta cattttgatg tagagctcct tggagactgc gatgttataa | 1380 |

```
ttaatgagtt gtgtcatagg ctaggtggtg aatatgccaa actttgttgt aaccctgtaa    1440
agctttcaga aattactgaa aaacctccac gcccacaaaa ggaattggtt catttatcag    1500
agttgccacc aacacctctt catatttcgg aagactcaag ttcacctgaa agaactgtac    1560
cacaagactc ttctgtgatt gctacacttg tagaccaagc aacaaacaac aatgttaatg    1620
atttagaagt atctgaatca agttgtgtgg aagaaaaacc acaagaagta cagactagta    1680
ggaatgttga aacattaat gtggaaaatc cagattttaa ggctgttggt tccagtactg    1740
cagacaaaaa tgaaagaact tcagttgcag aaacagtgag aaaatgctgg cctaatagac    1800
ttgcaaagga gcagattagt aagcggcttg agggtaatca atacctgttt gtaccaccaa    1860
atcgttacat attccacggt gctgaggtat actcagactc tgaagatgac gtcttgtcct    1920
ctagttcctg tggcagtaac agtgacagtg gcacatgcca gagtccaagt ttagaagaac    1980
ccttggaaga tgaaagtgaa attgaagaat tctacaatgg cttggaagat gatacggaga    2040
ggcccgaatg tgctggagga tctggatttg gagctgatgg aggggatcaa gaggttgtta    2100
atgaagctat agctacaaga caggaattga cagatgtaaa ctatccatca gacaaatcat    2160
aacactattg aagctgtccg gattcaggaa ttgctccacc agcattggga actttagcat    2220
gtcaaaaaat gaatgtttac ttgtgaactt gaacaaggaa atctgaaaga tgtattattt    2280
atagactgga aaatagattg tcttcttgga taatttctaa agttccatca tttctgtttg    2340
tacttgtaca ttcaacactg ttggttgact tcatcttcct ttcaaggttc atttgtatga    2400
tacattcgta tgtatgtata atttgtttt ttgcctaatg agtttcaacc tttaaagtt     2460 ttcaaaagcc attggaatgt taatgtaaag ggaacagctt atctagacca agaatggta    2520 tttcacactt ttttgtttgt aacattgaat agtttaaagc cctcaatttc tgttctgctg    2580 aactttatt tttaggacag ttaactttt aaacactggc attttccaaa acttgtggca    2640
gctaactttt taaaatcaca gatgacttgt aatgtgagga gtcagcaccg tgtctggagc    2700
actcaaaact tggtgctcag tgtgtgaagc gtacttactg catcgttttt gtacttgctg    2760
cagacgtggt aatgtccaaa caggcccctg agactaatct gataaatgat ttggaaatgt    2820
gtttcagttg ttctagaaac aatagtgcct gtctatatag gtccccttag tttgaatatt    2880
tgccattgtt taattaaata cctatcactg tggtagagcc tgcatagatc ttcaccacaa    2940
atactgccaa gatgtgaata tgcaaagcct ttctgaatct aataatggta cttctactgg    3000
ggagagtgta atattttgga ctgctgtttt tccattaatg aggaaagcaa taggcctctt    3060
aattaaagtc ccaaagtcat aagataaatt gtagctcaac cagaaagtac actgttgcct    3120
gttgaggatt tggtgtaatg tatcccaagg tgttagcctt gtattatgga gatgaataca    3180 gatccaaatag tcaaatgaaa ctagttctta gttatttaaa agcttagctt gccttaaaac    3240
tagggatcaa ttttctcaac tgcagaaact tttagccttt caaacagttc acacctcaga    3300
aagtcagtat ttattttaca gacttctttg gaacattgcc cccaaattta aatattcatg    3360
tgggtttagt atttattaca aaaaaatgat ttgaaatata gctgttcttt atgcataaaa    3420
tacccagtta ggaccattac tgccagagga gaaaagtatt aagtagctca tttccctacc    3480
taaaagataa ctgaatttat ttggctacac taaagaatgc agtatattta gttttccatt    3540
tgcatgatgt gtttgtgcta tagacaatat tttaaattga aaatttgtt ttaaattatt     3600 tttacagtga agactgtttt cagctctttt tatattgtac atagactttt atgtaatctg    3660
gcatatgttt tgtagaccgt ttaatgactg gattatcttc ctccaacttt tgaaatacaa    3720
```

| | |
|---|---|
| aaacagtgtt ttatacttgt atcttgtttt aaagtcttat attaaaattg tcatttgact | 3780 |
| tttttcccgt taaaaaaaaa aaaaaa | 3806 |

<210> SEQ ID NO 3
<211> LENGTH: 2919
<212> TYPE: DNA
<213> ORGANISM: Homo sapiens
<300> PUBLICATION INFORMATION:
<308> DATABASE ACCESSION NUMBER: NM_012239
<309> DATABASE ENTRY DATE: 2010-07-04
<313> RELEVANT RESIDUES IN SEQ ID NO: (1)..(2919)

<400> SEQUENCE: 3

| | |
|---|---|
| gcgagtccgg aggactcctt ggactgcgcg gaacatggcg ttctggggtt ggcgcgccgc | 60 |
| ggcagccctc cggctgtggg gccgggtagt tgaacgggtc gaggccgggg gaggcgtggg | 120 |
| gccgttttcag gcctgcggct gtcggctggt gcttggcggc agggacgatg tgagtgcggg | 180 |
| gctgagaggc agccatgggg cccgcggtga gcccttggac ccggcgcgcc ccttgcagag | 240 |
| gcctcccaga cccgaggtgc ccagggcatt ccggaggcag ccgagggcag cagctcccag | 300 |
| tttcttcttt tcgagtatta aaggtggaag aaggtccata tcttttttctg tgggtgcttc | 360 |
| aagtgttgtt ggaagtggag gcagcagtga caaggggaag cttttccctgc aggatgtagc | 420 |
| tgagctgatt cgggccagag cctgccagag ggtggtggtc atggtggggg ccggcatcag | 480 |
| cacacccagt ggcattccag acttcagatc gccggggagt ggcctgtaca gcaacctcca | 540 |
| gcagtacgat ctcccgtacc ccgaggccat ttttgaactc ccattcttct ttcacaaccc | 600 |
| caagcccttt ttcactttgg ccaaggagct gtaccctgga aactacaagc ccaacgtcac | 660 |
| tcactacttt ctccggctgc ttcatgacaa ggggctgctt ctgcggctct acacgcagaa | 720 |
| catcgatggg cttgagagag tgtcgggcat ccctgcctca aagctggttg aagctcatgg | 780 |
| aacctttgcc tctgccacct gcacagtctg ccaaagaccc ttcccagggg aggacattcg | 840 |
| ggctgacgta tggcagacag gggttccccg ctgcccggtc tgcaccggcg ttgtgaagcc | 900 |
| cgacattgtg ttctttgggg agccgctgcc ccagaggttc ttgctgcatg tggttgattt | 960 |
| ccccatggca gatctgctgc tcatccttgg gacctccctg gaggtggagc ttttgccag | 1020 |
| cttgaccgag gccgtgcgga gctcagttcc ccgactgctc atcaaccggg acttggtggg | 1080 |
| gcccttggct tggcatcctc gcagcaggga cgtggcccag ctgggggacg tggttcacgg | 1140 |
| cgtggaaagc ctagtggagc ttctgggctg gacagaagag atgcgggacc ttgtgcagcg | 1200 |
| ggaaactggg aagcttgatg gaccagacaa ataggatgat ggctgccccc acacaataaa | 1260 |
| tggtaacata ggagacatcc acatcccaat tctgacaaga cctcatgcct gaagacagct | 1320 |
| tgggcaggtg aaaccagaat atgtgaactg agtggacacc cgaggctgcc actggaatgt | 1380 |
| cttctcaggc catgagctgc agtgactggt agggctgtgt ttacagtcag ggccaccccg | 1440 |
| tcacatatac aaaggagctg cctgcctgtt tgctgtgttg aactcttcac tctgctgaag | 1500 |
| ctcctaatgg aaaaagcttt cttctgactg tgaccctctt gaactgaatc agaccaactg | 1560 |
| gaatcccaga ccgagtctgc tttctgtgcc tagttgaacg gcaagctcgg catctgttgg | 1620 |
| ttacaagatc cagacttggg ccgagcggtc cccagccctc ttcatgttcc gaagtgtagt | 1680 |
| cttgaggccc tggtgccgca cttctagcat gttggtctcc tttagtgggg ctattttttaa | 1740 |
| tgagagaaaa tctgttcttt ccagcatgaa atacatttag tctcctcaaa gggactgcag | 1800 |
| gtgttgacat gagttggaaa gggaaccctg ggatacgtgg cgtcccctct attgaacag | 1860 |
| tctgaggact gaaggcattt gtccctggat ttattggaga cggcccagct cctccctctg | 1920 |

```
aaggtggtca cattctgttg actctccata ctcagcctct cctccagaaa cagatctgtt    1980
ccagaacatt ccagcacttt ctatctggcc tccttgtccc cacactacgc cccccaccc    2040 tcgccagggc ttcctctagt gacactgtta gagctaatct ctgagacagg gaaggcatta   2100
ctcacttaaa acccaggctg agtcctggcc acctgctgga ttgtgacata ggaggtggaa   2160
tccactgaac tgctacttct gcacaggctc cttctcctgg ggctgtaccc aggcccagcc   2220
ctgatggctc accctgtcag gcaccagctg ctccctcctg ggctctcacc cacctgcaca   2280
tcctccttcc tagcatcaca ttacctgcgt gtttccccag acaaaagcac ttcccattct   2340
tgaaccttgc ctaccctggg ctgagctgac ggcaatagat ttaatgacag tgactcccag   2400 gaaggggtc ctgtgacttt gcgccttaat aagaacaaaa ggtggaattg gtgacctagg    2460
aaaactgttg aattctaaaa agaatgaagt tagtttctaa ccctagttaa tgttcctttt   2520
ttattttttg agtcttgccc tgtcactcag ggtggagtgc ggtgttatga tctcagctca   2580
ctgcaacttc cgcctcccgg gtttaagcga ttctcctggg tagctgggat tacaggtgtg   2640
tcccaccaca cctagcacat gggcatattt gtaatagaga caaggttttg ctatgttggc   2700
caggctggtc tcgaactcct ggcttcaagt gatccaccca cctcggcctc ccaaagtgct   2760
gggattacag gcatgagcca ctgtgcctgg cccctttatt tgataattta cacatacatt   2820
tttgtccaaa actcttcttt atttcaagat gatgtttctg tggctatgtg tggtatgtgg   2880
tataaatctc aatctatggt caaaaaaaaa aaaaaaaa                            2919

<210> SEQ ID NO 4
<211> LENGTH: 1657
<212> TYPE: DNA
<213> ORGANISM: Homo sapiens
<300> PUBLICATION INFORMATION:
<308> DATABASE ACCESSION NUMBER: NM_016539
<309> DATABASE ENTRY DATE: 2010-07-17
<313> RELEVANT RESIDUES IN SEQ ID NO: (1)..(1657)

<400> SEQUENCE: 4
gcttccggcg gaagcggcct caacaaggga aactttattg ttcccgtggg gcagtcgagg     60
atgtcggtga attacgcggc ggggctgtcg ccgtacgcgg acaagggcaa gtgcggcctc    120
ccggagatct tcgaccccc ggaggagctg agcggaagg tgtgggaact ggcgaggctg      180
gtctggcagt cttccagtgt ggtgttccac acgggtgccg gcatcagcac tgcctctggc    240
atccccgact tcagggtgcc ccacggagtc tggaccatgg aggagcgagg tctggcccc    300 aagttcgaca ccacctttga gagcgcgcgg cccacgcaga cccacatggc gctggtgcag   360
ctggagcgcg tgggcctcct ccgcttcctg gtcagccaga acgtggacgg gctccatgtg   420
cgctcaggct tccccaggga caaactggca gagctccacg ggaacatgtt gtggaagaa   480 tgtgccaagt gtaagacgca gtacgtccga gacacagtcg tgggcaccat gggcctgaag   540
gccacgggcc ggctctgcac cgtggctaag gcaggggcc tgcgagcctg caggggagag    600
ctgagggaca ccatcctaga ctgggaggac tccctgcccg accgggacct ggcactcgcc   660
gatgaggcca gcaggaacgc cgacctgtcc atcacgctgg gtacatcgct gcagatccgg   720
cccagcggga acctgccgct ggctaccaag cgccggggag gccgcctggt catcgtcaac   780
ctgcagccca ccaagcacga ccgccatgct gacctccgca tccatggcta cgttgacgag   840
gtcatgaccc ggctcatgaa gcactgggg ctggagatcc ccgcctggga cggcccccgt    900
gtgctggaga gggcgctgcc acccctgccc cgcccgccca ccccaagct ggagcccaag    960
```

| | |
|---|---|
| gaggaatctc ccacccggat caacggctct atccccgccg gccccaagca ggagccctgc | 1020 |
| gcccagcaca acggctcaga gcccgccagc cccaaacggg agcggcccac cagccctgcc | 1080 |
| ccccacagac cccccaaaag ggtgaaggcc aaggcggtcc ccagctgacc agggtgcttg | 1140 |
| gggagggtgg ggcttttttgt agaaactgtg gattctttttt ctctcgtggt ctcactttgt | 1200 |
| tacttgtttc tgtccccggg agcctcaggg ctctgagagc tgtgctccag gccaggggtt | 1260 |
| acacctgccc tccgtggtcc ctccctgggc tccaggggcc tctggtgcgg ttccgggaag | 1320 |
| aagccacacc ccagaggtga caggtgagcc cctgccacac cccagcctct gacttgctgt | 1380 |
| gttgtccaga ggtgaggctg ggccctccct ggtctccagc ttaaacagga gtgaactccc | 1440 |
| tctgtcccca gggcctccct tctgggcccc ctacagccca ccctacccct cctccatggg | 1500 |
| ccctgcagga ggggagaccc accttgaagt gggggatcag tagaggcttg cactgccttt | 1560 |
| ggggctggag ggagacgtgg gtccaccagg cttctggaaa agtcctcaat gcaataaaaa | 1620 |
| caatttcttt cttgcaaaaa aaaaaaaaaa aaaaaa | 1657 |

<210> SEQ ID NO 5
<211> LENGTH: 1028
<212> TYPE: DNA
<213> ORGANISM: Homo sapiens

<400> SEQUENCE: 5

| | |
|---|---|
| cttttcactt gtgaatacca attaggtttc cagtttctca taaagatcta acaaataccc | 60 |
| aatttctcca tcagactgac atcccttaac aaaagcagag tttcaattcc ctgcatctcc | 120 |
| tttaggagct atgatataat gtaggtagaa atcttgcctt aactccattt acccactgtg | 180 |
| ctataaataa gcagaagcaa atattttttt aaggctggag aggttttaaa aatctgaact | 240 |
| aatttagcaa ctgctgctgc actcagtttt tggcagttcc caaacatcca ttatcatgta | 300 |
| aggataaatc cttctaaacc agaaaaatgt ttcctacttg gaaaggcat aagaaaatac | 360 |
| atatacgacc tccccatgta ctagtcttac atacccccagc tccagttaga actataattt | 420 |
| ttttgcactc ttgcagtaat ttcacagcat cttcaattgt attaatatct tttctttttt | 480 |
| tccttttttgg tggttctgaa aggatattaa taacaatctg ccacagtgtc atatcatcca | 540 |
| actcaggtgg aggtattgtt tccggcaata aatctttaag aattgttcga ggatctgtgc | 600 |
| caatcataag atgttgctga acaaaagtat atggacctac aataagggg aaaaggctta | 660 |
| aagtcaactt atcaagtaat tcaaaatctc atttattttc tgaagtaatg agttagcatt | 720 |
| ctgtgagggt tttttgcaaa gtaagaaaat gcaatttaat ggtatttcat tctcggtaca | 780 |
| ctcagaatta atgctatatc ccaatgagat taggaagatc taatgaagag ttgggaagac | 840 |
| ccccttcagc tgtaagtata tatttcaaga gtctaattaa ttaacaacca gaattaagtt | 900 |
| cttatggtta atatctagaa acacacacca taataccaaa agtatttaca aaagggttct | 960 |
| acgacataga aaaatcgtac cagtcctaaa agcctgtact acttatcatt aaaaccacac | 1020 |
| aggaaaaa | 1028 |

<210> SEQ ID NO 6
<211> LENGTH: 429
<212> TYPE: DNA
<213> ORGANISM: Homo sapiens
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (373)..(373)
<223> OTHER INFORMATION: n is a, c, g, or t
<220> FEATURE:
<221> NAME/KEY: misc_feature
<222> LOCATION: (400)..(400)
<223> OTHER INFORMATION: n is a, c, g, or t

<400> SEQUENCE: 6

```
cgacganaac ataagcactt ttaatttcct ctctattatg ctacagacaa ggccgaagac    60
tgggtttttt aggttgttta aggctgtaaa gaaaacaaag aacatatgac agagacccta   120
tgcagtctgc aaagcatact acatatttac taccaggccc taccttacta cagaaagttt   180
gctgatccag ctgtgaacat ataccccgat gcagatgaaa acaaatacaa aacaaaccta   240
acttgccatt ttggtcacaa gagcaagtaa gtagcagagc cctgttttga tatgaaaatc   300
cagcactgga ctgggcaaca tggcgagacc ccatctctac caaaaatact aaaaaaatag   360
ccgggcatgg tgnggcacat ctgtagtact agctacttgn gaggctgaga caggagaatc   420
atttgagcc                                                            429
```

<210> SEQ ID NO 7
<211> LENGTH: 156
<212> TYPE: DNA
<213> ORGANISM: Homo sapiens

<400> SEQUENCE: 7

```
cctgtatata cacacactat gcaatagtct taggtaacta attagctgca accctaaggt    60
agatcaaata gaaaatgtca agtcgccaca atcacatcat cttaattaat atggagggaa   120
ggtaggaatc tgttactctt cccaacacta agcttt                              156
```

<210> SEQ ID NO 8
<211> LENGTH: 593
<212> TYPE: DNA
<213> ORGANISM: Homo sapiens
<220> FEATURE:
<221> NAME/KEY: misc_feature
<222> LOCATION: (460)..(460)
<223> OTHER INFORMATION: n is a, c, g, or t
<220> FEATURE:
<221> NAME/KEY: misc_feature
<222> LOCATION: (571)..(571)
<223> OTHER INFORMATION: n is a, c, g, or t

<400> SEQUENCE: 8

```
tctcactgtc tcccaggctg gagcgcaatg gtgcaatctt ggctcgctgc aacctccaac    60
tcccaggttc aagtgattct cgtgcctcag cctcctgagt agctgggatt acaggcgcct   120
gccaccatgc ccggctaatt ttagtatttc tagtagagtt gggatttcac catgttggcc   180
aagctgttct cgaactcttg gcttcatggg atctgcccgc tcggcttcc caaagtgcta   240
ggattacagg cgtgagccac tgcactcagc cagaaaagat tatttaaaat aattgaatgc   300
atgcaactgc agcatctttt gaaatcaaaa gcaaattaat atctgaggtt ttctataatt   360
aactgtcaag gccaatactt ctggttttat tattttttggt ttctactttt ctgaggttat   420
cgataaatgg agaaacatga ttaaataaat gctttatctn cacttctcga tggcagtcag   480
ctttaatgga aaatatttc ctataaacct aaattaattt ccggaaaccc cttttgaggt   540
taactaccat tgcactggaa taatctttgg natcccggaa ccctgttcaa ggg          593
```

<210> SEQ ID NO 9
<211> LENGTH: 373
<212> TYPE: DNA

<213> ORGANISM: Homo sapiens

<400> SEQUENCE: 9

| ggcacttcat gggggtatgga acctaaaata gggtgaaaaa taagagttag aaaaagggag | 60 |
|---|---|
| gaggaagtaa gctaataaaa ccacaacaga tacattatgc aaaaatccaa caagggcttg | 120 |
| agctccaaat tcccaaaaaa gacccatgca ctaaatactt aaccaagcca ttacatttca | 180 |
| tcaagcaagc agatgggcag ttaagtgtct tttataaaac gctcaagttc tgctcctatc | 240 |
| acctggttac ccctgagcaa tcttcccaga ctttcccact ctgaacctca aatttccttg | 300 |
| tctgcagaat ggggatgata atagtacttc tccacaagac tgtggtgagg attaaatgag | 360 |
| ttagtcaagt gca | 373 |

<210> SEQ ID NO 10
<211> LENGTH: 1713
<212> TYPE: DNA
<213> ORGANISM: Mus musculus

<400> SEQUENCE: 10

| gggctcccct cagcggcctc tggcgcctcc cgcccgcccg accgttcgc tcgctcgctc | 60 |
|---|---|
| gctcgctcgc ttgctcgtcc gggatcgccg cggtggttca agtttgcgat ggcgccgcca | 120 |
| cttcccacct gggcctcacg cgtgcacctt gcctgcctgc gcctcttcgc ctcaagtcgg | 180 |
| cttttacctc aggggctctg gagagcccaa cctggccgac gccggccttc ctgaggagaa | 240 |
| ctcctccacc tgccttgccc ttgctctgtg acagctcttc ctcaggttac ccctgtggtc | 300 |
| tctcctcagg aagtttgcgc tctctcccaa tctcccttct caagtgcaat ggaatgccca | 360 |
| agccagccct cggggcctgt tgccctcctg gaaagatctg gcgattgagg acccgcccta | 420 |
| tctgctctct ggacccacca ggtcctctgt acctcgcttt agtctttggt aaaattcatc | 480 |
| tcttggggca gcaagagaga ggacagaagg gagagtggtt ggttctccac aaacttctgt | 540 |
| gttaagagtc agattgggcc tgggctcttg tgacttgggc gattgactga acctttctca | 600 |
| agcccagttt ttaatcatct ctaaaatgac agggccagga ccgaaagaga ctgtagctca | 660 |
| gttgtaaagt cacgcttgcc agacaacccc gaagccctag agagagggag gaaggagggt | 720 |
| aagttgaagg taatctccaa ctacttagga agttcaaaaa aggcctggaa tacataagac | 780 |
| ctcgtctcaa aaacgaaatt taaaacgata gaccatgaga aatcagctag tcaggtttaa | 840 |
| agtaaatgac attagtttta aaatcctagg cagttgatgg tggcacaggc ctttaatccc | 900 |
| agcaagctgg aggagacagg aggaggttca ctaggacagc caaggctaca caagaaaacc | 960 |
| ctgtctcgaa aaaataatct tacttctaga attgtagaaa tggctctgta gttaacagca | 1020 |
| cttgttgctc ctgcagaggc cctaggtttg actcccatca tccacatgac agctcatacc | 1080 |
| ttcagatctg acacctgctt ttggtaaaca cagacatgta tggagccaaa agacccaaac | 1140 |
| acataaaaat cctctttgtt gttgttttat gagttagggt ttctctgtgt agccctggct | 1200 |
| gtccaggaac tctgtagatc aggctgtcct tgaactcaga ggccacctgc ctctgcttct | 1260 |
| tgaactgctg ggattaaaga tgtacaccag caagcccagc ataaaaatac atatttaaat | 1320 |
| aatttttttaa ataatcctta gttccttcac aactctaagc cccttcactt tctagttacc | 1380 |
| atgaaattct gagcacctgt atccatttgg atcattaggg ctcaattgca catggttcaa | 1440 |
| ttacagtggg gtttccccag attttagagt tagaggcagc aggatcagaa aattaaatcc | 1500 |
| atttgcacta ggtaataaat ttgatcccac cctatctcaa aaacaaaaca ctagccacac | 1560 |
| gtggcagcac acacctttta caacaggact caggagcctg gcatgatggg acagaccttt | 1620 |

```
actccctgca cttgaggcag atgcaggcaa atctaggcat cctggtgtac atatgaagtt    1680
caggcaagcc agggccacgt aggctcaaag acg                                 1713

<210> SEQ ID NO 11
<211> LENGTH: 660
<212> TYPE: DNA
<213> ORGANISM: Homo sapiens
<220> FEATURE:
<221> NAME/KEY: misc_feature
<222> LOCATION: (587)..(587)
<223> OTHER INFORMATION: n is a, c, g, or t
<220> FEATURE:
<221> NAME/KEY: misc_feature
<222> LOCATION: (628)..(628)
<223> OTHER INFORMATION: n is a, c, g, or t

<400> SEQUENCE: 11 ttttttttt tttttttccc acaggtagat aagagtcttg ctctgtcacc caggctggag      60
tgcagtggct caatcatagc tcactgcagc cttgaactcc tggactcaag ggatcctctt    120
gccttagtct caggagtaac tgggacaaca ggcttgcgcc accatgcccg gctaattttt    180 aaattttttgg tagagatggg ggtctcgtta tgttgcccag gctgctcttg aactcctggc    240
ctcgagcgat ccccgtctca gcctccgaaa gtgctggtat tacaagtgtg agctaccact    300
tcgagactca cttttcacca acattttcag cagttgtgtc agacagcaag tcaatgtgcc    360
attatttact taaatattca tccattatag ggcatctgat acctaacaac catggacctt    420 aagattttttt cctatgtagc ctcagttctt agatgcaatt actatgggaga cgggtacgat    480 cacatgccag tgggagtatt aaccgcacaa catttatgag ggatcattaa agcgttaaat    540
gcatatactt ttggacctag caatcccagt actaggaatt tatgcanaca gtgaggtgcc    600
aacaaggtta ttcaccacag catgatgnca caatactaaa ggttagaacg tatttcaatg    660

<210> SEQ ID NO 12
<211> LENGTH: 589
<212> TYPE: DNA
<213> ORGANISM: Homo sapiens

<400> SEQUENCE: 12
agtctggtgt ctcatctctc gccccggagg tcaaacctgg agccagcatt tctgtaccct     60
gcgctcacac cttttcaac ccggatggcg gtgatagtta atactttctg agcgcttta    120 ctatggtcag gcattatatt tacacctaat cctcgcaaaa cactactggg aagatcctca    180
tttgacagga gcaattccgg gtcacaaagg ctgacaccac aaagctagtc cgtagcgggt    240
tcgaccacag gcgcccacac tctttgacgc tcaatggca cagccaagtg cgcgggaagt    300
gggctgcaaa cgccggagag ttttgtccgg agcgcagaga cgcgctgtaa ccgagcaacc    360
agcggggccc gccccggcc tgctacggcg ctcccagcct gccccgcgcc gctcggcgcc    420
ggaagtgagt gagcatttcc ggcagccatc ccgcgcgtgc tgacatcccg gttgttcttc    480
tgtgccgggg gtcttcctgc tgtcatgaag gacgtaccgg gcttcctaca gcagagccag    540
aactccgggc ccgggcagcc cgctgtgtgg caccgtctgg aggagctct              589

<210> SEQ ID NO 13
<211> LENGTH: 428
<212> TYPE: DNA
<213> ORGANISM: Homo sapiens

<400> SEQUENCE: 13
```

| | |
|---|---:|
| agggtgagtt gcaagacagg aagaggggga tagaacaaga cacagacaga gagataaaga | 60 |
| gttaaagaca aagcaagtca gagacagaat tggagagaga cagagagagg gagaggcaga | 120 |
| gagagagaga tgaattcaca cgaaggcaaa aatgacttat tctattcaac caacactgct | 180 |
| gctgcaatga gcccgacgat gctcacatgg gcccaagccc tgccctccag aagcccttga | 240 |
| tcttggggga gacaggtgga cacagatcct ctggccccaa gagtcaagcc tggatcagag | 300 |
| gaggtacctg ggcctgggga agccccgtgg aggtgggggc cctggggcac gtggaagggc | 360 |
| ttcctggagg aggctaagca gtttcttgaa gggtgagagg aagatcaga cagaagggat | 420 |
| cctctaga | 428 |

<210> SEQ ID NO 14
<211> LENGTH: 4041
<212> TYPE: DNA
<213> ORGANISM: Homo sapiens

<400> SEQUENCE: 14

| | |
|---|---:|
| gtggcctgga ggactcattt aagaatcatg tgttgagtac ctactttgta ctgggcacac | 60 |
| tggagagcaa aggtggtacc atctatgccc tggtggctgc gggtggacac aaacatgtga | 120 |
| ccaggggcca ggactggtca ggaaggagga agcggtcctt ttgaggaggg cgaggcaacg | 180 |
| gaccctgccg cccaccagga ctggtgtccc tcaccttacc cccacccttg ccctcctcag | 240 |
| gtggcctgtg gagaggagaa acacagggca ccaactatga agactctcag ggcgcgattt | 300 |
| aagaagacag agctgcggct cagccccact gaccttggct cctgcccgcc ctgcggcccc | 360 |
| tgccccatcc cgaagccggc agccagaggc aggcgccaga gtcaagactg ggcaagagt | 420 |
| gacgagaggc tgctacaagc cgtggaaaac aacgatgcac ctcgggtggc cgccctcatc | 480 |
| gcccgcaagg ggctggtgcc cacgaagcta gaccccgagg gcaagtccgc gttccacctg | 540 |
| gcggccatgc ggggtgcggc cagctgtctg gaggtgatga tagctcatgg cagcaatgtc | 600 |
| atgagcgcgc acgggcagg ttacaatgcc ctccacctgg ccgccaaata cgggcaccca | 660 |
| cagtgcttga agcaactact gcaggcttcc tgcgtggtgg acgtcgtgga cagcagcggg | 720 |
| tggactgccc tacaccatgc agcggctggt ggctgtctct cctgctcaga ggtgctctgc | 780 |
| tcctttaagg cacatctaaa cccccaagat cggtcaggcg caacacccct cattatagca | 840 |
| gctcagatgt gtcacacaga cctgtgccgt ctcctactgc agcaaggggc tgccgcgaac | 900 |
| gatcaggacc tgcaaggcag gacggccctg atgctggcct gtgaggggc cagccccgaa | 960 |
| acagtggagg tcctgctgca gggcggagcc cagccgggca tcaccgatgc gctggggcag | 1020 |
| gacgcggctc actatggcgc cctggcgggg gacaaactca tcctgcacct tctgcaagag | 1080 |
| gcggcccagc gcccctcccc acccagcgcc ctcacagagg atgattcagg cgaggcgtca | 1140 |
| tctcagaact ctatgtccag ccatggaaag cagggggccc ccaagaagcg gaaggcgcct | 1200 |
| ccacctcccg ccagcattcc catgccggat gatcgagatg cctatgagga gatcgtgagg | 1260 |
| ctgcggcagg agagggccg cctcctgcag aagatccggg gcctggaaca gcacaaggaa | 1320 |
| cggaggcagc aggagtcccc ggaggccagc tccctgcaca tcctggagag acaggtgcaa | 1380 |
| gagctacagc agttgctggt ggagagacaa aggagaagg agagcctggg acggaggtg | 1440 |
| gagagtttgc agagccggct gtccctgctg gagaacgagc gggagaatac tagctatgac | 1500 |
| gtaaccaccc tgcaggatga ggagggtgag ctgcctgacc ttccaggggc gaggtgctg | 1560 |
| ctgtccagac aactcagtcc gtcggcccag gaacacctgg cctcgctgca ggaacaggtg | 1620 |
| gctgtgctca ccagacagaa ccaggaactg atggagaagg tccagatcct ggagaacttt | 1680 |

```
gagaaggacg agacacagat ggaagtggaa gctttggcag aggtcatccc tcttgccctc    1740
tatgactctc tccgggccga gtttgaccag ctacgcaggc agcacgctga ggccctgcag    1800
gccctgaggc agcaggagac acgagaggtc cccagagaag aggggggcagc ctgtggggag   1860
agtgaggttg ctggagccac ggccaccaaa aacgggccaa cccacatgga gctaaatggc    1920
tcagtggctc cagaaaccaa agttaacgga gccgagacca tagatgagga ggctgcagga    1980
gatgaaacca tggaagccag gactatgaaa gctgaggcca cggagccgga ggccacggga    2040
gctgaggcca caggagccaa ggtcacagaa acaaaaccca caggggctga ggtcagagaa    2100
atggagacca cagaagaaga agcaaacatg gaaactaagc ccacaggagc tcaggccaca    2160
gacacagaga ccacgggagt ggaggccatg ggggtggagg ccacaaaaac aaaagcagag    2220
gaagcagaaa tgcaggccta cggagtgggt gctgggcaag cagagccccc agtcacaggg    2280
accacaaaca tggaggccac gggctctagg gccacaggga tggaatccac aggagtcagt    2340
gccacaggtg tggagaaccc aggggtagag gccacggtcc cggggatctc tgctggcccc    2400
atcctacatc ctggtgccgc agaggcctcg gaaaagcttc aagtagagct ggagaccagg    2460
atccgtggct tggaggaggc tctccggcag cgggagcggg aggcagctgc ggagctggag    2520
gcggccctgg ggaagtgcga ggccgcggag gccgaggcag gccggctgcg agagcgtgtc    2580
cgcgaggccg agggcagcgg ggccagcggg ggcggtggcg gtgacaccac acagctgcgg    2640
gcggccctgg agcaggcccg ggaggacctc cgagaccggg actcccgcct gcgggagctg    2700
gaggcggcct cggcctgcct ggatgaggct cgggccagcc ggctgctggc ggaggaggag    2760
gcgcggggcc tgcgggccga gctggcccag cgggaggagg cgcggctgga gcagagccgg    2820
gagctggagg ttctgcggga gcagctggcc acggccaggg ccacggggga gcagcagcgc    2880
acggcggccg cggaactggg ccgggcacgg gacgccgctg aggcccgagt ggctgagctg    2940
cctgcggcct gcgaggaggc gcggcagggc ctggccgagc tgcggaggc ctccgaggcc     3000
ctccgccagt ccgtggtgcc ggcctctgag caccgccggc tgcaggagga ggccctggag    3060
ctgcggggcc gggcagccag tctggagcag gaggtggtgg ccacgggcaa ggaggccgcc    3120
cggctgcgcg cggagctgga gcgggagcgt gtgtgcagcg tggcgctctc ggagcacgaa    3180
cgcatcgtgg gcaccctgca ggccaacgtg gcccagctgg aggggcagct ggaggagctg    3240
ggacggcggc atgagaagac cagcgcagag gtcttccagg tgcagcgtga ggccctgttc    3300
atgaagagtg agcgacacgc agccgaggca cagctggcca cagcagagca gcagctacgg    3360
gggctacgga ccgaggcgga aagggctcgc caggcccaga gccgggccca ggaggctctg    3420
gacaaggcca aggagaagga caagaagatc acagaactct ccaaagaagt cttcaatctt    3480
aaggaagcct tgaaggagca gccggccgcc tcgccacccc tgaggtgga ggctctccgt     3540
gaccaggtga aggatttaca gcagcagctg caggaagctg ccaggaccag ctccagcgtg    3600
gtggctttgt acagaagcca cctcctatat gccattcagg gccagatgga tgaagatgtg    3660
cagcggattc tcagccagat tctgcagatg cagagactcc aggctcaggg ccgctgagaa    3720
aggccaggcc cagtggctac actgaccaca cccacgcagg gacctcaccc ccctgcaggc    3780
cccttgcaga ccggcttcac ttggcttcac ttggccctat ccaggcccat gcacttggag    3840
accagcctgg ttccctgccc gaccacccc agctggctcc atcacccac ctggtctctg       3900
cacgcacaca ctggtcagtc tggacccggg ccgtgactgc cctccccca ccaccggaga     3960
ctgtgattcc ctgtgtcctc cacatccaga cgccagccca ggaataaagg cattctgtgc    4020
```

```
acagggaaaa aaaaaaaaaa a                                              4041

<210> SEQ ID NO 15
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 15
ttggtattca caag                                                        14

<210> SEQ ID NO 16
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 16
aaactggaaa ccta                                                        14

<210> SEQ ID NO 17
<211> LENGTH: 14
<212> TYPE: DNA
<213> ORGANISM: Artificial Sequence
<220> FEATURE:
<223> OTHER INFORMATION: Antisense Oligonucleotide

<400> SEQUENCE: 17
gatctttatg agaa                                                        14

<210> SEQ ID NO 18
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 18
gatggagaaa ttgg                                                        14

<210> SEQ ID NO 19
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 19
agtctgatgg agaa                                                        14

<210> SEQ ID NO 20
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 20
tgttaaggga tgtc                                                        14

<210> SEQ ID NO 21
<211> LENGTH: 14
<212> TYPE: DNA
<213> ORGANISM: Artificial Sequence
```

```
<220> FEATURE:
<223> OTHER INFORMATION: Antisense oligonucleotide

<400> SEQUENCE: 21
aatctgcttt tgtt                                                        14

<210> SEQ ID NO 22
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 22
agggaattga aatc                                                        14

<210> SEQ ID NO 23
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 23
taaggcaaga tttc                                                        14

<210> SEQ ID NO 24
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 24
taaatggagt taag                                                        14

<210> SEQ ID NO 25
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 25
ttatttatag caca                                                        14

<210> SEQ ID NO 26
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 26
ttgcttctgc ttat                                                        14

<210> SEQ ID NO 27
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 27
aaaaaaatat ttgc                                                        14
```

```
<210> SEQ ID NO 28
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 28
cagccttaaa aaaa                                                         14

<210> SEQ ID NO 29
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 29
ttttaaaacc tctc                                                         14

<210> SEQ ID NO 30
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 30
tagttcagat tttt                                                         14

<210> SEQ ID NO 31
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 31
agcagttgct aaat                                                         14

<210> SEQ ID NO 32
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 32
ctgagtgcag cagc                                                         14

<210> SEQ ID NO 33
<211> LENGTH: 12
<212> TYPE: DNA
<213> ORGANISM: Artificial Sequence
<220> FEATURE:
<223> OTHER INFORMATION: Antisense oligonucleotide

<400> SEQUENCE: 33
gtctgatgga ga                                                           12

<210> SEQ ID NO 34
<211> LENGTH: 12
<212> TYPE: DNA
<213> ORGANISM: Artificial Sequence
<220> FEATURE:
<223> OTHER INFORMATION: Antisense oligonucleotide
```

```
<400> SEQUENCE: 34
gtctgatgga ga                                                             12

<210> SEQ ID NO 35
<211> LENGTH: 12
<212> TYPE: DNA
<213> ORGANISM: Artificial Sequence
<220> FEATURE:
<223> OTHER INFORMATION: Antisense oligonucleotide

<400> SEQUENCE: 35
gtctgatgga ga                                                             12

<210> SEQ ID NO 36
<211> LENGTH: 12
<212> TYPE: DNA
<213> ORGANISM: Artificial Sequence
<220> FEATURE:
<223> OTHER INFORMATION: Antisense oligonucleotide

<400> SEQUENCE: 36
guctgatgga ga                                                             12

<210> SEQ ID NO 37
<211> LENGTH: 12
<212> TYPE: DNA
<213> ORGANISM: Artificial Sequence
<220> FEATURE:
<223> OTHER INFORMATION: Antisense oligonucleotide

<400> SEQUENCE: 37
gucugaugga ga                                                             12

<210> SEQ ID NO 38
<211> LENGTH: 27
<212> TYPE: DNA
<213> ORGANISM: Artificial Sequence
<220> FEATURE:
<223> OTHER INFORMATION: Antisense oligonucleotide

<400> SEQUENCE: 38
actgacacct aattgtattc acatgaa                                             27

<210> SEQ ID NO 39
<211> LENGTH: 26
<212> TYPE: DNA
<213> ORGANISM: Artificial Sequence
<220> FEATURE:
<223> OTHER INFORMATION: Antisense oligonucleotide

<400> SEQUENCE: 39
tgagcagcag ttgctaaatt agttca                                              26

<210> SEQ ID NO 40
<211> LENGTH: 27
<212> TYPE: DNA
<213> ORGANISM: Artificial Sequence
<220> FEATURE:
<223> OTHER INFORMATION: Antisense oligonucleotide

<400> SEQUENCE: 40
tctacctaca ttatatcata gctccta                                             27

<210> SEQ ID NO 41
```

```
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 41
ttggtattca caagtgaaa                                                    19

<210> SEQ ID NO 42
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 42
ttgctaaatt agttcagat                                                    19

<210> SEQ ID NO 43
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 43
gcagcagcag ttgctaaat                                                    19

<210> SEQ ID NO 44
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 44
gcagttgcta aattagttc                                                    19

<210> SEQ ID NO 45
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 45
gccatgttgc ccagtccagt                                                   20

<210> SEQ ID NO 46
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 46
gggctctgct acttacttgc                                                   20

<210> SEQ ID NO 47
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 47
```

-continued

```
cccagtcttc agccttgtct                                    20

<210> SEQ ID NO 48
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 48
gggtctctgt catatgttct t                                  21

<210> SEQ ID NO 49
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 49
ttcctacctt ccctccata                                     19

<210> SEQ ID NO 50
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 50
attcctacct tccctccat                                     19

<210> SEQ ID NO 51
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 51
ccttagggtt gcagctaatt                                    20

<210> SEQ ID NO 52
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 52
atcccagcta ctcaggaggc                                    20

<210> SEQ ID NO 53
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 53
tctggctgag tgcagtggct                                    20

<210> SEQ ID NO 54
<211> LENGTH: 20
<212> TYPE: DNA
```

```
<213> ORGANISM: Artificial Sequence
<220> FEATURE:
<223> OTHER INFORMATION: Antisense oligonucleotide

<400> SEQUENCE: 54
cctgggagtt ggaggttgca                                                    20

<210> SEQ ID NO 55
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 55
cagatcccat gaagccaaga g                                                  21

<210> SEQ ID NO 56
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 56
ctgactgcca tcgagaagtg g                                                  21

<210> SEQ ID NO 57
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 57
gcccatctgc ttgcttgat                                                     19

<210> SEQ ID NO 58
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 58
atcctcacca cagtcttgt                                                     19

<210> SEQ ID NO 59
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 59
gcttacttcc tcctcccttt                                                    20

<210> SEQ ID NO 60
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 60
ccaggtgata ggagcagaac t                                                  21
```

```
<210> SEQ ID NO 61
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 61
accctccttc ctccctctct                                           20

<210> SEQ ID NO 62
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 62
ccactctccc ttctgtcctc t                                         21

<210> SEQ ID NO 63
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 63
cctccttcct ccctctctct                                           20

<210> SEQ ID NO 64
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 64
gtctgtccca tcatgccagg                                           20

<210> SEQ ID NO 65
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 65
tttctgatcc tgctgcctct                                           20

<210> SEQ ID NO 66
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 66
accctccttc ctccc                                                15

<210> SEQ ID NO 67
<211> LENGTH: 14
<212> TYPE: DNA
<213> ORGANISM: Artificial Sequence
<220> FEATURE:
```

<223> OTHER INFORMATION: Antisense oligonucleotide

<400> SEQUENCE: 67
ctccttcctc cctc                                                              14

<210> SEQ ID NO 68
<211> LENGTH: 11
<212> TYPE: DNA
<213> ORGANISM: Artificial Sequence
<220> FEATURE:
<223> OTHER INFORMATION: Antisense oligonucleotide

<400> SEQUENCE: 68
ctccttcctc c                                                                 11

<210> SEQ ID NO 69
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 69
cttcctccct ctctc                                                             15

<210> SEQ ID NO 70
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 70
atcctgctgc ctct                                                              14

<210> SEQ ID NO 71
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 71
ctccttcctc cctc                                                              14

<210> SEQ ID NO 72
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 72
accctccttc ctccc                                                             15

<210> SEQ ID NO 73
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 73
gttctggctc tgctgtagga                                                        20

```
<210> SEQ ID NO 74
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 74
atgctcactc acttccggcg                                              20

<210> SEQ ID NO 75
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 75
ctttgtggtg tcagcctttg t                                            21

<210> SEQ ID NO 76
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 76
aggtgtgagc gcagggtaca                                              20

<210> SEQ ID NO 77
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 77
ctcggttaca gcgcgtctct                                              20

<210> SEQ ID NO 78
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 78
aactctccgg cgtttgcag                                               19

<210> SEQ ID NO 79
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 79
tgttgtccca gttactcct                                               19

<210> SEQ ID NO 80
<211> LENGTH: 20
<212> TYPE: DNA
<213> ORGANISM: Artificial Sequence
<220> FEATURE:
<223> OTHER INFORMATION: Antisense oligonucleotide
```

<400> SEQUENCE: 80
gccaggagtt caagagcagc 20

<210> SEQ ID NO 81
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 81
ccttgttggc acctcactgt 20

<210> SEQ ID NO 82
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 82
gttgtgcggt taatactccc 20

<210> SEQ ID NO 83
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 83
gtgagtctcg aagtggtagc t 21

<210> SEQ ID NO 84
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 84
gactcttatc tacctgtggg a 21

<210> SEQ ID NO 85
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 85
tccttctcct cttgtctctc c 21

<210> SEQ ID NO 86
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 86
gccctgtgtt tctcctctcc 20

<210> SEQ ID NO 87
<211> LENGTH: 21

```
<212> TYPE: DNA
<213> ORGANISM: Artificial Sequence
<220> FEATURE:
<223> OTHER INFORMATION: Antisense oligonucleotide

<400> SEQUENCE: 87
actcccgtgg tctctgtgtc t                                              21

<210> SEQ ID NO 88
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 88
tccagcaacc tcactctccc                                                20

<210> SEQ ID NO 89
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 89
gcgtgggtgt ggtcagtgta                                                20

<210> SEQ ID NO 90
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 90
accacctcct gctccagact                                                20

<210> SEQ ID NO 91
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 91
cctctccctc tctctgtctc t                                              21

<210> SEQ ID NO 92
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 92
atcttccctc tcacccttc                                                 19

<210> SEQ ID NO 93
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 93
```

-continued cccttctgtc tgatcttccc t    21

<210> SEQ ID NO 94
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 94
tctgtgtcca cctgtctccc    20

<210> SEQ ID NO 95
<211> LENGTH: 25
<212> TYPE: DNA
<213> ORGANISM: Homo sapiens

<400> SEQUENCE: 95
aactggagct ggggtgtctg tttca    25

<210> SEQ ID NO 96
<211> LENGTH: 25
<212> TYPE: DNA
<213> ORGANISM: Artificial Sequence
<220> FEATURE:
<223> OTHER INFORMATION: Forward Primer Sequence

<400> SEQUENCE: 96
ccatcagacg acatccctta acaaa    25

<210> SEQ ID NO 97
<211> LENGTH: 31
<212> TYPE: DNA
<213> ORGANISM: Artificial Sequence
<220> FEATURE:
<223> OTHER INFORMATION: Reverse Primer Sequence

<400> SEQUENCE: 97
acattatatc atagctccta aaggagatgc a    31

<210> SEQ ID NO 98
<211> LENGTH: 16
<212> TYPE: DNA
<213> ORGANISM: Artificial Sequence
<220> FEATURE:
<223> OTHER INFORMATION: Reporter Sequence

<400> SEQUENCE: 98
cagagtttca attccc    16

<210> SEQ ID NO 99
<211> LENGTH: 12
<212> TYPE: DNA
<213> ORGANISM: Artificial Sequence
<220> FEATURE:
<223> OTHER INFORMATION: Antisense Oligonucleotide

<400> SEQUENCE: 99
gctagtctgt tg    12

<210> SEQ ID NO 100
<211> LENGTH: 20
<212> TYPE: DNA
<213> ORGANISM: Artificial Sequence
<220> FEATURE:
<223> OTHER INFORMATION: Antisense Oligonucleotide

```
<400> SEQUENCE: 100
caccatgccc ggctaatttt                                              20

<210> SEQ ID NO 101
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 101
gaguucagau uuuuaacac                                               19

<210> SEQ ID NO 102
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 102
auucuccugc cucagccuc                                               19

<210> SEQ ID NO 103
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 103
ugaagaugcu gugaaauua                                               19
```